(12) United States Patent
Amrein et al.

(10) Patent No.: US 7,678,795 B2
(45) Date of Patent: Mar. 16, 2010

(54) PYRIDAZINES AS 11B-HSD1 INHIBITORS

(75) Inventors: Kurt Amrein, Itingen (CH); Daniel Hunziker, Moehlin (CH); Bernd Kuhn, Liestal (CH); Alexander V Mayweg, Loerrach (DE); Werner Neidhart, Hagenthal le Bas (FR)

(73) Assignee: Hoffman-La Roche Inc., Nutley, NJ (US)

( * ) Notice: Subject to any disclaimer, the term of this patent is extended or adjusted under 35 U.S.C. 154(b) by 632 days.

(21) Appl. No.: 11/481,330

(22) Filed: Jul. 5, 2006

(65) Prior Publication Data

US 2007/0010519 A1    Jan. 11, 2007

(30) Foreign Application Priority Data

Jul. 5, 2005    (EP)    .................................. 05106098

(51) Int. Cl.
C07D 237/36    (2006.01)
C07D 237/28    (2006.01)
A61K 31/502    (2006.01)

(52) U.S. Cl. ...................................... 514/248; 544/235
(58) Field of Classification Search ................. 544/235; 514/248
See application file for complete search history.

(56) References Cited

FOREIGN PATENT DOCUMENTS

WO    WO 2004/065351    8/2004
WO    WO 2004/089380    10/2004

OTHER PUBLICATIONS

Masuzaki H. et al., Science. Dec. 7, 2001; 294(5549):2166-70.
Walker et al. 1995; J. Clin. Endocrinol. Metab. 80, 31155-3159.
P.M. Stewart and Z.S. Krozowski, Vitam. Horm. 57 (1999), pp. 249-324.
Kotelevtsev Y. et al., Proc Natl Acad Sci U S A. Dec. 23, 1997;94(26):14924-9.
Masuzaki H. et al., J Clin Invest. Jul. 2003;112(1):83-90.
Rauz S. et al., QJM. Jul. 2003;96(7):481-90.
Sandeep TC. et al., Proc Natl Acad Sci U S A. Apr. 27, 2004;101(17):6734-9.
Huang, J. Chem. Soc., Perkin Trans. 1, 1989, 2397.
Boeckman, J. Am. Chem. Soc., 1986, 5549.
Albright, J. Org. Chem., 1965 30, 1107.
B. Kirschberger, Synthesis, 1986, 11, 926.
J. Am. Chem. Soc., 1974, 96, 7503.
K.C. Joshi, Heterocycles, 1981, 16, 1545.
D. Swern, Synthesis, 1981, 165.
Baumgarten, J. Am. Chem. Soc. 1958, 80, 6609.
Corey J. Am. Chem. Soc. 1969, 91, 4926.
Katritzky, J. Org. Chem. 1991, 56, 6917.
A. Baba (J. Org. Chem, 1997, 62, 8282.
Alex Odermatt et al.; J Biol Chem.,1999, vol. 274, Issue 40, 28762-28770.
R. W. Vander Haar, J. Org. Chem. 14, 1949, 836.
J. Kelder, Synth. Commun., 2, 1972, 125.
Alder et al, Justus Liebigs Ann. Chem., 593, 1955, 1, 17.
H. Meier, Synthesis, 1971, 215.
J. Chem. Soc., 121, 1922, p. 523.
Altomare, C. et al, Jour. of Med. Chem., 41:20 (1998) pp. 3812-3820, XP002976308.
South, M.S. et al , Jour. of Organic Chem., 61 (1996) pp. 8921-8934 XP002257942.
South, M.S. et al, Tetrahedron Ltrs, 36:32 (1995) pp. 5703-5706 XP004027583.
Nagarajan, K. et al, Inidan Jour. of Chem., vol. 25B:7 (1986) pp. 697-708 XP002976309.
Stetter H. et al, Chem. Ber., vol. 114 (1981) pp. 2479-2490 XP009071199.
Sprio V et al, Annali di Chimica, vol. 61:6 (1971) pp. 391-398 XP009071222.
Cocco M.T. et al, Gazzetta Chimica Italiana, vol. 114 (1984) pp. 521-524 XP009071196.

Primary Examiner—Kahsay T Habte
(74) Attorney, Agent, or Firm—George W. Johnston; Dennis P. Tramaloni; Samuel H. Megerditchian

(57) ABSTRACT

Compounds of formula

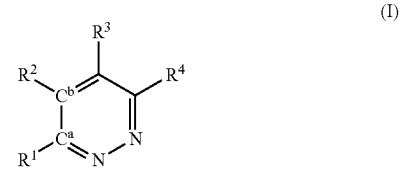

(I)

as well as pharmaceutically acceptable salts and esters thereof, wherein $R^1$ to $R^4$ have the significance given in claim 1 can be used in the form of pharmaceutical compositions.

17 Claims, No Drawings

PYRIDAZINES AS 11B-HSD1 INHIBITORS

PRIORITY TO RELATED APPLICATIONS

This application claims the benefit of European Application No. EP 05106098.6, filed Jul. 5, 2005, which is hereby incorporated by reference in its entirety.

FIELD OF THE INVENTION

The present invention is directed to novel pyridazine derivatives useful as 11b-HSD1 inhibitors (T2D).

The invention is preferably directed to compounds of formula I

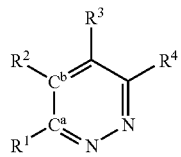

(I)

and pharmaceutically acceptable salts and esters thereof.

All documents cited or relied upon below are expressly incorporated herein by reference.

BACKGROUND

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors.

Glucocorticoid action on target tissues depends not only on circulating steroid concentrations and the cellular expression of receptors, but also on intracellular enzymes that critically determine to which extent glucocorticoids gain access to receptors in an active forms. 11beta-hydroxysteroid dehydrogenases (11beta-HSD's) catalyze the interconversion of the principal active 11-hydroxy-glucocorticoid (cortisol) and their inactive 11-keto metabolites (cortisone).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche, differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70.). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in men might have beneficial effects were obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11 beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be save and free of major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found to be healthy and to resist hyperglycemia provoked by obesity or stress (Kotelevtsev Y. et al., Proc Natl Acad Sci USA. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July; 112(1): 83-90; Rauz S. et al., Q J M. 2003 July; 96(7):481-90) to improve cognition (Sandeep T C. et al., Proc Natl Acad Sci USA. 2004 Apr. 27; 101(17):6734-9) or to improve Alzheimer associated deficits.

Taken together 11beta-HSD1 inhibition might be a safe and efficacious approach to treat symptoms of diabetes, obesity and other diseases. Thus, there is a need for novel compounds that inhibit 11-beta-HSD1.

SUMMARY OF THE INVENTION

In one embodiment of the present invention, provided is a compound of the formula:

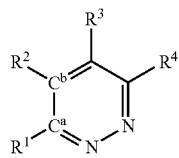

wherein
R[1] is cycloalkyl, arylalkyl or aryloxyalkyl;
R[2] is cycloalkyl, arylalkyl or aryloxyalkyl; or
R[1] and R[2] together with the carbon atoms $C^a$ and $C^b$ to which they are attached form

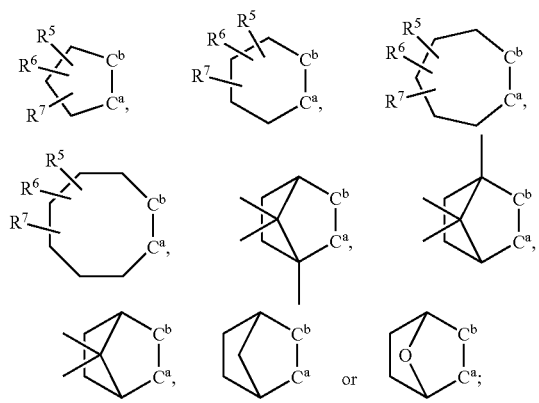

R[3] is hydrogen, alkyl, cycloalkyl or trifluoromethyl;
R[4] is benzyl, cycloalkyl, arylcycloalkyl, adamantyl, aryl or heterocyclyl, wherein benzyl, cycloalkyl, arylcycloalkyl, aryl and heterocyclyl are optionally substituted with one to three substituents independently selected from alkyl, cycloalkyl, alkoxy, hydroxy, halogen, trifluormethyl, trifluoromethoxy, benzyl, phenyl and phenyl substituted with one to three substituents independently selected from alkyl, alkoxy, hydroxy, cycloalkyl, halogen and trifluoromethyl;
R[5] is hydrogen, alkyl, cycloalkyl or alkoxy;
R[6] is hydrogen, alkyl cycloalkyl or alkoxy;
R[7] is hydrogen, alkyl, cycloalkyl or alkoxy;

and pharmaceutically acceptable salts and esters thereof; with the proviso that 3-(2-furanyl)-5,6,7,8-tetrahydro-5-methyl-chinnoline is excluded and that in case R[4] is unsubstituted phenyl at least one of R[5], R[6] and R[7] is not hydrogen or methyl.

In another embodiment of the present invention, provided is a process for the preparation of a compound according to formula I, comprising the step of reacting a compound according to formula

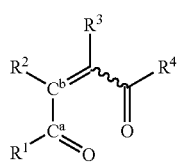

with hydrazine; wherein R[1] to R[4] are defined as in claim 1.

In a further embodiment of the present invention, provided is a pharmaceutical composition, comprising a therapeutically effective amount of a compound according to formula I and a therapeutically inert carrier.

In a yet another embodiment of the present invention, provided is a method for the treatment of diabetes, obesity, eating disorders, dyslipidemiae and hypertension, comprising the step of administering a therapeutically effective amount of a compound according to formula I to a patient in need thereof.

DETAILED DESCRIPTION

The compounds of formula I and their pharmaceutically acceptable salts and esters are novel and have valuable pharmacological properties. In particular they are 11-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II.

The compounds of this invention can further be used in the prophylaxis and/or treatment of high ocular eye pressure, cognition, Alzheimer and/or neurodegeneration.

Further, the compounds of this invention can be used for promoting wound healing, particularly by topical application. Moreover, the compounds of the present invention can be used to improve cognitive impairment, particularly impairement developed with age, and improvement of memory.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. Preferred cycloalkyl are methyl-cyclopropyl and particularly 1-methyl-cyclopropyl. Particularly preferred is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, trifluoromethoxy, nitro and trifluoromethyl.

The term "aryloxy", alone or in combination, signifies a aryl-O— group in which the term "aryl" has the previously given significance.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "oxy", alone or in combination, signifies the —O— group.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

The term "asymmetric carbon atom" (C*) means a carbon atom with four different substituents. According to the Cahn-Ingold-Prelog Convention the asymmetric carbon atom can be of the "R" or "S" configuration.

Preferred are the compounds of formula I and pharmaceutically acceptable salts thereof, particularly the compounds of formula I.

Preferred are compounds of formula I, wherein $R^4$ is cycloalkyl, arylcycloalkyl, adamantyl, aryl or heterocyclyl, wherein arylcycloalkyl, aryl and heterocyclyl are optionally substituted with one to three substituents independently selected from alkyl, alkoxy, hydroxy, halogen, trifluormethyl, phenyl and phenyl substituted with one to three substituents independently selected from alkyl, alkoxy, hydroxy, cycloalkyl, halogen and trifluoromethyl.

Further preferred are compounds of formula I, wherein $R^3$ is hydrogen or alkyl. Particularly preferred are those compounds of formula I, wherein $R^3$ is methyl. Further particularly preferred are compounds of formula I, wherein $R^3$ is hydrogen.

Preferred are those compounds of formula I, wherein the term "heterocyclyl" used in the definition of $R^4$ signifies pyrazolyl, thiazolyl, imidazoly, pyrrolyl, thiophenyl, triazolyl, pyridinyl, pyrimidinyl, pyazinyl, oxetanyl or indolyl. Particularly preferred are those compounds of formula I, wherein the term "heterocyclyl" used in the definition of R⁴ signifies pyrazolyl, thiazolyl or indolyl and in particular 1H-pyrazol-4-yl, thiazol-4-yl or 1H-indol-3-yl.

Preferred are compounds of formula I, wherein R⁴ is benzyl, cycloalkyl, phenylcycloalkyl, adamantyl, phenyl, indolyl, pyrazolyl, pyrrolyl or thiazolyl, wherein benzyl, cycloalkyl, phenylcycloalkyl, phenyl, indolyl, pyrazolyl, pyrrolyl and thiazolyl are optionally substituted with one to three substituents independently selected from alkyl, cycloalkyl, alkoxy, hydroxy, halogen, trifluormethyl, trifluoromethoxy, benzyl, phenyl and phenyl substituted with one to three substituents independently selected from alkyl, halogen and trifluoromethyl.

Further preferred are those compounds of formula I, wherein R⁴ is benzyl, cyclopropyl, methyl-cyclopropyl, cyclobutyl, phenylcyclopropyl, phenylcyclobutyl, adamantyl, phenyl, indolyl, pyrazolyl, pyrrolyl or thiazolyl, wherein benzyl, cyclopropyl, phenylcyclopropyl, phenylcyclobutyl, phenyl, indolyl, pyrazolyl, pyrrolyl and thiazolyl are optionally substituted with one to three substituents independently selected from alkyl, cycloalkyl, alkoxy, halogen, trifluormethyl, trifluoromethoxy, benzyl, phenyl and phenyl substituted with one to three substituents independently selected from alkyl, halogen and trifluoromethyl.

Another preferred embodiment of the present invention are the compounds according to formula I, wherein R⁴ is cycloalkyl, phenylcycloalkyl, adamantyl, phenyl, indolyl, pyrazolyl, oxetanyl or thiazolyl, wherein phenylcycloalkyl, phenyl, indolyl, pyrazolyl, oxetanyl and thiazolyl are optionally substituted with one to three substituents independently selected from alkyl, alkoxy, hydroxy, halogen, trifluormethyl, phenyl and phenyl substituted with one to three substituents independently selected from alkyl, halogen and trifluoromethyl.

Further preferred are those compounds of formula I, wherein R⁴ is oxetanyl or oxetanyl substituted with alkyl.

Particularly preferred are those compounds of formula I, wherein R⁴ is cyclopropyl, phenylcyclopropyl, phenylcyclobutyl, adamantyl, phenyl, indolyl, pyrazolyl or thiazolyl, wherein phenylcyclopropyl, phenylcyclobutyl, phenyl, indolyl, pyrazolyl and thiazolyl are optionally substituted with one to three substituents independently selected from alkyl, alkoxy, halogen, trifluormethyl, phenyl and phenyl substituted with one to three substituents independently selected from alkyl, halogen and trifluoromethyl.

Other preferred compounds according to formula I are those, wherein R² is cycloalkyl. Particularly preferred are those compounds of formula I, wherein R2 is cyclopropyl.

Further preferred are compounds of formula I, wherein R¹ is cycloalkyl, preferably cyclopropyl.

Preferred are compounds of formula I, wherein R¹ and R² together with the carbon atoms $C^a$ and $C^b$ to which they are attached form

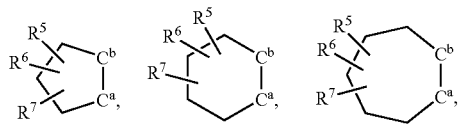

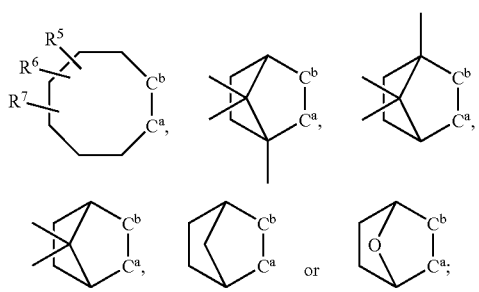

Further preferred are compounds of formula I, wherein R¹ and R² together with the carbon atoms $C^a$ and $C^b$ to which they are attached form

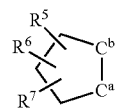

have the following formula (Ia)

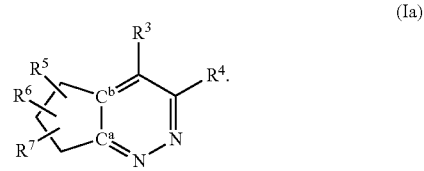

Also preferred are compounds of formula I, wherein R¹ and R² together with the carbon atoms $C^a$ and $C^b$ to which they are attached form

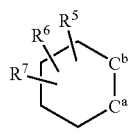

have the following formula (Ib)

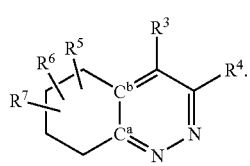

Preferred are compounds of formula I, wherein R¹ and R² together with the carbon atoms $C^a$ and $C^b$ to which they are attached form

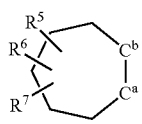

have the following formula (Ic)

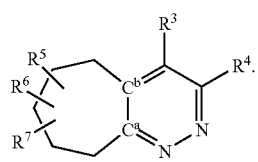

Further preferred are compounds of formula I, wherein $R^1$ and $R^2$ together with the carbon atoms $C^a$ and $C^b$ to which they are attached form

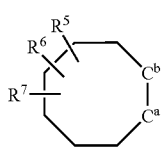

have the following formula (Id)

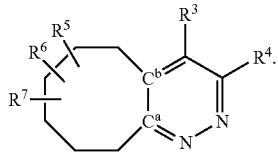

Further preferred are compounds of formula I, wherein $R^1$ and $R^2$ together with the carbon atoms $C^a$ and $C^b$ to which they are attached form

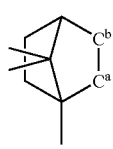

have the following formula (Ie)

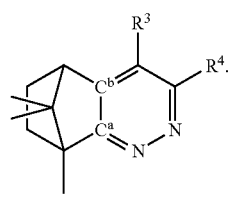

Further preferred are compounds of formula I, wherein $R^1$ and $R^2$ form together with the carbon atoms $C^a$ and $C^b$ to which they are attached

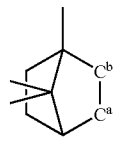

have the following formula (If)

Further preferred are compounds of formula I, wherein $R^1$ and $R^2$ form together with the carbon atoms $C^a$ and $C^b$ to which they are attached

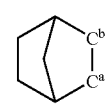

have the following formula (Ig)

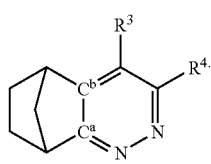

Also preferred are compounds according to formula I, wherein $R^1$ and $R^2$ form together with the carbon atoms $C^a$ and $C^b$ to which they are attached have the following formula (Ih)

Preferred are compounds of formula I, wherein $R^1$ and $R^2$ form together with the carbon atoms $C^a$ and $C^b$ to which they are attached

have the following formula

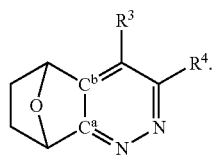
(Ii)

Particularly preferred are the compounds of formula I, wherein $R^1$ and $R^2$ together with the carbon atoms $C^a$ and $C^b$ to which they are attached form

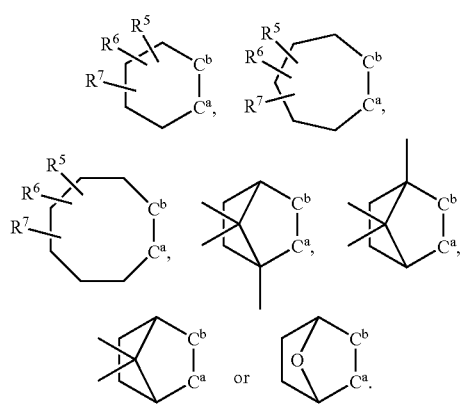

Preferred are chiral compounds of formula I.

Preferred are those compounds of formula I, wherein $R^1$ and $R^2$ together with the carbon atoms $C^a$ and $C^b$ to which they are attached form

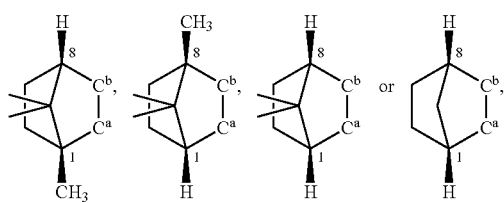

wherein the carbon atom of the 1 position is of the R configuration and the carbon atom of the 8 position is of the S configuration.

Further preferred are those compounds of formula I, wherein $R^1$ and $R^2$ together with the carbon atoms $C^a$ and $C^b$ to which they are attached form

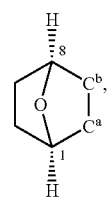

wherein the carbon atom of the 1 position is of the S configuration and the carbon atom of the 8 position is of the R configuration.

Particularly preferred are those compounds of formula I, wherein $R^1$ and $R^2$ together with the carbon atoms $C^a$ and $C^b$ to which they are attached form

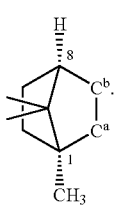

wherein the carbon atom of the 1 position are of the S configuration and the carbon atom of the 8 position is of the R configuration.

Further particularly preferred are those compounds of formula I, wherein $R^1$ and $R^2$ together with the carbon atoms $C^a$ and $C^b$ to which they are attached form wherein the carbon atom of the 1 position are of the R configuration and the carbon atom of the 8 position is of the S configuration.

Further particularly preferred are the compounds according to formula I, wherein $R^1$ and $R^2$ together with the carbon atoms $C^a$ and $C^b$ to which they are attached form According to the above formula the carbon atom of the 1 position is of the S configuration and the carbon atom of the 8 position is of the R configuration.

Another particular preferred aspect of the present invention are the compounds according to formula I, wherein $R^1$ and $R^2$ together with the carbon atoms $C^a$ and $C^b$ to which they are attached form

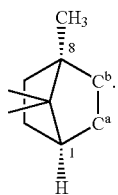

According to the above formula the carbon atom of the 1 position is of the S configuration and the carbon atom of the 8 position is of the R configuration.

Preferred are the compounds of formula I, wherein $R^5$, $R^6$ and $R^7$ are independently selected from hydrogen or alkyl. Particularly preferred are those, wherein $R^5$, $R^6$ and $R^7$ are hydrogen.

Examples of preferred compounds of formula (I) are:
1. (1S,8R)-1,11,11-Trimethyl-5-(5-methyl-1-phenyl-1H-pyrazol-4-yl)-3,4-diaza-tricyclo[6.2.1.0$^{2,7}$]undeca-2(7),3,5-triene;
2. (1S,8R)-1,11,11-Trimethyl-5-(2-trifluoromethyl-phenyl)-3,4-diazatricyclo[6.2.1.0$^{2,7}$]undeca-2(7),3,5-triene;
3. (1S,8R)-1,11,11-Trimethyl-5-(1-phenyl-5-trifluoromethyl-1H-pyrazol-4-yl)-3,4-diaza-tricyclo[6.2.1.0$^{2,7}$]undeca-2(7),3,5-triene;
4. (1S,8R)-5-Adamantan-1-yl-1,11,11-trimethyl-3,4-diazatricyclo[6.2.1.0$^{2,7}$]undeca-2,4,6-triene;
5. (1S,8R)-5-[2-(3-Chloro-phenyl)-thiazol-4-yl]-1,11,11-trimethyl-3,4-diaza-tricyclo[6.2.1.0$^{2,7}$]undeca-2,4,6-triene;
6. (1R,8S)-5-(2-Chloro-phenyl)-1,11,11-trimethyl-3,4-diaza-tricyclo[6.2.1.0$^{2,7}$]undeca-2,4,6-triene;
7. (1S,8R)-1,11,11-Trimethyl-5-phenyl-3,4-diaza-tricyclo[6.2.1.0$^{2,7}$]undeca-2,4,6-triene;
8. (1R,8S)-1,11,11-Trimethyl-5-phenyl-3,4-diaza-tricyclo[6.2.1.0$^{2,7}$]undeca-2,4,6-triene;
9. (1R,8S)-1,11,11-Trimethyl-5-(2-trifluoromethyl-phenyl)-3,4-diazatricyclo[6.2.1.0$^{2,7}$]undeca-2,4,6-triene;
10. (1R,8S)-1,11,11-Trimethyl-5-(4-trifluoromethyl-phenyl)-3,4-diazatricyclo[6.2.1.0$^{2,7}$]undeca-2,4,6-triene;
11. (1S,8R)-5-(4-Fluoro-phenyl)-1,11,11-trimethyl-3,4-diaza-tricyclo[6.2.1.0$^{2,7}$]undeca-2,4,6-triene;
12. (1S,8R)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene;
13. (1S,8R)-5-(2-Chloro-phenyl)-1,11,11-trimethyl-3,4-diaza-tricyclo[6.2.1.0$^{2,7}$]undeca-2,4,6-triene;
14. (1R,8S)-1,11,11-Trimethyl-5-(1-phenyl-5-trifluoromethyl-1H-pyrazol-4-yl)-3,4-diaza-tricyclo[6.2.1.0$^{2,7}$]undeca-2,4,6-triene;
15. (1R,8S)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene;
16. (1R,8S)-1,11,11-Trimethyl-5-(5-methyl-1-phenyl-1H-pyrazol-4-yl)-3,4-diaza-tricyclo[6.2.1.0$^{2,7}$]undeca-2,4,6-triene;
17. (1S,8R)-5-(2,4-Difluoro-phenyl)-1,11,11-trimethyl-3,4-diaza-tricyclo[6.2.1.0$^{2,7}$]undeca-2,4,6-triene;
18. (1S,8R)-5-(2-Fluoro-phenyl)-1,11,11-trimethyl-3,4-diaza-tricyclo[6.2.1.0$^{2,7}$]undeca-2,4,6-triene;
19. (1S,8R)-5-(2,5-Difluoro-phenyl)-1,11,11-trimethyl-3,4-diaza-tricyclo[6.2.1.0$^{2,7}$]undeca-2,4,6-triene;
20. (1S,8R)-1,11,11-Trimethyl-5-(1-phenyl-5-propyl-1H-pyrazol-4-yl)-3,4-diazatricyclo[6.2.1.0$^{2,7}$]undeca-2(7),3,5-triene;
21. (1S,8R)-1,11,11-Trimethyl-5-(1-methyl-1H-indol-3-yl)-3,4-diaza-tricyclo[6.2.1.0$^{2,7}$]undeca-2(7),3,5-triene;
22. (1S,8R)-5-[1-(4-Chloro-phenyl)-cyclopropyl]-1,11,11-trimethyl-3,4-diaza-tricyclo[6.2.1.0$^{2,7}$]undeca-2,4,6-triene;
23. (1S,8R)-5-[1-(4-Chloro-phenyl)-cyclobutyl]-1,11,11-trimethyl-3,4-diaza-tricyclo[6.2.1.0$^{2,7}$]undeca-2,4,6-triene;
24. 3-Adamantan-1-yl-5,6,7,8-tetrahydro-cinnoline;
25. 3-(1-Phenyl-5-trifluoromethyl-1H-pyrazol-4-yl)-5,6,7,8-tetrahydro-cinnoline;
26. 3-[1-(4-Chloro-phenyl)-cyclopropyl]-5,6,7,8-tetrahydro-cinnoline;
27. 3-[1-(4-Chloro-phenyl)-cyclobutyl]-5,6,7,8-tetrahydro-cinnoline;
28. 3-(2-Trifluoromethyl-phenyl)-6,7,8,9-tetrahydro-5H-cyclohepta[c]pyridazine;
29. 3-[1-(4-Chloro-phenyl)-5-trifluoromethyl-1H-pyrazol-4-yl]-6,7,8,9-tetrahydro-5H-cyclohepta[c]pyridazine;
30. 3-[1-(4-Chloro-phenyl)-cyclopropyl]-6,7,8,9-tetrahydro-5H-cyclohepta[c]pyridazine;
31. 3-[1-(4-Chloro-phenyl)-cyclobutyl]-6,7,8,9-tetrahydro-5H-cyclohepta[c]pyridazine;
32. 3-(5-Fluoro-2-trifluoromethyl-phenyl)-6,7,8,9-tetrahydro-5H-cyclohepta[c]pyridazine;
33. (1S,8R)-5-[1-(4-Fluoro-phenyl)-5-trifluoromethyl-1H-pyrazol-4-yl]-1,11,11-trimethyl-3,4-diazatricyclo[6.2.1.0$^{2,7}$]undeca-2(7),3,5-triene;
34. (1S,8R)-5-Cyclopropyl-1,11,11-trimethyl-3,4-diaza-tricyclo[6.2.1.0$^{2,7}$]undeca-2(7),3,5-triene;
35. 3,4-Dicyclopropyl-6-(5-methyl-1-phenyl-1H-pyrazol-4-yl)-pyridazine;
36. 3,4-Dicyclopropyl-6-(2-trifluoromethyl-phenyl)-pyridazine;
37. 6-[1-(4-Chloro-phenyl)-cyclopropyl]-3,4-dicyclopropyl-pyridazine;
38. 6-[1-(4-Chloro-phenyl)-cyclobutyl]-3,4-dicyclopropyl-pyridazine;
39. (1SR,8RS)-5-(5-Methyl-1-phenyl-1H-pyrazol-4-yl)-3,4-diaza-tricyclo[6.2.1.0$^{2,7}$]undeca-2(7),3,5-triene;
40. (1SR,8RS)-5-(2-Trifluoromethyl-phenyl)-3,4-diaza-tricyclo[6.2.1.0$^{2,7}$]undeca-2(7),3,5-triene;
41. 3-(2-Trifluoromethyl-phenyl)-5,6,7,8,9,10-hexahydro-cycloocta[c]pyridazine;
42. (1S,8R)-5-(3-Fluoro-2-trifluoromethyl-phenyl)-1,11,11-trimethyl-3,4-diaza-tricyclo[6.2.1.0$^{2,7}$]undeca-2,4,6-triene;
43. 3-(3-Fluoro-2-trifluoromethyl-phenyl)-6,7,8,9-tetrahydro-5H-cyclohepta[c]pyridazine;
44. (1SR,8RS)-5-[1-(4-Fluoro-phenyl)-5-trifluoromethyl-1H-pyrazol-4-yl]-3,4-diaza-tricyclo[6.2.1.0$^{2,7}$]undeca-2,4,6-triene;
45. (1SR,8RS)-5-(2,4-Difluoro-phenyl)-3,4-diaza-tricyclo[6.2.1.0$^{2,7}$]undeca-2,4,6-triene;
46. (1SR,8RS)-5-(2-Fluoro-phenyl)-3,4-diaza-tricyclo[6.2.1.0$^{2,7}$]undeca-2,4,6-triene;
47. (1SR,8RS)-5-(4-Fluoro-2-trifluoromethyl-phenyl)-3,4-diaza-tricyclo[6.2.1.0$^{2,7}$]undeca-2,4,6-triene;
48. 3-(3-Trifluoromethyl-1H-pyrazol-4-yl)-5,6,7,8,9,10-hexahydro-cycloocta[c]pyridazine;
49. 3-(4-Fluoro-2-trifluoromethyl-phenyl)-5,6,7,8,9,10-hexahydro-cycloocta[c]pyridazine;
50. 3-(2-Fluoro-phenyl)-5,6,7,8,9,10-hexahydro-cycloocta[c]pyridazine;

51. (1S,8R)-5-(5-Methoxy-2-trifluoromethyl-phenyl)-1,11,11-trimethyl-3,4-diaza-tricyclo[6.2.1.0$^{2,7}$]undeca-2,4,6-triene;
52. 3-(5-Methyl-1-phenyl-1H-pyrazol-4-yl)-6,7,8,9-tetrahydro-5H-cyclohepta[c]pyridazine;
53. (1S,8R)-5-(4-Fluoro-2-trifluoromethyl-phenyl)-1,11,11-trimethyl-3,4-diaza-tricyclo[6.2.1.0$^{2,7}$]undeca-2,4,6-triene;
54. 3-(2,5-Difluoro-phenyl)-6,7,8,9-tetrahydro-5H-cyclohepta[c]pyridazine;
55. 3-[1-(4-Fluoro-phenyl)-5-trifluoromethyl-1H-pyrazol-4-yl]-6,7,8,9-tetrahydro-5H-cyclohepta[c]pyridazine;
56. 3-(2,4-Difluoro-phenyl)-6,7,8,9-tetrahydro-5H-cyclohepta[c]pyridazine;
57. 3-(2-Fluoro-phenyl)-6,7,8,9-tetrahydro-5H-cyclohepta[c]pyridazine;
58. (1S,8R)-1,11,11-Trimethyl-5-(3-trifluoromethyl-1H-pyrazol-4-yl)-3,4-diaza-tricyclo[6.2.1.0$^{2,7}$]undeca-2,4,6-triene;
59. 3-[1-(4-Chloro-phenyl)-cyclopropyl]-5,6,7,8,9,10-hexahydro-cycloocta[c]pyridazine;
60. (1S,8R)-5-(5-Butoxy-1-methyl-1H-pyrazol-4-yl)-1,11,11-trimethyl-3,4-diaza-tricyclo[6.2.1.0$^{2,7}$]undeca-2,4,6-triene;
61. 3-(1-Phenyl-5-propyl-1H-pyrazol-4-yl)-6,7,8,9-tetrahydro-5H-cyclohepta[c]pyridazine;
62. 3-[1-(4-Chloro-phenyl)-cyclobutyl]-5,6,7,8,9,10-hexahydro-cycloocta[c]pyridazine;
63. 3,4-Dicyclopropyl-6-(1-phenyl-5-propyl-1H-pyrazol-4-yl)-pyridazine;
64. 3-(4-Fluoro-2-trifluoromethyl-phenyl)-6,7,8,9-tetrahydro-5H-cyclohepta[c]pyridazine; and
65. 3-(1-Methyl-5-trifluoromethyl-1H-pyrazol-4-yl)-6,7,8,9-tetrahydro-5H-cyclohepta[c]pyridazine.

Further examples of preferred compounds of formula (I) are:
66. 3-[1-(4-Fluoro-phenyl)-5-trifluoromethyl-1H-pyrazol-4-yl]-5,6,7,8,9,10-hexahydro-cycloocta[c]pyridazine;
67. (1SR,8RS)-5-(3-Fluoro-2-trifluoromethyl-phenyl)-3,4-diaza-tricyclo[6.2.1.0$^{2,7}$]undeca-2,4,6-triene;
68. (1SR,8RS)-5-Cyclopropyl-3,4-diaza-tricyclo[6.2.1.0$^{2,7}$]undeca-2,4,6-triene;
69. (1SR,8RS)-5-(5-Fluoro-2-trifluoromethyl-phenyl)-3,4-diaza-tricyclo[6.2.1.0$^{2,7}$]undeca-2,4,6-triene;
70. (1SR,8RS)-5-(1-Methyl-3-trifluoromethyl-1H-pyrazol-4-yl)-3,4-diaza-tricyclo[6.2.1.0$^{2,7}$]undeca-2,4,6-triene;
71. (1S,8R)-5-(2-Chloro-4-fluoro-phenyl)-1,11,11-trimethyl-3,4-diaza-tricyclo[6.2.1.0$^{2,7}$]undeca-2,4,6-triene;
72. 3-(3-Fluoro-2-trifluoromethyl-phenyl)-5,6,7,8,9,10-hexahydro-cycloocta[c]pyridazine;
73. 3-(5-Fluoro-2-trifluoromethyl-phenyl)-5,6,7,8,9,10-hexahydro-cycloocta[c]pyridazine;
74. (1S,8R)-5-(2-Chloro-4-fluoro-5-methoxy-phenyl)-1,11,11-trimethyl-3,4-diaza-tricyclo[6.2.1.0$^{2,7}$]undeca-2,4,6-triene;
75. (1S,8R)-5-(2-Chloro-4,5-difluoro-phenyl)-1,11,11-trimethyl-3,4-diaza-tricyclo[6.2.1.0$^{2,7}$]undeca-2,4,6-triene;
76. 3-Cyclopropyl-5,6,7,8,9,10-hexahydro-cycloocta[c]pyridazine;
77. 3-(5-Chloro-2-trifluoromethyl-phenyl)-5,6,7,8,9,10-hexahydro-cycloocta[c]pyridazine;
78. (1SR,8RS)-5-(2-Chloro-4-fluoro-phenyl)-3,4-diaza-tricyclo[6.2.1.0$^{2,7}$]undeca-2(7),3,5-triene;
79. (1SR,8RS)-5-(5-Fluoro-2-trifluoromethyl-phenyl)-3,4-diaza-tricyclo[6.2.1.0$^{2,7}$]undeca-2(7),3,5-triene;
80. (1SR,8RS)-5-(2-Chloro-4,5-difluoro-phenyl)-3,4-diaza-tricyclo[6.2.1.0$^{2,7}$]undeca-2(7),3,5-triene;
81. 3-(1-Phenyl-5-trifluoromethyl-1H-pyrazol-4-yl)-5,6,7,8,9,10-hexahydro-cycloocta[c]pyridazine;
82. (1S,8R)-1,11,11-Trimethyl-5-(4-methyl-2-phenyl-thiazol-5-yl)-3,4-diaza-tricyclo[6.2.1.0$^{2,7}$]undeca-2,4,6-triene;
83. 3-(4-Methyl-2-phenyl-thiazol-5-yl)-5,6,7,8,9,10-hexahydro-cycloocta[c]pyridazine;
84. (1SR,8RS)-5-(2-Methoxy-phenyl)-3,4-diaza-tricyclo[6.2.1.0$^{2,7}$]undeca-2,4,6-triene;
85. (1SR,8RS)-5-o-Tolyl-3,4-diaza-tricyclo[6.2.1.0$^{2,7}$]undeca-2,4,6-triene;
86. (1S,8R)-5-(2-Methoxy-phenyl)-1,11,11-trimethyl-3,4-diaza-tricyclo[6.2.1.0$^{2,7}$]undeca-2,4,6-triene;
87. (1S,8R)-1,11,11-Trimethyl-5-o-tolyl-3,4-diaza-tricyclo[6.2.1.0$^{2,7}$]undeca-2,4,6-triene;
88. 3-(2-Methoxy-phenyl)-5,6,7,8,9,10-hexahydro-cycloocta[c]pyridazine;
89. 3-(2-Methoxy-phenyl)-6,7,8,9-tetrahydro-5H-cyclohepta[c]pyridazine;
90. 3-o-Tolyl-6,7,8,9-tetrahydro-5H-cyclohepta[c]pyridazine;
91. 3-(4-Chloro-2-methyl-phenyl)-5,6,7,8,9,10-hexahydro-cycloocta[c]pyridazine;
92. 3-(4-Chloro-2-methyl-phenyl)-6,7,8,9-tetrahydro-5H-cyclohepta[c]pyridazine;
93. (1S,8R)-5-(4-Chloro-2-methyl-phenyl)-3,4-diaza-tricyclo[6.2.1.0$^{2,7}$]undeca-2(7),3,5-triene;
94. (1S,8R)-1,11,11-Trimethyl-5-(1-methyl-1H-pyrrol-2-yl)-3,4-diaza-tricyclo[6.2.1.0$^{2,7}$]undeca-2,4,6-triene;
95. 3-(1-Methyl-1H-pyrrol-2-yl)-5,6,7,8,9,10-hexahydro-cycloocta[c]pyridazine;
96. 3-(1-Methyl-1H-pyrrol-2-yl)-6,7,8,9-tetrahydro-5H-cyclohepta[c]pyridazine;
97. (1SR,8RS)-5-(1-Methyl-1H-pyrrol-2-yl)-3,4-diaza-tricyclo[6.2.1.0$^{2,7}$]undeca-2,4,6-triene;
98. (1S,8R)-5-(4-Chloro-2-methyl-phenyl)-1,11,11-trimethyl-3,4-diaza-tricyclo[6.2.1.0$^{2,7}$]undeca-2(7),3,5-triene;
99. 3-(1-Methyl-cyclopropyl)-5,6,7,8,9,10-hexahydro-cycloocta[c]pyridazine;
100. (1SR,8RS)-5-(4-Fluoro-2-methyl-phenyl)-3,4-diaza-tricyclo[6.2.1.0$^{2,7}$]undeca-2(7),3,5-triene;
101. 6,6-Dimethyl-3-(5-methyl-1-phenyl-1H-pyrazol-4-yl)-6,7-dihydro-5H-cyclopenta[c]pyridazine;
102. (1S,8R)-5-(5-Fluoro-2-methoxy-phenyl)-1,11,11-trimethyl-3,4-diaza-tricyclo[6.2.1.0$^{2,7}$]undeca-2,4,6-triene;
103. (1SR,8RS)-5-(5-Fluoro-2-methoxy-phenyl)-3,4-diaza-tricyclo[6.2.1.0$^{2,7}$]undeca-2,4,6-triene;
104. 6,6-Dimethyl-3-(2-trifluoromethyl-phenyl)-6,7-dihydro-5H-cyclopenta[c]pyridazine;
105. (1S,8R)-5-(4-Fluoro-2-methyl-phenyl)-1,11,11-trimethyl-3,4-diaza-tricyclo[6.2.1.0$^{2,7}$]undeca-2(7),3,5-triene;
106. 3-(2-Chloro-phenyl)-6,6-dimethyl-6,7-dihydro-5H-cyclopenta[c]pyridazine;
107. 3-(2,4-Difluoro-phenyl)-6,6-dimethyl-6,7-dihydro-5H-cyclopenta[C]pyridazine;
108. (1SR,8RS)-5-(1-tert-Butyl-5-trifluoromethyl-1H-pyrazol-4-yl)-3,4-diaza-tricyclo[6.2.1.0$^{2,7}$]undeca-2,4,6-triene;
109. (1S,8R)-5-(1-tert-Butyl-5-trifluoromethyl-1H-pyrazol-4-yl)-1,11,11-trimethyl-3,4-diaza-tricyclo[6.2.1.0$^{2,7}$]undeca-2,4,6-triene;
110. (1SR,8RS)-5-(2-Trifluoromethoxy-phenyl)-3,4-diaza-tricyclo[6.2.1.0$^{2,7}$]undeca-2,4,6-triene;
111. (1S,8R)-1,11,11-Trimethyl-5-(1-methyl-cyclopropyl)-3,4-diaza-tricyclo[6.2.1.0$^{2,7}$]undeca-2,4,6-triene;
112. (1S,8R)-1,11,11-Trimethyl-5-(2-trifluoromethoxy-phenyl)-3,4-diaza-tricyclo[6.2.1.0$^{2,7}$]undeca-2,4,6-triene;

113. (1S,8R)-5-(1-tert-Butyl-5-methyl-1H-pyrazol-4-yl)-1,11,11-trimethyl-3,4-diaza-tricyclo[6.2.1.0$^{2,7}$]undeca-2,4,6-triene;
114. (1SR,8RS)-5-(1-tert-Butyl-5-methyl-1H-pyrazol-4-yl)-3,4-diaza-tricyclo[6.2.1.0$^{2,7}$]undeca-2,4,6-triene;
115. 6,6-Dimethyl-3-(2-trifluoromethoxy-phenyl)-6,7-dihydro-5H-cyclopenta[c]pyridazine;
116. 3-(1-tert-Butyl-5-trifluoromethyl-1H-pyrazol-4-yl)-6,6-dimethyl-6,7-dihydro-5H-cyclopenta[c]pyridazine;
117. (1SR,8RS)-5-(1-tert-Butyl-5-cyclopropyl-1H-pyrazol-4-yl)-3,4-diaza-tricyclo[6.2.1.0$^{2,7}$]undeca-2,4,6-triene;
118. (1S,8R)-5-(1-tert-Butyl-5-cyclopropyl-1H-pyrazol-4-yl)-1,11,11-trimethyl-3,4-diaza-tricyclo[6.2.1.0$^{2,7}$]undeca-2,4,6-triene;
119. 3-(5-Chloro-2-trifluoromethyl-phenyl)-6,6-dimethyl-6,7-dihydro-5H-cyclopenta[c]pyridazine;
120. (1S,8R)-5-(5-Cyclopropyl-1-methyl-1H-pyrazol-4-yl)-1,11,11-trimethyl-3,4-diaza-tricyclo[6.2.1.0$^{2,7}$]undeca-2,4,6-triene;
121. (1SR,8RS)-5-(5-Cyclopropyl-1-methyl-1H-pyrazol-4-yl)-3,4-diaza-tricyclo[6.2.1.0$^{2,7}$]undeca-2,4,6-triene;
122. 3-(5-Cyclopropyl-1-methyl-1H-pyrazol-4-yl)-6,6-dimethyl-6,7-dihydro-5H-cyclopenta[c]pyridazine;
123. (1S,8R)-5-Cyclobutyl-1,11,11-trimethyl-3,4-diaza-tricyclo[6.2.1.0$^{2,7}$]undeca-2,4,6-triene;
124. (1SR,8RS)-5-Cyclobutyl-3,4-diaza-tricyclo[6.2.1.0$^{2,7}$]undeca-2,4,6-triene;
125. 3-(1-tert-Butyl-5-methyl-1H-pyrazol-4-yl)-6,6-dimethyl-6,7-dihydro-5H-cyclopenta[c]pyridazine;
126. (1S,8R)-5-(1,3-Dimethyl-1H-pyrazol-4-yl)-1,11,11-trimethyl-3,4-diaza-tricyclo[6.2.1.0$^{2,7}$]undeca-2,4,6-triene;
127. (1S,8R)-1,11,11-Trimethyl-5-(1-methyl-5-trifluoromethyl-1H-pyrazol-4-yl)-3,4-diaza-tricyclo[6.2.1.0$^{2,7}$]undeca-2,4,6-triene;
128. (1S,8R)-5-(1-Benzyl-5-trifluoromethyl-1H-pyrazol-4-yl)-1,11,11-trimethyl-3,4-diaza-tricyclo[6.2.1.0$^{2,7}$]undeca-2,4,6-triene;
129. (1S,8R)-5-(1-Benzyl-5-methyl-1H-pyrazol-4-yl)-1,11,11-trimethyl-3,4-diaza-tricyclo[6.2.1.0$^{2,7}$]undeca-2,4,6-triene;
130. (1S,8R)-5-(1-Benzyl-3-methyl-1H-pyrazol-4-yl)-1,11,11-trimethyl-3,4-diaza-tricyclo[6.2.1.0$^{2,7}$]undeca-2,4,6-triene;
131. (1SR,8RS)-5-Cyclopropyl-6-methyl-3,4-diaza-tricyclo[6.2.1.0$^{2,7}$]undeca-2,4,6-triene;
132. (1S,8R)-5-Cyclopropyl-1,6,11,11-tetramethyl-3,4-diaza-tricyclo[6.2.1.0$^{2,7}$]undeca-2,4,6-triene;
133. (1S,8R)-5-(1-tert-Butyl-5-phenyl-1H-pyrazol-4-yl)-1,11,11-trimethyl-3,4-diaza-tricyclo[6.2.1.0$^{2,7}$]undeca-2,4,6-triene;
134. (1S,8R)-5-(4-Chloro-benzyl)-1,11,11-trimethyl-3,4-diaza-tricyclo[6.2.1.0$^{2,7}$]undeca-2,4,6-triene;
135. (1S,8R)-1,11,11-Trimethyl-5-(1-trifluoromethyl-cyclopropyl)-3,4-diaza-tricyclo[6.2.1.0$^{2,7}$]undeca-2,4,6-triene;
136. 3-(4-Fluoro-2-trifluoromethyl-phenyl)-6,6-dimethyl-6,7-dihydro-5H-cyclopenta[c]pyridazine;
137. (1R,8S)-5-Cyclopropyl-1,11,11-trimethyl-3,4-diaza-tricyclo[6.2.1.0$^{2,7}$]undeca-2(7),3,5-triene;
138. 3-(3-Fluoro-2-trifluoromethyl-phenyl)-6,6-dimethyl-6,7-dihydro-5H-cyclopenta[c]pyridazine;
139. (1SR,8RS)-5-(2,5-Dichloro-phenyl)-3,4-diaza-tricyclo[6.2.1.0$^{2,7}$]undeca-2(7),3,5-triene;
140. (1SR,8RS)-5-(2,3-Dimethyl-phenyl)-3,4-diaza-tricyclo[6.2.1.0$^{2,7}$]undeca-2(7),3,5-triene;
141. 3-(2,5-Dichloro-phenyl)-6,6-dimethyl-6,7-dihydro-5H-cyclopenta[c]pyridazine;
142. 3-(2,3-Dimethyl-phenyl)-6,6-dimethyl-6,7-dihydro-5H-cyclopenta[c]pyridazine;
143. (1SR,8RS)-5-(2,4-Dichloro-phenyl)-3,4-diaza-tricyclo[6.2.1.0$^{2,7}$]undeca-2(7),3,5-triene;
144. (1SR,8RS)-5-(2,3-Dichloro-phenyl)-3,4-diaza-tricyclo[6.2.1.0$^{2,7}$]undeca-2(7),3,5-triene;
145. (1SR,8RS)-5-(2,4-Dimethyl-phenyl)-3,4-diaza-tricyclo[6.2.1.0$^{2,7}$]undeca-2(7),3,5-triene;
146. (1R,8S)-5-Cyclopropyl-8,11,11-trimethyl-3,4-diaza-tricyclo[6.2.1.0$^{2,7}$]undeca-2(7),3,5-triene and
147. (1S,8R)-5-Cyclopropyl-8,11,11-trimethyl-3,4-diaza-tricyclo[6.2.1.0$^{2,7}$]undeca-2(7),3,5-triene.

Examples of particularly preferred compounds of formula (I) are:

(1S,8R)-1,11,11-Trimethyl-5-(5-methyl-1-phenyl-1H-pyrazol-4-yl)-3,4-diaza-tricyclo[6.2.1.0$^{2,7}$]undeca-2(7),3,5-triene;

(1S,8R)-1,11,11-Trimethyl-5-(2-trifluoromethyl-phenyl)-3,4-diazatricyclo[6.2.1.0$^{2,7}$]undeca-2(7),3,5-triene;

(1S,8R)-1,11,11-Trimethyl-5-(1-phenyl-5-trifluoromethyl-1H-pyrazol-4-yl)-3,4-diaza-tricyclo[6.2.1.0$^{2,7}$]undeca-2(7),3,5-triene;

(1S,8R)-1,11,11-Trimethyl-5-phenyl-3,4-diaza-tricyclo[6.2.1.0$^{2,7}$]undeca-2,4,6-triene;

(1S,8R)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene;

(1S,8R)-5-(2-Chloro-phenyl)-1,11,11-trimethyl-3,4-diaza-tricyclo[6.2.1.0$^{2,7}$]undeca-2,4,6-triene;

(1S,8R)-5-(2-Fluoro-phenyl)-1,11,11-trimethyl-3,4-diaza-tricyclo[6.2.1.0$^{2,7}$]undeca-2,4,6-triene;

(1S,8R)-1,11,11-Trimethyl-5-(1-phenyl-5-propyl-1H-pyrazol-4-yl)-3,4-diazatricyclo[6.2.1.0$^{2,7}$]undeca-2(7),3,5-triene;

(1S,8R)-5-[1-(4-Chloro-phenyl)-cyclopropyl]-1,11,11-trimethyl-3,4-diaza-tricyclo[6.2.1.0$^{2,7}$]undeca-2,4,6-triene;

(1S,8R)-5-[1-(4-Chloro-phenyl)-cyclobutyl]-1,11,11-trimethyl-3,4-diaza-tricyclo[6.2.1.0$^{2,7}$]undeca-2,4,6-triene;

3-[1-(4-Chloro-phenyl)-cyclopropyl]-5,6,7,8-tetrahydro-cinnoline;

3-[1-(4-Chloro-phenyl)-cyclobutyl]-5,6,7,8-tetrahydro-cinnoline;

3-(2-Trifluoromethyl-phenyl)-6,7,8,9-tetrahydro-5H-cyclohepta[c]pyridazine;

3-[1-(4-Chloro-phenyl)-5-trifluoromethyl-1H-pyrazol-4-yl]-6,7,8,9-tetrahydro-5H-cyclohepta[c]pyridazine;

3-(5-Fluoro-2-trifluoromethyl-phenyl)-6,7,8,9-tetrahydro-5H-cyclohepta[c]pyridazine;

(1S,8R)-5-Cyclopropyl-1,11,11-trimethyl-3,4-diaza-tricyclo[6.2.1.0$^{2,7}$]undeca-2(7),3,5-triene;

(1SR,8RS)-5-(2-Trifluoromethyl-phenyl)-3,4-diaza-tricyclo[6.2.1.0$^{2,7}$]undeca-2(7),3,5-triene;

3-(2-Trifluoromethyl-phenyl)-5,6,7,8,9,10-hexahydro-cycloocta[c]pyridazine;

3-(3-Fluoro-2-trifluoromethyl-phenyl)-6,7,8,9-tetrahydro-5H-cyclohepta[c]pyridazine;

(1SR,8RS)-5-[1-(4-Fluoro-phenyl)-5-trifluoromethyl-1H-pyrazol-4-yl]-3,4-diaza-tricyclo[6.2.1.0$^{2,7}$]undeca-2,4,6-triene;

(1SR,8RS)-5-(4-Fluoro-2-trifluoromethyl-phenyl)-3,4-diaza-tricyclo[6.2.1.0$^{2,7}$]undeca-2,4,6-triene;

3-(4-Fluoro-2-trifluoromethyl-phenyl)-5,6,7,8,9,10-hexahydro-cycloocta[c]pyridazine;

(1S,8R)-5-(4-Fluoro-2-trifluoromethyl-phenyl)-1,11,11-trimethyl-3,4-diaza-tricyclo[6.2.1.0$^{2,7}$]undeca-2,4,6-triene;

3-(4-Fluoro-2-trifluoromethyl-phenyl)-6,7,8,9-tetrahydro-5H-cyclohepta[c]pyridazine; and 3-(1-Methyl-5-trifluoromethyl-1H-pyrazol-4-yl)-6,7,8,9-tetrahydro-5H-cyclohepta[c]pyridazine.

Further particularly preferred compounds of formula (I) are (1S,8R)-5-Cyclopropyl-1,11,11-trimethyl-3,4-diaza-tricyclo[6.2.1.0$^{2,7}$]undeca-2(7),3,5-triene;

(1SR,8RS)-5-(2-Trifluoromethyl-phenyl)-3,4-diaza-tricyclo[6.2.1.0$^{2,7}$]undeca-2(7),3,5-triene;

3-(2-Trifluoromethyl-phenyl)-5,6,7,8,9,10-hexahydro-cycloocta[c]pyridazine;

(1SR,8RS)-5-(5-Chloro-2-trifluoromethyl-phenyl)-3,4-diaza-tricyclo[6.2.1.0$^{2,7}$]undeca-2(7),3,5-triene;

(1S,8R)-1,11,11-Trimethyl-5-(1-methyl-cyclopropyl)-3,4-diaza-tricyclo[6.2.1.0$^{2,7}$]undeca-2,4,6-triene;

(1S,8R)-5-Cyclopropyl-1,6,11,11-tetramethyl-3,4-diaza-tricyclo[6.2.1.0$^{2,7}$]undeca-2,4,6-triene;

(1S,8R)-1,11,11-Trimethyl-5-(1-trifluoromethyl-cyclopropyl)-3,4-diaza-tricyclo[6.2.1.0$^{2,7}$]undeca-2,4,6-triene;

3-(4-Fluoro-2-trifluoromethyl-phenyl)-6,6-dimethyl-6,7-dihydro-5H-cyclopenta[c]pyridazine and (1R,8S)-5-Cyclopropyl-1,11,11-trimethyl-3,4-diaza-tricyclo[6.2.1.0$^{2,7}$]undeca-2(7),3,5-triene.

Processes for the manufacture of compounds of formula I are an object of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

In general, compounds of type I are readily accessible by treatment of compounds of formula II with hydrazine: different reaction conditions can be used to perform the condensation reaction, e.g.: heating II with hydrazine monohydrate in toluene in the presence of an acid such as p-toluene sulfonic acid, (ii) heating II and hydrazine monohydrate in a mixture of water/acetic acid at reflux temperature, (iii) heating II and hydrazine monohydrate in a mixture of water/acetic acid at reflux temperature which is then followed, after work-up, by a basic treatment with NaOMe in n-butanol at reflux temperature to complete the ring closing reaction to pyridazine.

The application of the different conditions depends on the respective starting materials used and is outlined in the experimental part. The geometries of the double bond of compounds of type II can be E or Z, or mixtures of E and Z. Independent of the double bond geometry, they can be converted to I by choosing the most appropriate reaction conditions outlined above, and as exemplified in the experimental part.

In cases were R1 and R2 form 5 to 8 membered rings, the synthesis of these analogues of formula II via a Horner-Wittig reaction (chapter below) can give rise to isomeric compounds, with the double bond migrated into the ring system, and as exemplified in formula IIa for the 7 membered ring system. Also these isomers can be directly converted to II by employing the reaction conditions outlined above.

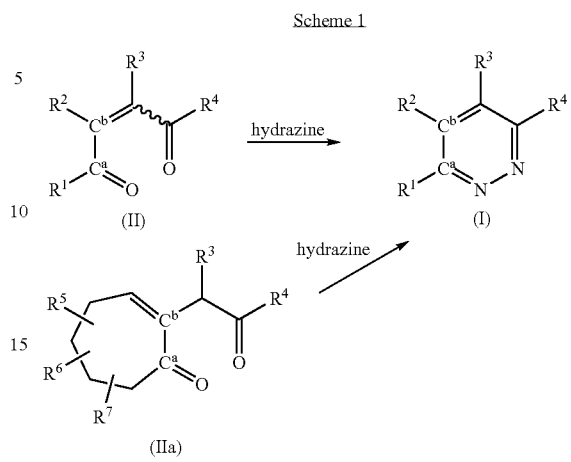

Scheme 1

The compound of type II, employed in scheme 1 as starting materials, can be prepared as summarized in scheme 2:

Thus, on reacting a 1,2-diketone of formula III with a phosphonate of formula IV in a Horner-Emmons (or Wittig-Horner) reaction, this gives rise to compounds of formula II. The conditions that can be used are, e.g.: potassium tert-butoxide as a base in tert-butanol as solvent under reflux conditions. Depending on the starting material, double bond migration can occur were possible, as shown in formula IIa for compounds were R1, R2 form a 7 membered ring, and as exemplified in the experimental part.

The double bond geometries of the compounds of formula II can be E, Z or a mixture of E and Z depending on the R1, R2; R3, R4 groups. In many cases only one isomer (the thermodynamically more stable E isomer) is predominantly formed. In cases were mixtures are obtained these can be separated by chromatography or used as mixtures in the ring forming reaction. The stereochemistry of the double bond can be assigned by NMR for the compounds of formula II (experimental part). Instead of a phosphonate of type IV it is also possible to use a corresponding alpha-halo ketone analogue and performing a Reformatsky reaction followed by water elimination (for an example of this type of reaction: Huang, J. Chem. Soc., Perkin Trans. 1, 1989, 2397).

For compounds of formula III that are not symmetric, compounds of formula II are directly obtained in cases where the Cb carbonyl group is more reactive then Ca carbonyl. In cases were the two carbonyl groups are similar, mixtures can be obtained, which can be separated by chromatography and processed further accordingly.

In cases were the Ca carbonyl group is the more reactive in regard to the Horner-Emmons (or Wittig-Horner) reaction—compounds of formula II can be obtained via several routes, e.g.: (i) conversion of the Ca carbonyl into a cyclic ketal group on reaction with, for example, ethane-1,2-diol (analogues to: Boeckman, J. Am. Chem. Soc., 1986, 5549), performing the Wittig-Horner reaction at Cb followed by Ca ketal cleavage; or alternatively: (ii) reduction of the Ca carbonyl group to hydroxy and protection, for example, as a t-butyl-dimethyl-silyl ether (for an example: Boeckman, J. Am. Chem. Soc., 1986, 5549), performing then the Horner-Wittig reaction at Cb, de-protection and final oxidation of hydroxy back to carbonyl—using, for example, the Swern oxidation conditions (for an example of the reaction: Albright, J. Org. Chem., 1965 30, 1107).

Scheme 2

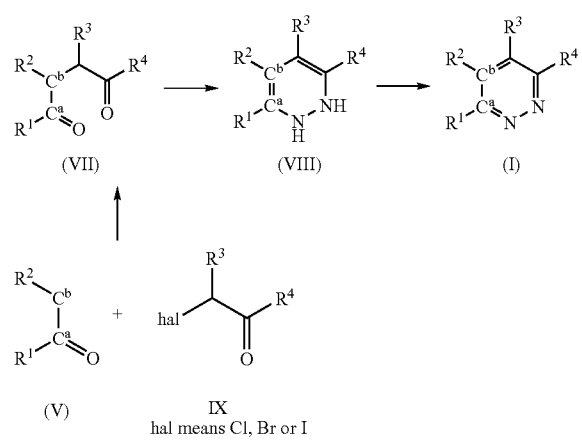

Alkyl; Me or Ethyl

The 1,2-diketones III used in scheme II are either commercial, known in the literature or can be prepared by combination of methods known in the art.

The phosphonates of formula IV are either known in the literature or can be prepared by standard procedures. An example of preparing compounds IV typically involves treatment of an alkyl-phosponic acid dimethyl ester with a base such as N-butyllithium, in THF as solvent at −78° C. and subsequent reaction with an alkyl carboxylate to give IV. Alternatively, methyl-phosphonic acid dimethyl ester (R3═H) can be used in the reaction, with a subsequent alkylation step to introduce R3—reacting IV (R═H) with an alkylating reagent (R3-hal) in the presence of a base such as potassium t-butoxide or N-butyllithium or potassium carbonate (for an analogous reaction: B. Kirschberger, Synthesis, 1986, 11, 926).

Alternative ways to prepare compounds of formula II typically involves reacting a ketone of formula V with compounds of formula VI according to Scheme 3. The reaction can be achieved in analogy to a method described by Mukaiyama (J. Am. Chem. Soc., 1974, 96, 7503) via a cross aldol reaction, reacting V, via its pre-formed silyl enol-ether, with a formyl carbonyl of formula IV, in the presence of titanium tetrachloride, to give II after dehydration of the primary coupling product. Compounds VI are either commercial available or prepared in analogy to methods described in the literature, e.g. from corresponding methyl ketones and SeO$_2$ oxidation (for a literature example: K. C. Joshi, Heterocycles, 1981, 16, 1545), or from alpha-halo ketones and Swern oxidation (for an example; D. Swern, Synthesis, 1981, 165).

Scheme 3

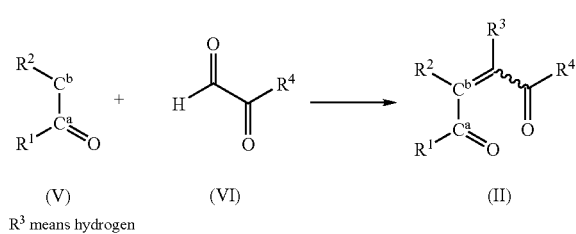

R$^3$ means hydrogen

The compounds of formula V are either commercially available, described in the literature or can be prepared by applying known procedures.

A further alternative way to prepare compounds of formula I is outlined in scheme 4 and involves reacting 1,4-diketones of formula VII with hydrazine under conditions discussed above to give the dihydropyridazines of formula VIII (one of several possible isomeric forms drawn). These can then be aromatized with, for example, Pd on charcoal or another oxidation reagent such as Br$_2$ (for analogues procedures: Baumgarten, J. Am. Chem. Soc. 1958, 80, 6609) to give compounds of formula I. The 1,4 diketones of formula VII are widely used synthetic building blocks and numerous methods for their preparation are known in the literature (for example: Corey J. Am. Chem. Soc. 1969, 91, 4926; Katritzky, J. Org. Chem. 1991, 56, 6917). A more recent example to prepare these compounds is to use the procedure published by A. Baba (J. Org. Chem, 1997, 62, 8282) and reacting ketone V, via prior conversion to the corresponding tin enolate, with the alpha-halo ketone IX in the presence of catalytic amounts of ZnCl$_2$ (Scheme 4).

Scheme 4 hal means Cl, Br or I

A preferred process for the preparation of a compound of formula (I)

comprises the reaction of a compound according to formula (II)

with hydrazine in order to obtain a compound according to formula I;

wherein $R^1$ to $R^4$ are defined as before.

Preferred intermediates are:

[2-(5-Methyl-1-phenyl-1H-pyrazol-4-yl)-2-oxo-ethyl]-phosphonic acid dimethyl ester;
(1S,4R)-1,7,7-Trimethyl-3-[2-(5-methyl-1-phenyl-1H-pyrazol-4-yl)-2-oxo-eth-(E)-ylidene]-bicyclo[2.2.1]heptan-2-one;
2-Oxo-2-(2-trifluoromethyl-phenyl)-ethyl]-phosphonic acid dimethyl ester;
(1S,4R)-1,7,7-Trimethyl-3-[2-oxo-2-(2-trifluoromethyl-phenyl)-eth-(E)-ylidene]-bicyclo[2.2.1]heptan-2-one;
[2-Oxo-2-(1-phenyl-5-trifluoromethyl-1H-pyrazol-4-yl)-ethyl]-phosphonic acid dimethyl ester;
(1S,4R)-1,7,7-Trimethyl-3-[2-oxo-2-(1-phenyl-5-trifluoromethyl-1H-pyrazol-4-yl)-eth-(E)-ylidene]-bicyclo[2.2.1]heptan-2-one;
2-Adamantan-1-yl-2-oxo-ethyl)-phosphonic acid dimethyl ester;
(1S,4R)-3-[2-Adamantan-1-yl-2-oxo-eth-(E)-ylidene]-1,7,7-trimethyl-bicyclo[2.2.1]heptan-2-one;
{2-[2-(3-Chloro-phenyl)-thiazol-4-yl]-2-oxo-ethyl}-phosphonic acid dimethyl ester;
(1S,4R)-3-[2-[2-(3-Chloro-phenyl)-thiazol-4-yl]-2-oxo-eth-(E)-ylidene]-1,7,7-trimethyl-bicyclo[2.2.1]heptan-2-one;
[2-(2-Chloro-phenyl)-2-oxo-ethyl]-phosphonic acid dimethyl ester;
(1R,4S)-3-[2-(2-Chloro-phenyl)-2-oxo-eth-(E)-ylidene]-1,7,7-trimethyl-bicyclo[2.2.1]heptan-2-one;
(1S,4R)-1,7,7-Trimethyl-3-[2-oxo-2-phenyl-eth-(E)-ylidene]-bicyclo[2.2.1]heptan-2-one and
(1S,4R)-1,7,7-trimethyl-3-[2-oxo-2-phenyl-eth-(Z)-ylidene]-bicyclo[2.2.1]heptan-2-one;
(1R,4S)-1,7,7-Trimethyl-3-[2-oxo-2-phenyl-eth-(E)-ylidene]-bicyclo[2.2.1]heptan-2-one and
(1R,4S)-1,7,7-Trimethyl-3-[2-oxo-2-phenyl-eth-(Z)-ylidene]-bicyclo[2.2.1]heptan-2-one;
(1R,4S)-1,7,7-Trimethyl-3-[2-oxo-2-(2-trifluoromethyl-phenyl)-eth-(E)-ylidene]-bicyclo[2.2.1]heptan-2-one;
(1R,4S)-1,7,7-Trimethyl-3-[2-oxo-2-(4-trifluoromethyl-phenyl)-eth-(E)-ylidene]-bicyclo[2.2.1]heptan-2-one;
[2-(4-Fluoro-phenyl)-2-oxo-ethyl]-phosphonic acid dimethyl ester;
(1S,4R)-3-[2-(4-Fluoro-phenyl)-2-oxo-eth-(E)-ylidene]-1,7,7-trimethyl-bicyclo[2.2.1]heptan-2-one;
{2-[1-(4-Chloro-phenyl)-5-trifluoromethyl-1H-pyrazol-4-yl]-2-oxo-ethyl}-phosphonic acid dimethyl ester;
(1S,4R)-3-{2-[1-(4-chloro-phenyl)-5-trifluoromethyl-1H-pyrazol-4-yl]-2-oxo-eth-(E)-ylidene}-1,7,7-trimethyl-bicyclo[2.2.1]heptan-2-one;
(1S,4R)-3-[2-(2-Chloro-phenyl)-2-oxo-eth-(E)-ylidene]-1,7,7-trimethyl-bicyclo[2.2.1]heptan-2-one;
(1R,4S)-1,7,7-Trimethyl-3-[2-oxo-2-(1-phenyl-5-trifluoromethyl-1H-pyrazol-4-yl)-eth-(E)-ylidene]-bicyclo[2.2.1]heptan-2-one;
(1R,4S)-3-{2-[1-(4-Chloro-phenyl)-5-trifluoromethyl-1H-pyrazol-4-yl]-2-oxo-eth-(E)-ylidene}-1,7,7-trimethyl-bicyclo[2.2.1]heptan-2-one;
(1R,4S)-1,7,7-Trimethyl-3-[2-(5-methyl-1-phenyl-1H-pyrazol-4-yl)-2-oxo-eth-(E)-ylidene]-bicyclo[2.2.1]heptan-2-one;
[2-(2,4-Difluoro-phenyl)-2-oxo-ethyl]-phosphonic acid dimethyl ester;
(1S,4R)-3-[2-(2,4-difluoro-phenyl)-2-oxo-eth-(E)-ylidene]-1,7,7-trimethyl-bicyclo[2.2.1]heptan-2-one;

[2-(2-Fluoro-phenyl)-2-oxo-ethyl]-phosphonic acid dimethyl ester;
(1S,4R)-3-[2-(2-Fluoro-phenyl)-2-oxo-eth-(E)-ylidene]-1,7,7-trimethyl-bicyclo[2.2.1]heptan-2-one;
[2-(2,5-Difluoro-phenyl)-2-oxo-ethyl]-phosphonic acid dimethyl ester;
(1S,4R)-3-[2-(2,5-Difluoro-phenyl)-2-oxo-eth-(E)-ylidene]-1,7,7-trimethyl-bicyclo[2.2.1]heptan-2-one;
[2-Oxo-2-(1-phenyl-5-propyl-1H-pyrazol-4-yl)-ethyl]-phosphonic acid dimethyl ester;
(1S,4R)-1,7,7-Trimethyl-3-[2-oxo-2-(1-phenyl-5-propyl-1H-pyrazol-4-yl)-eth-(E)-ylidene]-bicyclo[2.2.1]heptan-2-one;
[2-(1-Methyl-1H-indol-3-yl)-2-oxo-ethyl]-phosphonic acid dimethyl ester;
(1S,4R)-1,7,7-Trimethyl-3-[2-(1-methyl-1H-indol-3-yl)-2-oxo-eth-(E)-ylidene]-bicyclo[2.2.1]heptan-2-one and (1S,4R)-1,7,7-Trimethyl-3-[2-(1-methyl-1H-indol-3-yl)-2-oxo-eth-(Z)-ylidene]-bicyclo[2.2.1]heptan-2-one;
{2-[1-(4-Chloro-phenyl)-cyclopropyl]-2-oxo-ethyl}-phosphonic acid dimethyl ester;
(1S,4R)-3-[2-[1-(4-chloro-phenyl)-cyclopropyl]-2-oxo-eth-(E)-ylidene]-1,7,7-trimethyl-bicyclo[2.2.1]heptan-2-one;
{2-[1-(4-Chloro-phenyl)-cyclobutyl]-2-oxo-ethyl}-phosphonic acid dimethyl ester;
(1S,4R)-3-[2-[1-(4-Chloro-phenyl)-cyclobutyl]-2-oxo-eth-(E)-ylidene]-1,7,7-trimethyl-bicyclo[2.2.1]heptan-2-one;
2-[2-Adamantan-1-yl-2-oxo-eth-(E)-ylidene]-cyclohexanone;
2-[2-Oxo-2-(1-phenyl-5-trifluoromethyl-1H-pyrazol-4-yl)-eth-(E)-ylidene]-cyclohexanone;
2-{2-[1-(4-Chloro-phenyl)-cyclopropyl]-2-oxo-ethyl}-cyclohex-2-enone;
2-{2-[1-(4-Chloro-phenyl)-cyclobutyl]-2-oxo-ethyl}-cyclohex-2-enone;
2-[2-Oxo-2-(2-trifluoromethyl-phenyl)-ethyl]-cyclohept-2-enone;
2-{2-[1-(4-Chloro-phenyl)-5-trifluoromethyl-1H-pyrazol-4-yl]-2-oxo-ethyl}-cyclohept-2-enone;
2-{2-[1-(4-Chloro-phenyl)-cyclopropyl]-2-oxo-ethyl}-cyclohept-2-enone;
2-{2-[1-(4-Chloro-phenyl)-cyclobutyl]-2-oxo-ethyl}-cyclohept-2-enone;
[2-(5-Fluoro-2-trifluoromethyl-phenyl)-2-oxo-ethyl]-phosphonic acid dimethyl ester;
2-[2-(5-Fluoro-2-trifluoromethyl-phenyl)-2-oxo-ethyl]-cyclohept-2-enone;
{2-[1-(4-Fluoro-phenyl)-5-trifluoromethyl-1H-pyrazol-4-yl]-2-oxo-ethyl}-phosphonic acid dimethyl ester;
(1S,4R)-3-{2-[1-(4-Fluoro-phenyl)-5-trifluoromethyl-1H-pyrazol-4-yl]-2-oxo-eth-(E)-ylidene}-1,7,7-trimethyl-bicyclo[2.2.1]heptan-2-one;
(2-Cyclopropyl-2-oxo-ethyl)-phosphonic acid dimethyl ester;
(1S,4R)-3-[2-Cyclopropyl-2-oxo-eth-(E)-ylidene]-1,7,7-trimethyl-bicyclo[2.2.1]heptan-2-one;
(E or Z)-1,2-Dicyclopropyl-4-(5-methyl-1-phenyl-1H-pyrazol-4-yl)-but-2-ene-1,4-dione;
(Z/E)-1,2-Dicyclopropyl-4-(2-trifluoromethyl-phenyl)-but-2-ene-1,4-dione;
(E/Z)-4-[1-(4-Chloro-phenyl)-cyclopropyl]-1,2-dicyclopropyl-but-2-ene-1,4-dione;
(Z/E)-4-[1-(4-Chloro-phenyl)-cyclobutyl]-1,2-dicyclopropyl-but-2-ene-1,4-dione;
(1SR,4RS)-3-[2-(5-Methyl-1-phenyl-1H-pyrazol-4-yl)-2-oxo-eth-(E)-ylidene]-bicyclo[2.2.1]heptan-2-one;

(E or Z)-(1SR,4RS)-3-[2-Oxo-2-(2-trifluoromethyl-phenyl)-ethylidene]-bicyclo[2.2.1]heptan-2-one;
2-[2-Oxo-2-(2-trifluoromethyl-phenyl)-ethyl]-cyclooct-2-enone;
[2-(3-Fluoro-2-trifluoromethyl-phenyl)-2-oxo-ethyl]-phosphonic acid dimethyl ester;
(1S,4R)-3-[2-(3-Fluoro-2-trifluoromethyl-phenyl)-2-oxo-eth-(E)-ylidene]-1,7,7-trimethyl-bicyclo[2.2.1]heptan-2-one;
2-[2-(3-Fluoro-2-trifluoromethyl-phenyl)-2-oxo-ethyl]-cyclohept-2-enone;
(1S,4R)-3-[2-[1-(4-Fluoro-phenyl)-5-trifluoromethyl-1H-pyrazol-4-yl]-2-oxo-eth-(E)-ylidene]-bicyclo[2.2.1]heptan-2-one;
(1SR,4RS)-3-[2-(2,4-Difluoro-phenyl)-2-oxo-eth-(E)-ylidene]-bicyclo[2.2.1]heptan-2-one;
(1SR,4RS)-3-[2-(2-fluoro-phenyl)-2-oxo-eth-(E)-ylidene]-bicyclo[2.2.1]heptan-2-one;
[2-(4-Fluoro-2-trifluoromethyl-phenyl)-2-oxo-ethyl]-phosphonic acid dimethyl ester;
(1SR,4RS)-3-[2-(4-Fluoro-2-trifluoromethyl-phenyl)-2-oxo-eth-(E)-ylidene]-bicyclo[2.2.1]heptan-2-one;
[2-Oxo-2-(3-trifluoromethyl-1H-pyrazol-4-yl)-ethyl]-phosphonic acid dimethyl ester;
(Z)-2-[2-Oxo-2-(3-trifluoromethyl-1H-pyrazol-4-yl)-ethyl]-cyclooct-2-enone;
(Z)-2-[2-(4-Fluoro-2-trifluoromethyl-phenyl)-2-oxo-ethyl]-cyclooct-2-enone;
(Z)-2-[2-(2-Fluoro-phenyl)-2-oxo-ethyl]-cyclooct-2-enone;
(1S,4R)-3-[2-(5-Fluoro-2-trifluoromethyl-phenyl)-2-oxo-eth-(E)-ylidene]-1,7,7-trimethyl-bicyclo[2.2.1]heptan-2-one;
2-[2-(5-Methyl-1-phenyl-1H-pyrazol-4-yl)-2-oxo-ethyl]-cyclohept-2-enone;
(1S,4R)-3-[2-(4-Fluoro-2-trifluoromethyl-phenyl)-2-oxo-eth-(E)-ylidene]-1,7,7-trimethyl-bicycio[2.2.1]heptan-2-one;
2-[2-(2,5-Difluoro-phenyl)-2-oxo-ethyl]-cyclohept-2-enone;
2-{2-[1-(4-Fluoro-phenyl)-5-trifluoromethyl-1H-pyrazol-4-yl]-2-oxo-ethyl}-cyclohept-2-enone;
2-[2-(2,4-Difluoro-phenyl)-2-oxo-ethyl]-cyclohept-2-enone;
2-[2-(2-Fluoro-phenyl)-2-oxo-ethyl]-cyclohept-2-enone;
(1S,4R)-1,7,7-Trimethyl-3-[2-oxo-2-(3-trifluoromethyl-1H-pyrazol-4-yl)-eth-E-ylidene]-bicyclo[2.2.1]heptan-2-one;
(Z)-2-{2-[1-(4-Chloro-phenyl)-cyclopropyl]-2-oxo-ethyl}-cyclooct-2-enone;
[2-(5-Chloro-1-methyl-1H-pyrazol-4-yl)-2-oxo-ethyl]-phosphonic acid dimethyl ester;
(1S,4R)-3-[2-(5-Chloro-1-methyl-1H-pyrazol-4-yl)-2-oxo-eth-(E)-ylidene]-1,7,7-trimethyl-bicyclo[2.2.1]heptan-2-one;
2-[2-Oxo-2-(1-phenyl-5-propyl-1H-pyrazol-4-yl)-ethyl]-cyclohept-2-enone;
(Z)-2-{2-[1-(4-Chloro-phenyl)-cyclobutyl]-2-oxo-ethyl}-cyclooct-2-enone;
(E or Z)-1,2-Dicyclopropyl-4-(1-phenyl-5-propyl-1H-pyrazol-4-yl)-but-2-ene-1,4-dione;
2-[2-(4-Fluoro-2-trifluoromethyl-phenyl)-2-oxo-ethyl]-cyclohept-2-enone;
[2-(1-Methyl-5-trifluoromethyl-1H-pyrazol-4-yl)-2-oxo-ethyl]-phosphonic acid dimethyl ester and
2-[2-(1-Methyl-5-trifluoromethyl-1H-pyrazol-4-yl)-2-oxo-ethyl]-cyclohept-2-enone.

Assay Procedures

Transient Expression and Partial Purification:

The cDNA encoding the human 11beta-HSD1 protein was cloned into the expression vector pcDNA3 (Stratagene). This construct (for details see Alex Odermatt et al.; J Biol. Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phosphate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated wit a tip sonicator (10% output; 2×30 sec.) and cleared by a low speed centrifugation (10 min×9000 g; 4° C.). The microsomal fraction was collected by a high speed centrifugation (60 min×110'000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there IC50 values, e.g. the concentration at which the production of cortisol was 50% reduced.

In this test preferred compounds as described above have IC50 values below 1000 nM; more preferred compounds have IC50 values below 100 nM. Most preferred compounds have IC50 values below 10 nM.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% CO2 atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound | 11-beta-HSD 1 IC$_{50}$ (nM) |
|---|---|
| Example 1 | 30 |
| Example 41 | 3 |

Compounds as described above have IC$_{50}$ values below 1000 nM; preferred compounds have IC$_{50}$ values below 100 nM. More preferred compounds have IC$_{50}$ values below 10 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

(1S,8R)-1,11,11-Trimethyl-5-(5-methyl-1-phenyl-1H-pyrazol-4-yl)-3,4-diaza-tricyclo[6.2.1.0$^{2,7}$]undeca-2(7),3,5-triene Step A]: [2-(5-Methyl-1-phenyl-1H-pyrazol-4-yl)-2-oxo-ethyl]-phosphonic acid dimethyl ester A solution of methyl-phosphonic acid dimethyl ester (2.1 g) in THF (20 mL) under an argon atmosphere was cooled to −78° C. and treated dropwise with 10.98 mL of a 1.6 M solution of N-butyllithium in hexane keeping the temperature of the reaction mixture below −65° C. After stirring for 15 minutes 5-methyl-1-phenyl-1H-pyrazole-4-carboxylic acid methyl ester (1.9 g in 2 ml THF) were added slowly and the mixture was stirred for 30 minutes (temperature below −65° C.). The reaction mixture was allowed to warm to 0° C., quenched with 1N aqueous HCl, and then partitioned between ACOEt and water. The layers were separated, the organic layer was washed with water, dried over MgSO$_4$, filtered and evaporated to give [2-(5-Methyl-1-phenyl-1H-pyrazol-4-yl)-2-oxo-ethyl]-phosphonic acid dimethyl ester (2.34 g) as a dark brown oil that was used in the next reaction without further purification. MS (ESI): 309.1 (MH$^+$).

Step B]: (1S,4R)-1,7,7-Trimethyl-3-[2-(5-methyl-1-phenyl-1H-pyrazol-4-yl)-2-oxo-eth-(E)-ylidene]-bicyclo[2.2.1]heptan-2-one)

[2-(5-Methyl-1-phenyl-1H-pyrazol-4-yl)-2-oxo-ethyl]-phosphonic acid dimethyl ester (1.1 g) in tert-butanol (60 mL) at RT under an argon atmosphere was treated with potassium tert-butoxide (0.412 g) and the mixture was stirred for 30 minutes. Then (1S,4R)-1,7,7-trimethyl-bicyclo[2.2.1]heptane-2,3-dione (0.499 g) was added at RT and the mixture was heated at reflux for 12 h under an argon atmosphere. The reaction mixture was partitioned between water and AcOEt, the layers were separated, the aqueous layer extracted twice with AcOEt. The combined organic layers were washed with water, dried over Na$_2$SO$_4$, filtered and evaporated. The residue was purified by flash chromatography (heptane/AcOEt 100% to 80%) to give (1S,4R)-1,7,7-trimethyl-3-[2-(5-methyl-1-phenyl-1H-pyrazol-4-yl)-2-oxo-eth-(E)-ylidene]-bicyclo[2.2.1]heptan-2-one (0.78 g) as a light yellow solid. MS (EI): 348.2 (M$^+$).

Step C]: (1S,8R)-1,11,11-Trimethyl-5-(5-methyl-1-phenyl-1H-pyrazol-4-yl)-3,4-diaza-tricylo[6.2.1.0$^{2,7}$]undeca-2(7),3,5-triene A solution of (1S,4R)-1,7,7-Trimethyl-3-[2-(5-methyl-1-phenyl-1H-pyrazol-4-yl)-2-oxo-eth-(E)-ylidene]-bicyclo [2.2.1]heptan-2-one (0.78 g) in ethanol (60 ml) was treated at RT with water (10 ml), hydrazine monohydrate (1.09 ml) and acetic acid (10 ml), and the mixture was then heated to reflux for 20 h (oil bath temperature: 105° C.). The reaction mixture was partitioned between water and AcOEt. The combined organic layers were washed with 2M aqueous KHCO$_3$, dried over Na$_2$SO$_4$, filtered and evaporated. The residue obtained was composed of a 2:1 mixture of hydrazone intermediate [MS (EI): 362.2 (M$^+$)] and desired ring-closed pyridazine [MS (EI): 344.2 (M$^+$)], together with some impurities. At this level the desired product could be separated by chromatography, but higher yields were obtained by subjecting the mixture to a ring-closing procedure as follows:

The mixture was first subjected to flash chromatography (heptane/AcOEt 100% to 75%) to remove impurities, and the white foam obtained (0.556 g) was dissolved in n-butanol (20 mL), treated at RT with 0.56 mL of a 5.4 M solution of NaOMe in MeOH and heated to reflux for 12 h (until according to TLC and MS analysis all hydrazone intermediate was ring-closed to the desired pyridazine). The residue was partitioned between AcOEt and brine, the layers were separated and the organic layer washed with 1M aqueous HCL, then 2M aqueous KHCO$_3$, dried over Na$_2$SO$_4$, filtered and evaporated. The residue was purified by flash chromatography (heptane/AcOEt 100% to 70%) and the material obtained crystallized from diethyl ether/heptane to give (1S,8R)-1,11,11-Trimethyl-5-(5-methyl-1-phenyl-1H-pyrazol-4-yl)-3,4-diaza-tricyclo[6.2.1.0$^{2,7}$]undeca-2(7),3,5-triene, 0.32 g as an off-white crystalline solid. MS (EI): 344.2 (M$^+$).

Example 2

(1S,8R)-1,11,11-Trimethyl-5-(2-trifluoromethyl-phenyl)-3,4-diazatricyclo[6.2.1.0$^{2,7}$]undeca-2(7),3,5-triene Step A]: 2-Oxo-2-(2-trifluoromethyl-phenyl)-ethyl]-phosphonic acid dimethyl ester This material was obtained in analogy to example 1 step A] from 2-trifluoromethyl-benzoic acid ethyl ester (5 g) and methyl-phosphonic acid dimethyl ester (5.687 g) to give 2-oxo-2-(2-trifluoromethyl-phenyl)-ethyl]-phosphonic acid dimethyl ester (5.8 g) as a white solid. MS (EI): 296.1 (M$^+$).

Step B]: (1S,4R)-1,7,7-Trimethyl-3-[2-oxo-2-(2-trifluoromethyl-phenyl)-eth-(E)-ylidene]-bicyclo[2.2.1]heptan-2-one This material was obtained in analogy to example 1 step B] from 2-oxo-2-(2-trifluoromethyl-phenyl)-ethyl]-phosphonic acid dimethyl ester (0.89 g) and (1S,4R)-1,7,7-trimethyl-bicyclo[2.2.1]heptane-2,3-dione (0.5 g) to give (1S,4R)-1,7,7-trimethyl-3-[2-oxo-2-(2-trifluoromethyl-phenyl)-eth-(E)-ylidene]-bicyclo[2.2.1]heptan-2-one (0.749 g) as a yellow oil. MS (EI): 336.1 (M$^+$).

Step C]: (1S,8R)-1,11,11-trimethyl-5-(2-trifluoromethyl-phenyl)-3,4-diazatricyclo[6.2.1.0$^{2,7}$]undeca-2(7),3,5-triene This material was obtained in analogy to example 1 step C] from (1S,4R)-1,7,7-trimethyl-3-[2-oxo-2-(2-trifluoromethyl-phenyl)-eth-(E)-ylidene]-bicyclo[2.2.1]heptan-2-one (0.13 g) and hydrazine monohydrate (0.193 g) to give (1S,8R)-1,11,11-trimethyl-5-(2-trifluoromethyl-phenyl)-3,4-diazatricyclo[6.2.1.0$^{2,7}$]undeca-2(7),3,5-triene (0.023 g) as a light yellow crystalline solid. MS (EI): 332.0 (M$^+$).

Example 3

(1S,8R)-1,11,11-Trimethyl-5-(1-phenyl-5-trifluoromethyl-1H-pyrazol-4-yl)-3,4-diaza-tricyclo[6.2.1.0$^{2,7}$]undeca-2(7),3,5-triene Step A]: [2-Oxo-2-(1-phenyl-5-trifluoromethyl-1H-pyrazol-4-yl)-ethyl]-phosphonic acid dimethyl ester This material was obtained in analogy to example 1 step A] from 1-phenyl-5-trifluoromethyl-1H-pyrazole-4-carboxylic acid ethyl ester (5 g) and methyl-phosphonic acid dimethyl ester (4.35 g) to give [2-oxo-2-(1-phenyl-5-trifluoromethyl-1H-pyrazol-4-yl)-ethyl]-phosphonic acid dimethyl ester (4.384 g) as a light brown oil. MS (ESI): 362.9 (MH$^+$).

Step B]: (1S,4R)-1,7,7-Trimethyl-3-[2-oxo-2-(1-phenyl-5-trifluoromethyl-1H-pyrazol-4-yl)-eth-(E)-ylidene]-bicyclo[2.2.1]heptan-2-one This material was obtained in analogy to example 1 steps B] from [2-oxo-2-(1-phenyl-5-trifluoromethyl-1H-pyrazol-4-yl)-ethyl]-phosphonic acid dimethyl ester (1.2 g) and (1S,4R)-1,7,7-trimethyl-bicyclo[2.2.1]heptane-2,3-dione (1.097 g) to give (1S,4R)-1,7,7-trimethyl-3-[2-oxo-2-(1-phenyl-5-trifluoromethyl-1H-pyrazol-4-yl)-eth-(E)-ylidene]-bicyclo[2.2.1]heptan-2-one (1.5 g) as a yellow oil. MS (EI): 402.1 (M$^+$).

Step C]: (1S,8R)-1,11,11-Trimethyl-5-(1-phenyl-5-trifluoromethyl-1H-pyrazol-4-yl)-3,4-diaza-tricyclo[6.2.1.0$^{2,7}$]undeca-2(7),3,5-triene This material was obtained in analogy to example 1 step C] from (1S,4R)-1,7,7-trimethyl-3-[2-oxo-2-(1-phenyl-5-trifluoromethyl-1H-pyrazol-4-yl)-eth-(E)-ylidene]-bicyclo[2.2.1]heptan-2-one (1.5 g) and hydrazine monohydrate (1.866 g) to give (1S,8R)-1,11,11-trimethyl-5-(1-phenyl-5-trifluoromethyl-1H-pyrazol-4-yl)-3,4-diaza-tricyclo[6.2.1.0$^{2,7}$]undeca-2(7),3,5-triene (0.9 g) as a yellow gum. MS (EI): 398.1 (M$^+$).

Example 4

(1S,8R)-5-Adamantan-1-yl-1,11,11-trimethyl-3,4-diaza-tricyclo[6.2.1.0$^{2,7}$]undeca-2,4,6-triene Step A]: 2-Adamantan-1-yl-2-oxo-ethyl)-phosphonic acid dimethyl ester This material was obtained in analogy to example 1 step A] from adamantane-1-carboxylic acid ethyl ester (5 g) and methyl-phosphonic acid dimethyl ester (5.597 g) to give (2-Adamantan-1-yl-2-oxo-ethyl)-phosphonic acid dimethyl ester (8.2 g) as a colorless oil that was used in the next step without further purification. MS (ESI): 286.9 (MH$^+$).

Step B]: (1S,4R)-3-[2-Adamantan-1-yl-2-oxo-eth-(E)-ylidene]-1,7,7-trimethyl-bicyclo[2.2.1]heptan-2-one This material was obtained in analogy to example 1 step B] from (2-adamantan-1-yl-2-oxo-ethyl)-phosphonic acid dimethyl ester (1.72 g) and (1S,4R)-1,7,7-trimethyl-bicyclo[2.2.1]heptane-2,3-dione (1 g) to give (1S,4R)-3-[2-adamantan-1-yl-2-oxo-eth-(E)-ylidene]-1,7,7-trimethyl-bicyclo[2.2.1]heptan-2-one (1.57 g) as a yellow amorphous solid. MS (EI): 326.3 (M$^+$).

Step C]: (1S,8R)-5-Adamantan-1-yl-1,11,11-trimethyl-3,4-diaza-tricyclo[6.2.1.0$^{2,7}$]undeca-2,4,6-triene This material was prepared according to example 1 step C] (1S,4R)-3-[2-adamantan-1-yl-2-oxo-eth-(E)-ylidene]-1,7,7-trimethyl-bicyclo[2.2.1]heptan-2-one (0.2 g) and hydrazine monohydrate (0.117 g) with the following modifications: toluene as solvent (5 ml) in the presence of p-toluene sulfonic acid (0.117 g), heating for 12 h at reflux temperature and isolation of desired product by chromatography (no further NaOMe treatment as in example 1 step C]. This gave (1S,8R)-5-adamantan-1-yl-1,11,11-trimethyl-3,4-diaza-tricyclo[6.2.1.0$^{2,7}$]undeca-2,4,6-triene (0.027 g) as an amorphous light yellow solid. MS (EI): 322.4 (M$^+$).

Example 5

(1S,8R)-5-[2-(3-Chloro-phenyl)-thiazol-4-yl]-1,11,11-trimethyl-3,4-diaza-tricyclo[6.2.1.0$^{2,7}$]undeca-2,4,6-triene Step A]: {2-[2-(3-Chloro-phenyl)-thiazol-4-yl]-2-oxo-ethyl}-phosphonic acid dimethyl ester This material was obtained in analogy to example 1 step A] from 2-(3-Chloro-phenyl)-thiazole-4-carboxylic acid ethyl ester (1.93 g) and methyl-phosphonic acid dimethyl ester (1.789 g) to give {2-[2-(3-chloro-phenyl)-thiazol-4-yl]-2-oxo-ethyl}-phosphonic acid dimethyl ester (2.8 g) as a dark red viscous oil. MS (ESI): 346.1 (MH$^+$).

Step B]: (1S,4R)-3-[2-[2-(3-Chloro-phenyl)-thiazol-4-yl]-2-oxo-eth-(E)-ylidene]-1,7,7-trimethyl-bicyclo[2.2.1]heptan-2-one This material was obtained in analogy to example 1 step B] from {2-[2-(3-chloro-phenyl)-thiazol-4-yl]-2-oxo-ethyl}-phosphonic acid dimethyl ester (0.732 g) and (1S,4R)-1,7,7-trimethyl-bicyclo[2.2.1]heptane-2,3-dione (0.35 g) to give (1S,4R)-3-[2-[2-(3-chloro-phenyl)-thiazol-4-yl]-2-oxo-eth-(E)-ylidene]-1,7,7-trimethyl-bicyclo[2.2.1]heptan-2-one (0.643 g) as a light brown amorphous solid. MS (EI): 385.1 (M$^+$). Tentative assignment of stereochemistry Step C]: (1S,8R)-5-[2-(3-Chloro-phenyl)-thiazol-4-yl]-1,11,11-trimethyl-3,4-diaza-tricyclo[6.2.1.02,7]undeca-2,4,6-triene This material was obtained in analogy to example 4 steps C] from (1S,4R)-3-[2-[2-(3-chloro-phenyl)-thiazol-4-yl]-2-oxo-eth-(E)-ylidene]-1,7,7-trimethyl-bicyclo[2.2.1]heptan-2-one (0.2 g) and hydrazine monohydrate (0.099 g) to give (1S,8R)-5-[2-(3-chloro-phenyl)-thiazol-4-yl]-1,11,11-trimethyl-3,4-diaza-tricyclo[6.2.1.02,7]undeca-2,4,6-triene (0.021 g) as an amorphous orange solid. MS (EI): 381.2 (M$^+$).

Example 6

(1R,8S)-5-(2-Chloro-phenyl)-1,11,11-trimethyl-3,4-diaza-tricyclo[6.2.1.0$^{2,7}$]undeca-2,4,6-triene Step A]: [2-(2-Chloro-phenyl)-2-oxo-ethyl]-phosphonic acid dimethyl ester This material was obtained in analogy to example 1 step A] from 2-chloro-benzoic acid methyl ester (5 g) and methyl-phosphonic acid dimethyl ester (7.273 g) to give [2-(2-chloro-phenyl)-2-oxo-ethyl]-phosphonic acid dimethyl ester (10 g) as a colorless liquid that was used without further purification MS (EI): 263.1 (M$^+$).

Step B]: (1R,4S)-3-[2-(2-Chloro-phenyl)-2-oxo-eth-(E)-ylidene]-1,7,7-trimethyl-bicyclo[2.2.1]heptan-2-one This material was obtained in analogy to example 1 step B] from [2-(2-chloro-phenyl)-2-oxo-ethyl]-phosphonic acid dimethyl ester (1.58 g) and (1R,4S)-1,7,7-trimethyl-bicyclo[2.2.1]heptane-2,3-dione (1 g) to give (1R,4S)-3-[2-(2-Chloro-phenyl)-2-oxo-eth-(E)-ylidene]-1,7,7-trimethyl-bicyclo[2.2.1]heptan-2-one (0.772 g) as a yellow solid. MS (EI): 302 (M$^+$).

Step C]: (1R,8S)-5-(2-Chloro-phenyl)-1,11,11-trimethyl-3,4-diaza-tricyclo[6.2.1.0$^{2,7}$]undeca-2,4,6-triene This material was obtained in analogy to example 1 steps C] from (1R,4S)-3-[2-(2-chloro-phenyl)-2-oxo-eth-(E)-ylidene]-1,7,7-trimethyl-bicyclo[2.2.1]heptan-2-one (0.2 g) and hydrazine monohydrate (0.165 g) to give (1R,8S)-5-(2-chloro-phenyl)-1,11,11-trimethyl-3,4-diaza-tricyclo[6.2.1.0$^{2,7}$]undeca-2,4,6-triene (0.036 g) as a light yellow solid. MS (EI): 298.2 (M$^+$).

Example 7

(1S,8R)-1,11,11-Trimethyl-5-phenyl-3,4-diaza-tricyclo[6.2.1.0$^{2,7}$]undeca-2,4,6-triene Step A]: (1S,4R)-1,7,7-Trimethyl-3-[2-oxo-2-phenyl-eth-(E)-ylidene]-bicyclo[2.2.1]heptan-2-one and (1S,4R)-1,7,7-trimethyl-3-[2-oxo-2-phenyl-eth-(Z)-ylidene]-bicyclo[2.2.1]heptan-2-one This material was obtained in analogy to example 1 step B] from (2-oxo-2-phenyl-ethyl)-phosphonic acid diethyl ester (1.69 g) and (1S,4R)-1,7,7-trimethyl-bicyclo[2.2.1]heptane-2,3-dione (1 g) to give (1S,4R)-1,7,7-trimethyl-3-[2-oxo-2-phenyl-eth-(E)-ylidene]-bicyclo[2.2.1]heptan-2-one (0.962 g) and (1S,4R)-1,7,7-Trimethyl-3-[2-oxo-2-phenyl-eth-(Z)-ylidene]-bicyclo[2.2.1]heptan-2-one (0.672 g) as a yellow solids, respectively. MS (EI): 268.2 (M$^+$).

Step B]: (1S,8R)-1,11,11-Trimethyl-5-phenyl-3,4-diaza-tricyclo[6.2.1.0$^{2,7}$]undeca-2,4,6-triene This material was obtained in analogy to example 4 steps C] from]: (1S,4R)-1,7,7-trimethyl-3-[2-oxo-2-phenyl-eth-(E)-ylidene]-bicyclo[2.2.1]heptan-2-one (0.2 g) and hydrazine monohydrate (0.187 g) to give (1S,8R)-1,11,11-Trimethyl-5-phenyl-3,4-diaza-tricyclo[6.2.1.0$^{2,7}$]undeca-2,4,6-triene (0.036 g) as a yellow solid. MS (ESI): 265.2 (MH$^+$).

Example 8

(1R,8S)-1,11,11-Trimethyl-5-phenyl-3,4-diaza-tricyclo[6.2.1.0$^{2,7}$]undeca-2,4,6-triene Step A]: (1R,4S)-1,7,7-Trimethyl-3-[2-oxo-2-phenyl-eth-(E)-ylidene]-bicyclo[2.2.1]heptan-2-one and (1R,4S)-1,7,7-Trimethyl-3-[2-oxo-2-phenyl-eth-(Z)-ylidene]-bicyclo[2.2.1]heptan-2-one This material was obtained in analogy to example 1 step B] from (2-oxo-2-phenyl-ethyl)-phosphonic acid diethyl ester (1.69 g) and (1R,4S)-1,7,7-trimethyl-bicyclo[2.2.1]heptane-2,3-dione (1 g) to give (1R,4S)-1,7,7-trimethyl-3-[2-oxo-2-phenyl-eth-(E)-ylidene]-bicyclo[2.2.1]heptan-2-one (0.515 g) and (1R,4S)-1,7,7-Trimethyl-3-[2-oxo-2-phenyl-eth-(Z)- ylidene]-bicyclo[2.2.1]heptan-2-one (0.478 g) as a yellow solids, respectively. MS (EI): 268.2 (M⁺).

Step B]: (1S,8R)-1,11,11-Trimethyl-5-phenyl-3,4-diaza-tricyclo[6.2.1.0$^{2,7}$]undeca-2,4,6-triene This material was obtained in analogy to example 4 steps C] from (1R,4S)-1,7,7-trimethyl-3-[2-oxo-2-phenyl-eth-(Z)-ylidene]-bicyclo[2.2.1]heptan-2-one (0.2 g) and hydrazine monohydrate (0.187 g) to give (1R,8S)-1,11,11-trimethyl-5-phenyl-3,4-diaza-tricyclo[6.2.1.0$^{2,7}$]undeca-2,4,6-triene (0.042 g) as a light yellow solid. MS (ESI): 265.2 (MH⁺).

Example 9

(1R,8S)-1,11,11-Trimethyl-5-(2-trifluoromethyl-phenyl)-3,4-diazatricyclo[6.2.1.0$^{2,7}$]undeca-2,4,6-triene Step A]: (1R,4S)-1,7,7-Trimethyl-3-[2-oxo-2-(2-trifluoromethyl-phenyl)-eth-(E)-ylidene]-bicyclo[2.2.1]heptan-2-one This material was obtained in analogy to example 1 step B] 2-oxo-2-(2-trifluoromethyl-phenyl)-ethyl]-phosphonic acid dimethyl ester (0.312 g) and (1R,4S)-1,7,7-trimethyl-bicyclo[2.2.1]heptane-2,3-dione (0.35 g) to give (1R,4S)-1,7,7-Trimethyl-3-[2-oxo-2-(2-trifluoromethyl-phenyl)-eth-(E)-ylidene]-bicyclo[2.2.1]heptan-2-one (0.237 g) as a yellow oil. MS (EI): 336.2 (M⁺).

Step B]: (1R,8S)-1,11,11-Trimethyl-5-(2-trifluoromethyl-phenyl)-3,4-diazatricyclo[6.2.1.0$^{2,7}$]undeca-2,4,6-triene This material was obtained in analogy to example 1 step C] from (1R,4S)-1,7,7-trimethyl-3-[2-oxo-2-(2-trifluoromethyl-phenyl)-eth-(E)-ylidene]-bicyclo[2.2.1]heptan-2-one (0.23 g) and hydrazine monohydrate (0.17 g) to give (1R,8S)-1,11,11-trimethyl-5-(2-trifluoromethyl-phenyl)-3,4-diaza-tricyclo[6.2.1.0$^{2,7}$]undeca-2,4,6-triene (0.024 g) as a light yellow crystalline solid. MS (ESI): 333.0 (MH⁺).

Example 10

(1R,8S)-1,11,11-Trimethyl-5-(4-trifluoromethyl-phenyl)-3,4-diazatricyclo[6.2.1.0$^{2,7}$]undeca-2,4,6-triene Step A]: (1R,4S)-1,7,7-Trimethyl-3-[2-oxo-2-(4-trifluoromethyl-phenyl)-eth-(E)-ylidene]-bicyclo[2.2.1]heptan-2-one This material was obtained in analogy to example 1 step B] 2-oxo-2-(4-trifluoromethyl-phenyl)-ethyl]-phosphonic acid dimethyl ester (0.534 g, synthesis described in DE 2322142) and (1R,4S)-1,7,7-trimethyl-bicyclo[2.2.1]heptane-2,3-dione (0.3 g) to give (1R,4S)-1,7,7-trimethyl-3-[2-oxo-2-(4-trifluoromethyl-phenyl)-eth-(E)-ylidene]-bicyclo[2.2.1]heptan-2-one (0.476 g) as a yellow solid MS (EI): 336.1 (M⁺).

Step B]: (1R,8S)-1,11,11-Trimethyl-5-(4-trifluoromethyl-phenyl)-3,4-diazatricyclo[6.2.1.0$^{2,7}$]undeca-2,4,6-triene This material was obtained in analogy to example 4 step C] from (1R,4S)-1,7,7-trimethyl-3-[2-oxo-2-(4-trifluorom-ethyl-phenyl)-eth-(E)-ylidene]-bicyclo[2.2.1]heptan-2-one (0.2 g) and hydrazine monohydrate (0.149 g) to give (1R,8S)-1,11,11-trimethyl-5-(4-trifluoromethyl-phenyl)-3,4-diaza-tricyclo[6.2.1.0$^{2,7}$]undeca-2,4,6-triene (0.03 g) as an amorphous light yellow solid. MS (EI): 332.1 (M⁺).

Example 11

(1S,8R)-5-(4-Fluoro-phenyl)-1,11,11-trimethyl-3,4-diaza-tricyclo[6.2.1.0$^{2,7}$]undeca-2,4,6-triene Step A]:
[2-(4-Fluoro-phenyl)-2-oxo-ethyl]-phosphonic acid dimethyl ester This material was obtained in analogy to example 1 step A] from 4-fluoro-benzoic acid methyl ester (5 g) and methyl-phosphonic acid dimethyl ester (8.05 g) to give [2-(4-fluoro-phenyl)-2-oxo-ethyl]-phosphonic acid dimethyl ester (7.4 g) as a colorless oil. MS (ESI): 246.9 (MH⁺).

Step B]: (1S,4R)-3-[2-(4-Fluoro-phenyl)-2-oxo-eth-(E)-ylidene]-1,7,7-trimethyl-bicyclo[2.2.1]heptan-2-one This material was obtained in analogy to example 1 step B] from [2-(4-fluoro-phenyl)-2-oxo-ethyl]-phosphonic acid dimethyl ester (0.5 g) and (1S,4R)-1,7,7-trimethyl-bicyclo[2.2.1]heptane-2,3-dione (0.675 g) to give (1S,4R)-3-[2-(4-fluoro-phenyl)-2-oxo-eth-(E)-ylidene]-1,7,7-trimethyl-bicyclo[2.2.1]heptan-2-one (0.46 g) as a yellow oil. MS (EI): 286.1 (M⁺).

Step C]: (1S,8R)-5-(4-Fluoro-phenyl)-1,11,11-trimethyl-3,4-diaza-tricyclo[6.2.1.0$^{2,7}$]undeca-2,4,6-triene This material was obtained in analogy to example 1 steps C] from (1S,4R)-3-[2-(4-fluoro-phenyl)-2-oxo-eth-(E)-ylidene]-1,7,7-trimethyl-bicyclo[2.2.1]heptan-2-one (0.2 g) and hydrazine monohydrate (0.175 g) to (1S,8R)-5-(4-fluoro-phenyl)-1,11,11-trimethyl-3,4-diaza-tricyclo[6.2.1.0$^{2,7}$]undeca-2,4,6-triene (0.033 g) as a yellow solid. MS (ESI): 282.2 (MH⁺).

Example 12

(1S,8R)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene Step A]: {2-[1-(4-Chloro-phenyl)-5-trifluoromethyl-1H-pyrazol-4-yl]-2-oxo-ethyl}-phosphonic acid dimethyl ester This material was obtained in analogy to example 1 step A] from 1-(4-Chloro-phenyl)-5-trifluoromethyl-1H-pyrazole-4-carboxylic acid ethyl ester (2.5 g) and methyl-phosphonic acid dimethyl ester (1.94 g) to give {2-[1-(4-chloro-phenyl)-5-trifluoromethyl-1H-pyrazol-4-yl]-2-oxo-ethyl}-phosphonic acid dimethyl ester (3.1 g) as a yellow oil that was used in the next step without further purification.

Step B]: (1S,4R)-3-{2-[1-(4-chloro-phenyl)-5-trifluoromethyl-1H-pyrazol-4-yl]-2-oxo-eth-(E)-ylidene}-1,7,7-trimethyl-bicyclo[2.2.1]heptan-2-one This material was obtained in analogy to example 1 step B] from {2-[1-(4-chloro-phenyl)-5-trifluoromethyl-1H-pyrazol-4-yl]-2-oxo-ethyl}-phosphonic acid dimethyl ester (1.69 g) and (1S,4R)-1,7,7-trimethyl-bicyclo[2.2.1]heptane-2,3-dione (1.468 g) to give (1S,4R)-3-{2-[1-(4-chloro-phenyl)-5-trifluoromethyl-1H-pyrazol-4-yl]-2-oxo-eth-(E)-ylidene}-1,7,7-trimethyl-bicyclo[2.2.1]heptan-2-one (1.236 g) as a yellow solid. MS (EI): 436.1 (M$^+$).

Step C]: (1S,8R)-5-[1-(4-Chloro-phenyl)-5-trifluoromethyl-1H-pyrazol-4-yl]-1,11,1-trimethyl-3,4-diaza-tricyclo[6.2.1.0$^{2,7}$]undeca-2,4,6-triene This material was obtained in analogy to example 1 steps C] from (1S,4R)-3-{2-[1-(4-chloro-phenyl)-5-trifluoromethyl-1H-pyrazol-4-yl]-2-oxo-eth-(E)-ylidene}-1,7,7-trimethyl-bicyclo[2.2.1]heptan-2-one (0.87 g) and hydrazine monohydrate (1 g) to give (1S,8R)-5-[1-(4-chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene (0.256 g) as a crystalline white solid. MS (ESI): 433.0 (MH$^+$).

Example 13

(1S,8R)-5-(2-Chloro-phenyl)-1,11,11-trimethyl-3,4-diaza-tricyclo[6.2.1.0$^{2,7}$]undeca-2,4,6-triene Step A]: (1S,4R)-3-[2-(2-Chloro-phenyl)-2-oxo-eth-(E)-ylidene]-1,7,7-trimethyl-bicyclo[2.2.1]heptan-2-one This material was obtained in analogy to example 1 step B] from [2-(2-Chloro-phenyl)-2-oxo-ethyl]-phosphonic acid dimethyl ester (0.316 g) and (1S,4R)-1,7,7-trimethyl-bicyclo[2.2.1]heptane-2,3-dione (0.4 g) to give (1S,4R)-3-[2-(2-chloro-phenyl)-2-oxo-eth-(E)-ylidene]-1,7,7-trimethyl-bicyclo[2.2.1]heptan-2-one (0.2 g) as a yellow oil. MS (EI): 302.2 (M$^+$).

Step B]: (1S,8R)-5-(2-Chloro-phenyl)-1,11,11-trimethyl-3,4-diaza-tricyclo[6.2.1.0$^{2,7}$]undeca-2,4,6-triene This material was obtained in analogy to example 1 steps C] from (1S,4R)-3-[2-(2-Chloro-phenyl)-2-oxo-eth-(E)-ylidene]-1,7,7-trimethyl-bicyclo[2.2.1]heptan-2-one (0.19 g) and hydrazine monohydrate (0.157 g) to give (1S,8R)-5-(2-Chloro-phenyl)-1,11,11-trimethyl-3,4-diaza-tricyclo[6.2.1.0$^{2,7}$]undeca-2,4,6-triene (0.06 g) as a light yellow solid. MS (EI): 298.0 (M$^+$).

Example 14

(1R,8S)-1,11,11-Trimethyl-5-(1-phenyl-5-trifluoromethyl-1H-pyrazol-4-yl)-3,4-diaza-tricyclo[6.2.1.0$^{2,7}$]undeca-2,4,6-triene Step A]: (1R,4S)-1,7,7-Trimethyl-3-[2-oxo-2-(1-phenyl-5-trifluoromethyl-1H-pyrazol-4-yl)-eth-(E)-ylidene]-bicyclo[2.2.1]heptan-2-one This material was obtained in analogy to example 1 steps B] from [2-oxo-2-(1-phenyl-5-trifluoromethyl-1H-pyrazol-4-yl)-ethyl]-phosphonic acid dimethyl ester (0.434 g) and (1R,4S)-1,7,7-trimethyl-bicyclo[2.2.1]heptane-2,3-dione (0.166 g) to give (1R,4S)-1,7,7-trimethyl-3-[2-oxo-2-(1-phenyl-5-trifluoromethyl-1H-pyrazol-4-yl)-eth-(E)-ylidene]-bicyclo[2.2.1]heptan-2-one (0.32 g) as a light yellow crystalline solid. MS (EI): 402.2 (M$^+$).

Step B]: (1R,8S)-1,11,11-trimethyl-5-(1-phenyl-5-trifluoromethyl-1H-pyrazol-4-yl)-3,4-diaza-tricyclo[6.2.1.0$^{2,7}$]undeca-2,4,6-triene This material was obtained in analogy to example 1 step C from (1R,4S)-1,7,7-trimethyl-3-[2-oxo-2-(1-phenyl-5-trifluoromethyl-1H-pyrazol-4-yl)-eth-(E)-ylidene]-bicyclo[2.2.1]heptan-2-one (0.318 g) and hydrazine monohydrate (0.396 g) to give (1R,8S)-1,11,11-trimethyl-5-(1-phenyl-5-trifluoromethyl-1H-pyrazol-4-yl)-3,4-diaza-tricyclo[6.2.1.0$^{2,7}$]undeca-2,4,6-triene (0.25 g) as a light yellow foam. MS (EI): 398.2 (M$^+$).

Example 15

(1R,8S)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene Step A]: (1R,4S)-3-{2-[1-(4-Chloro-phenyl)-5-trifluoromethyl-1H-pyrazol-4-yl]-2-oxo-eth-(E)-ylidene}-1,7,7-trimethyl-bicyclo[2.2.1]heptan-2-one This material was obtained in analogy to example 1 step B] from {2-[1-(4-chloro-phenyl)-5-trifluoromethyl-1H-pyrazol-4-yl]-2-oxo-ethyl}-phosphonic acid dimethyl ester (0.459 g) and (1R,4S)-1,7,7-trimethyl-bicyclo[2.2.1]heptane-2,3-dione (0.166 g) to give (1R,4S)-3-{2-[1-(4-chloro-phenyl)-5-trifluoromethyl-1H-pyrazol-4-yl]-2-oxo-eth-(E)-ylidene}-1,7,7-trimethyl-bicyclo[2.2.1]heptan-2-one (0.367 g) as a yellow solid. MS (EI): 436.2 (M$^+$).

Step B]: (1R,8S)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene This material was obtained in analogy to example 1 steps C] from (1R,4S)-3-{2-[1-(4-chloro-phenyl)-5-trifluoromethyl-1H-pyrazol-4-yl]-2-oxo-eth-(E)-ylidene}-1,7,7-trimethyl-bicyclo[2.2.1]heptan-2-one (0.18 g) and hydrazine monohydrate (0.206 g) to give (1R,8S)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene (0.1 g) as a crystalline white solid. MS (EI): 432.2 (M$^+$).

Example 16

(1R,8S)-1,11,11-Trimethyl-5-(5-methyl-1-phenyl-1H-pyrazol-4-yl)-3,4-diaza-tricyclo[6.2.1.0$^{2,7}$]undeca-2,4,6-triene Step A]: (1R,4S)-1,7,7-Trimethyl-3-[2-(5-methyl-1-phenyl-1H-pyrazol-4-yl)-2-oxo-eth-(E)-ylidene]-bicyclo[2.2.1]heptan-2-one This material was obtained in analogy to example 1 step B] from [2-(5-methyl-1-phenyl-1H-pyrazol-4-yl)-2-oxo-ethyl]-phosphonic acid dimethyl ester (0.296 g) and (1R,4S)-1,7,7-trimethyl-bicyclo[2.2.1]heptane-2,3-dione (0.133 g) to give (1R,4S)-1,7,7-trimethyl-3-[2-(5-methyl-1-phenyl-1H-pyrazol-4-yl)-2-oxo-eth-(E)-ylidene]-bicyclo[2.2.1]heptan-2-one (0.148 g) as a yellow solid. MS (EI): 348.1 (M$^+$).

Step B]: (1R,8S)-1,11,11-Trimethyl-5-(5-methyl-1-phenyl-1H-pyrazol-4-yl)-3,4-diaza-tricyclo[6.2.1.0$^{2,7}$]undeca-2,4,6-triene This material was obtained in analogy to example 1 steps C] from (1R,4S)-1,7,7-Trimethyl-3-[2-(5-methyl-1-phenyl-1H-pyrazol-4-yl)-2-oxo-eth-(E)-ylidene]-bicyclo[2.2.1]heptan-2-one (0.145 g) and hydrazine monohydrate (0.208 g) to give (1R,8S)-1,11,11-Trimethyl-5-(5-methyl-1-phenyl-1H-pyrazol-4-yl)-3,4-diaza-tricyclo[6.2.1.0$^{2,7}$]undeca-2,4,6-triene (0.033 g) as an of-white solid. MS (EI): 344.2 (M$^+$).

Example 17

(1S,8R)-5-(2,4-Difluoro-phenyl)-1,11,11-trimethyl-3,4-diaza-tricyclo[6.2.1.0$^{2,7}$]undeca-2,4,6-triene Step A]:
[2-(2,4-Difluoro-phenyl)-2-oxo-ethyl]-phosphonic acid dimethyl ester This material was obtained in analogy to example 1 step A] from 2,4-difluoro-benzoic acid ethyl ester (5 g) and methyl-phosphonic acid dimethyl ester (6.65 g) to [2-(2,4-difluoro-phenyl)-2-oxo-ethyl]-phosphonic acid dimethyl ester (5.755 g) as a colorless liquid. MS (ESI): 264.9 (MH$^+$).

Step B]: (1S,4R)-3-[2-(2,4-difluoro-phenyl)-2-oxo-eth-(E)-ylidene]-1,7,7-trimethyl-bicyclo[2.2.1]heptan-2-one This material was obtained in analogy to example 1 step B) from [2-(2,4-difluoro-phenyl)-2-oxo-ethyl]-phosphonic acid dimethyl ester (0.38 g) and (1S,4R)-1,7,7-trimethyl-bicyclo[2.2.1]heptane-2,3-dione (0.2 g) to give (1S,4R)-3-[2-(2,4-difluoro-phenyl)-2-oxo-eth-(E)-ylidene]-1,7,7-trimethyl-bicyclo[2.2.1]heptan-2-one (0.324 g) as a yellow solid. MS (EI): 304.1 (M$^+$).

Step C]: (1S,8R)-5-(2,4-Difluoro-phenyl)-1,11,11-trimethyl-3,4-diaza-tricyclo[6.2.1.0$^{2,7}$]undeca-2,4,6-triene This material was obtained in analogy to example 1 steps C] from (1S,4R)-3-[2-(2,4-difluoro-phenyl)-2-oxo-eth-(E)-ylidene]-1,7,7-trimethyl-bicyclo[2.2.1]heptan-2-one (0.2 g) and hydrazine monohydrate (0.164 g) to give (1S,8R)-5-(2,4-Difluoro-phenyl)-1,11,11-trimethyl-3,4-diaza-tricyclo[6.2.1.0$^{2,7}$]undeca-2,4,6-triene (0.062 g) as an off-white solid. MS (EI): 300.2 (M$^+$).

Example 18

(1S,8R)-5-(2-Fluoro-phenyl)-1,11,11-trimethyl-3,4-diaza-tricyclo[6.2.1.0$^{2,7}$]undeca-2,4,6-triene Step A]:
[2-(2-Fluoro-phenyl)-2-oxo-ethyl]-phosphonic acid dimethyl ester This material was obtained in analogy to example 1 step A] from 2-fluoro-benzoic acid ethyl ester (5 g) and methyl-phosphonic acid dimethyl ester (7.378 g) to give [2-(2-fluoro-phenyl)-2-oxo-ethyl]-phosphonic acid dimethyl ester (4.935 g) as a colorless liquid. MS (ESI): 246.9 (MH$^+$).

Step B]: (1S,4R)-3-[2-(2-Fluoro-phenyl)-2-oxo-eth-(E)-ylidene]-1,7,7-trimethyl-bicyclo[2.2.1]heptan-2-one This material was obtained in analogy to example 1 step B] from [2-(2-fluoro-phenyl)-2-oxo-ethyl]-phosphonic acid dimethyl ester (0.355 g) and (1S,4R)-1,7,7-trimethyl-bicyclo[2.2.1]heptane-2,3-dione (0.2 g) to give (1S,4R)-3-[2-(2-fluoro-phenyl)-2-oxo-eth-(E)-ylidene]-1,7,7-trimethyl-bicyclo[2.2.1]heptan-2-one (0.321 g) as a yellow oil. MS (EI): 286.2 (M$^+$).

Step C]: (1S,8R)-5-(2-Fluoro-phenyl)-1,11,11-trimethyl-3,4-diaza-tricyclo[6.2.1.0$^{2,7}$]undeca-2,4,6-triene This material was obtained in analogy to example 1 steps C] from (1S,4R)-3-[2-(2-fluoro-phenyl)-2-oxo-eth-(E)-ylidene]-1,7,7-trimethyl-bicyclo[2.2.1]heptan-2-one (0.3 g) and hydrazine monohydrate (0.262 g) to give (1S,8R)-5-(2-fluoro-phenyl)-1,11,11-trimethyl-3,4-diaza-tricyclo[6.2.1.0$^{2,7}$]undeca-2,4,6-triene (0.1 g) as an off-white solid. MS (EI): 282.2 (M$^+$).

Example 19

(1S,8R)-5-(2,5-Difluoro-phenyl)-1,11,11-trimethyl-3,4-diaza-tricyclo[6.2.1.0$^{2,7}$]undeca-2,4,6-triene Step A]:
[2-(2,5-Difluoro-phenyl)-2-oxo-ethyl]-phosphonic acid dimethyl ester This material was obtained in analogy to example 1 step A] from 2,5-difluoro-benzoic acid methyl ester (4.9 g) and methyl-phosphonic acid dimethyl ester (7.122 g) to [2-(2,5-difluoro-phenyl)-2-oxo-ethyl]-phosphonic acid dimethyl ester (8.166 g) as a light yellow liquid that was used without further purification in the next step. MS (ESI): 264.9 (MH$^+$).

Step B]: (1S,4R)-3-[2-(2,5-Difluoro-phenyl)-2-oxo-eth-(E)-ylidene]-1,7,7-trimethyl-bicyclo[2.2.1]heptan-2-one This material was obtained in analogy to example 1 step B] from [2-(2,5-difluoro-phenyl)-2-oxo-ethyl]-phosphonic acid dimethyl ester (0.38 g) and (1S,4R)-1,7,7-trimethyl-bicyclo[2.2.1]heptane-2,3-dione (0.2 g) to give (1S,4R)-3-[2-(2,5-difluoro-phenyl)-2-oxo-eth-(E)-ylidene]-1,7,7-trimethyl-bicyclo[2.2.1]heptan-2-one (0.474 g) as a yellow solid. MS (EI): 304.1 (M$^+$).

Step C]: (1S,8R)-5-(2,5-Difluoro-phenyl)-1,11,11-trimethyl-3,4-diaza-tricyclo[6.2.1.0$^{2,7}$]undeca-2,4,6-triene This material was obtained in analogy to example 1 steps C] from (1S,4R)-3-[2-(2,5-difluoro-phenyl)-2-oxo-eth-(E)-ylidene]-1,7,7-trimethyl-bicyclo[2.2.1]heptan-2-one (0.2 g) and hydrazine monohydrate (0.164 g) to give (1S,8R)-5-(2,5-difluoro-phenyl)-1,11,11-trimethyl-3,4-diaza-tricyclo[6.2.1.0$^{2,7}$]undeca-2,4,6-triene (0.063 g) as an off-white solid. MS (EI): 300.2 (M$^+$).

Example 20

(1S,8R)-1,11,11-Trimethyl-5-(1-phenyl-5-propyl-1H-pyrazol-4-yl)-3,4-diazatricyclo[6.2.1.0$^{2,7}$]undeca-2(7),3,5-triene

Step A]: [2-Oxo-2-(1-phenyl-5-propyl-1H-pyrazol-4-yl)-ethyl]-phosphonic acid dimethyl ester This material was obtained in analogy to example 1 step A] from 1-Phenyl-5-propyl-1H-pyrazole-4-carboxylic acid ethyl ester (5 g) and methyl-phosphonic acid dimethyl ester (4.8 g) to give [2-oxo-2-(1-phenyl-5-propyl-1H-pyrazol-4-yl)-ethyl]-phosphonic acid dimethyl ester (6.32 g) as a brown oil. MS (ESI): 336.9 (MH$^+$).

Step B]: (1S,4R)-1,7,7-Trimethyl-3-[2-oxo-2-(1-phenyl-5-propyl-1H-pyrazol-4-yl)-eth-(E)-ylidene]-bicyclo[2.2.1]heptan-2-one This material was obtained in analogy to example 1 step B] from [2-oxo-2-(1-phenyl-5-propyl-1H-pyrazol-4-yl)-ethyl]-phosphonic acid dimethyl ester (0.4 g) and (1S,4R)-1,7,7-trimethyl-bicyclo[2.2.1]heptane-2,3-dione (0.198 g) to give (1S,4R)-1,7,7-trimethyl-3-[2-oxo-2-(1-phenyl-5-propyl-1H-pyrazol-4-yl)-eth-(E)-ylidene]-bicyclo[2.2.1]heptan-2-one (0.132 g) as a yellow oil. MS (ESI): 377.3 (MH$^+$).

Step C]: (1S,8R)-1,11,11-Trimethyl-5-(1-phenyl-5-propyl-1H-pyrazol-4-yl)-3,4-diazatricyclo[6.2.1.0$^{2,7}$]undeca-2(7),3,5-triene This material was obtained in analogy to example 1 steps C] from (1S,4R)-1,7,7-trimethyl-3-[2-oxo-2-(1-phenyl-5-propyl-1H-pyrazol-4-yl)-eth-(E)-ylidene]-bicyclo[2.2.1]heptan-2-one (0.132 g) and hydrazine monohydrate (0.088 g) to give (1S,8R)-1,11,11-trimethyl-5-(1-phenyl-5-propyl-1H-pyrazol-4-yl)-3,4-diazatricyclo[6.2.0$^{2,7}$]undeca-2(7),3,5-triene (0.044 g) as a light yellow foam. MS (EI): 372.2 (M$^+$).

Example 21

(1S,8R)-1,11,11-Trimethyl-5-(1-methyl-1H-indol-3-yl)-3,4-diaza-tricyclo[6.2.1.0$^{2,7}$]undeca-2(7),3,5-triene

Step A]: [2-(1-Methyl-1H-indol-3-yl)-2-oxo-ethyl]-phosphonic acid dimethyl ester This material was obtained in analogy to example 1 step A] from 1-Methyl-1H-indole-3-carboxylic acid methyl ester (0.7 g) and methyl-phosphonic acid dimethyl ester (0.908 g) to give [2-(1-methyl-1H-indol-3-yl)-2-oxo-ethyl]-phosphonic acid dimethyl ester (0.8 g) as a light yellow liquid. MS (ESI): 282.0 (MH$^+$).

Step B]: (1S,4R)-1,7,7-Trimethyl-3-[2-(1-methyl-1H-indol-3-yl)-2-oxo-eth-(E)-ylidene]-bicyclo[2.2.1]heptan-2-one and (1S,4R)-1,7,7-Trimethyl-3-[2-(1-methyl-1H-indol-3-yl)-2-oxo-eth-(Z)-ylidene]-bicyclo[2.2.1]heptan-2-one In analogy to example 1 step B] on reaction of [2-(1-Methyl-1H-indol-3-yl)-2-oxo-ethyl]-phosphonic acid dimethyl ester (0.406 g) and (1S,4R)-1,7,7-trimethyl-bicyclo[2.2.1]heptane-2,3-dione (0.2 g) there was obtained (1S,4R)-1,7,7-trimethyl-3-[2-(1-methyl-1H-indol-3-yl)-2-oxo-eth-(E)-ylidene]-bicyclo[2.2.1]heptan-2-one (0.098 g), light yellow oil, and (1S,4R)-1,7,7-trimethyl-3-[2-(1-methyl-1H-indol-3-yl)-2-oxo-eth-(Z)-ylidene]-bicyclo[2.2.1]heptan-2-one (0.079 g), light yellow solid. MS (EI): 321.3 (M$^+$), respectively.

Step C]: (1S,8R)-1,11,11-Trimethyl-5-(1-methyl-1H-indol-3-yl)-3,4-diaza-tricyclo[6.2.1.0$^{2,7}$]undeca-2(7),3,5-triene This material was obtained in analogy to example 1 steps C] from (1S,4R)-1,7,7-trimethyl-3-[2-(1-methyl-1H-indol-3-yl)-2-oxo-eth-(Z)-ylidene]-bicyclo[2.2.1]heptan-2-one (0.07 g) and hydrazine monohydrate (0.055 g), without the NaOMe treatment, to give (1S,8R)-1,11,11-Trimethyl-5-(1-methyl-1H-indol-3-yl)-3,4-diazatricyclo[6.2.1.0$^{2,7}$]undeca-2(7),3,5-triene (0.054 g) as a white solid. MS (EI): 317.2 (M$^+$).

Example 22

(1S,8R)-5-[1-(4-Chloro-phenyl)-cyclopropyl]-1,11,11-trimethyl-3,4-diaza-tricyclo [6.2.1.0$^{2,7}$]undeca-2,4,6-triene

Step A]: {2-[1-(4-Chloro-phenyl)-cyclopropyl]-2-oxo-ethyl}-phosphonic acid dimethyl ester This material was obtained in analogy to example 1 step A] from 1-(4-chloro-phenyl)-cyclopropanecarboxylic acid methyl ester (5.29 g) and methyl-phosphonic acid dimethyl ester (6.23 g) to give {2-[1-(4-chloro-phenyl)-cyclopropyl]-2-oxo-ethyl}-phosphonic acid dimethyl ester (7.28 g) as an off-white oil. MS (ESI): 303.0 (MH$^+$).

Step B: (1S,4R)-3-[2-[1-(4-chloro-phenyl)-cyclopropyl]-2-oxo-eth-(E)-ylidene]-1,7,7-trimethyl-bicyclo[2.2.1]heptan-2-one In analogy to example 1 step B] on reaction of {2-[1-(4-chloro-phenyl)-cyclopropyl]-2-oxo-ethyl}-phosphonic acid dimethyl ester (0.437 g) and (1S,4R)-1,7,7-trimethyl-bicyclo[2.2.1]heptane-2,3-dione (0.2 g) there was obtained (1S,4R)-3-[2-[1-(4-chloro-phenyl)-cyclopropyl]-2-oxo-eth-(E)-ylidene]-1,7,7-trimethyl-bicyclo[2.2.1]heptan-2-one (0.334 g) as a yellow oil. MS (EI): 342.1 (M$^+$).

Step C]: (1S,8R)-5-[1-(4-Chloro-phenyl)-cyclopropyl]-1,11,11-trimethyl-3,4-diaza-tricyclo[6.2.1.0$^{2,7}$]undeca-2,4,6-triene This material was obtained in analogy to example 1 steps C] from (1S,4R)-3-[2-[1-(4-Chloro-phenyl)-cyclopropyl]-2-oxo-eth-(E)-ylidene]-1,7,7-trimethyl-bicyclo[2.2.1]heptan-2-one (0.32 g) and hydrazine monohydrate (0.234 g) to give (1S,8R)-5-[1-(4-chloro-phenyl)-cyclopropyl]-1,11,11-trimethyl-3,4-diaza-tricyclo[6.2.1.0$^{2,7}$]undeca-2,4,6-triene (0.134 g) as an off-white solid. MS (EI): 338.2 (M$^+$).

Example 23

(1S,8R)-5-[1-(4-Chloro-phenyl)-cyclobutyl]-1,11,11-trimethyl-3,4-diaza-tricyclo [6.2.1.0$^{2,7}$]undeca-2,4,6-triene

Step A]: {2-[1-(4-Chloro-phenyl)-cyclobutyl]-2-oxo-ethyl}-phosphonic acid dimethyl ester This material was obtained in analogy to example 1 step A] from 1-(4-chloro-phenyl)-cyclobutanecarboxylic acid methyl ester (5.493 g) and methyl-phosphonic acid dimethyl ester (6.067 g) to give {2-[1-(4-chloro-phenyl)-cyclobutyl]-2-oxo-ethyl]-phosphonic acid dimethyl ester (7.458 g) as an off-white liquid. MS (ESI): 317.3 (MH$^+$).

Step B]: (1S,4R)-3-[2-[1-(4-Chloro-phenyl)-cyclobutyl]-2-oxo-eth-(E)-ylidene]-1,7,7-trimethyl-bicyclo[2.2.1]heptan-2-one In analogy to example 1 step B] on reaction of {2-[1-(4-chloro-phenyl)-cyclobutyl]-2-oxo-ethyl}-phosphonic acid dimethyl ester (0.48 g) and (1S,4R)-1,7,7-trimethyl-bicyclo[2.2.1]heptane-2,3-dione (0.2 g) there was obtained (1S,4R)-3-[2-[1-(4-chloro-phenyl)-cyclobutyl]-2-oxo-eth-(E)-ylidene]-1,7,7-trimethyl-bicyclo[2.2.1]heptan-2-one (0.347 g) as a light yellow oil. MS (EI): 357.2 (MH$^+$).

Step C]: (1S,8R)-5-[1-(4-Chloro-phenyl)-cyclobutyl]-1,11,11-trimethyl-3,4-diaza-tricyclo[6.2.1.0$^{2,7}$] undeca-2,4,6-triene This material was obtained in analogy to example 1 steps C] from (1S,4R)-3-[2-[1-(4-chloro-phenyl)-cyclobutyl]-2-oxo-eth-(E)-ylidene]-1,7,7-trimethyl-bicyclo[2.2.1]heptan-2-one (0.33 g) and hydrazine monohydrate (0.231 g) to give (1S,8R)-5-[1-(4-Chloro-phenyl)-cyclobutyl]-1,11,11-trimethyl-3,4-diaza-tricyclo[6.2.1.0$^{2,7}$]undeca-2,4,6-triene (0.033 g) as an off-white solid. MS (EI): 352.1 (M$^+$).

Example 24

3-Adamantan-1-yl-5,6,7,8-tetrahydro-cinnoline

Step A]: 2-[2-Adamantan-1-yl-2-oxo-eth-(E)-ylidene]-cyclohexanone

This material was obtained in analogy to example 1 step B] from 2-adamantan-1-yl-2-oxo-ethyl)-phosphonic acid dimethyl ester (0.894 g) and cyclohexane-1,2-dione (0.35 g) to give 2-[2-adamantan-1-yl-2-oxo-eth-(E)-ylidene]-cyclohexanone (0.173 g) as a light yellow amorphous solid. MS (EI): 272.3 (M$^+$).

Step B]: 3-Adamantan-1-yl-5,6,7,8-tetrahydro-cinnoline

This material was obtained in analogy to example 4 steps C] from 2-[2-adamantan-1-yl-2-oxo-eth-(E)-ylidene]-cyclohexanone (0.13 g) and hydrazine monohydrate (0.119 g) to give 3-adamantan-1-yl-5,6,7,8-tetrahydro-cinnoline (0.037 g) as a light yellow amorphous solid. MS (EI): 268.3 (M$^+$).

Example 25

3-(1-Phenyl-5-trifluoromethyl-1H-pyrazol-4-yl)-5,6,7,8-tetrahydro-cinnoline

Step A]: 2-[2-Oxo-2-(1-phenyl-5-trifluoromethyl-1H-pyrazol-4-yl)-eth-(E)-ylidene]-cyclohexanone This material was obtained in analogy to example 1 step B] from [2-oxo-2-(1-phenyl-5-trifluoromethyl-1H-pyrazol-4-yl)-ethyl]-phosphonic acid dimethyl ester (0.646 g) and cyclohexane-1,2-dione (0.4 g) to give 2-[2-oxo-2-(1-phenyl-5-trifluoromethyl-1H-pyrazol-4-yl)-eth-(E)-ylidene]-cyclohexanone (0.504 g) as a light yellow oil. MS (ESI): 348.1 (M$^+$).

Step B]: 3-(1-Phenyl-5-trifluoromethyl-1H-pyrazol-4-yl)-5,6,7,8-tetrahydro-cinnoline This material was obtained in analogy to example 1 steps C], without NaOMe treatment, from 2-[2-oxo-2-(1-phenyl-5-trifluoromethyl-1H-pyrazol-4-yl)-eth-(E)-ylidene]-cyclohexanone (0.48 g) and hydrazine monohydrate (0.345 g) to give 3-(1-phenyl-5-trifluoromethyl-1H-pyrazol-4-yl)-5,6,7,8-tetrahydro-cinnoline (0.188 g) as an off-white solid. MS (EI): 344.1 (M$^+$).

Example 26

3-[1-(4-Chloro-phenyl)-cyclopropyl]-5,6,7,8-tetrahydro-cinnoline

Step A]: 2-{2-[1-(4-Chloro-phenyl)-cyclopropyl]-2-oxo-ethyl}-cyclohex-2-enone In analogy to example 1 step B] on reaction of {2-[1-(4-chloro-phenyl)-cyclopropyl]-2-oxo-ethyl}-phosphonic acid dimethyl ester (0.594 g) and cyclohexane-1,2-dione (0.2 g) there was obtained 2-{2-[1-(4-Chloro-phenyl)-cyclopropyl]-2-oxo-ethyl}-cyclohex-2-enone (0.097 g) as a light yellow oil. MS (EI): 388.1 (M$^+$)

Step B]: 3-[1-(4-Chloro-phenyl)-cyclopropyl]-5,6,7,8-tetrahydro-cinnoline

This material was obtained in analogy to example 1 steps C] from 2-{2-[1-(4-chloro-phenyl)-cyclopropyl]-2-oxo-ethyl}-cyclohex-2-enone (0.09 g) and hydrazine monohydrate (0.078 g), without the NaOMe treatment, to give 3-[1-(4-chloro-phenyl)-cyclopropyl]-5,6,7,8-tetrahydro-cinnoline (0.067 g) as an off-white solid. MS (EI): 274.2 (M$^+$).

Example 27

3-[1-(4-Chloro-phenyl)-cyclobutyl]-5,6,7,8-tetrahydro-cinnoline

Step A: 2-{2-[1-(4-Chloro-phenyl)-cyclobutyl]-2-oxo-ethyl}-cyclohex-2-enone

In analogy to example 1 step B] on reaction of {2-[1-(4-chloro-phenyl)-cyclobutyl]-2-oxo-ethyl}-phosphonic acid dimethyl ester (0.653 g) and cyclohexane-1,2-dione (0.2 g) there was obtained 2-{2-[1-(4-chloro-phenyl)-cyclobutyl]-2-oxo-ethyl}-cyclohex-2-enone (0.078 g) as a light yellow oil. MS (EI): 303 (MH$^+$)

Step B]: 3-[1-(4-Chloro-phenyl)-cyclopropyl]-5,6,7,
8-tetrahydro-cinnoline

This material was obtained in analogy to example 1 steps C] from 2-{2-[1-(4-chloro-phenyl)-cyclobutyl]-2-oxo-ethyl}-cyclohex-2-enone (0.07 g) and hydrazine monohydrate (0.0588 g), without the NaOMe treatment, to give 3-[1-(4-Chloro-phenyl)-cyclopropyl]-5,6,7,8-tetrahydro-cinnoline (0.045 g) as an off-white solid. MS (EI): 298.2 (M$^+$).

Example 28

3-(2-Trifluoromethyl-phenyl)-6,7,8,9-tetrahydro-5H-cyclohepta[c]pyridazine

Step A: 2-[2-Oxo-2-(2-trifluoromethyl-phenyl)-ethyl]-cyclohept-2-enone

In analogy to example 1 step B] on reaction of 2-oxo-2-(2-trifluoromethyl-phenyl)-ethyl]-phosphonic acid dimethyl ester (0.296 g) and cycloheptane-1,2-dione (0.252 g)—synthesis according to R. W. Vander Haar, J. Org. Chem. 14, 1949, 836—there was obtained 2-[2-oxo-2-(2-trifluoromethyl-phenyl)-ethyl]-cyclohept-2-enone (0.03 g) as a yellow oil. MS (EI): 296.1 (MH$^+$)

Step B]: 3-(2-Trifluoromethyl-phenyl)-6,7,8,9-tetrahydro-5H-cyclohepta[c]pyridazine This material was obtained in analogy to example 1 steps C] from 2-[2-oxo-2-(2-trifluoromethyl-phenyl)-ethyl]-cyclohept-2-enone (0.03 g) and hydrazine monohydrate (0.025 g), without the NaOMe treatment, to give 3-(2-trifluoromethyl-phenyl)-6,7,8,9-tetrahydro-5H-cyclohepta[c]pyridazine (0.017 g) as a light-brown oil. MS (ESI): 293.2 (M$^+$).

Example 29

3-[1-(4-Chloro-phenyl)-5-trifluoromethyl-1H-pyrazol-4-yl]-6,7,8,9-tetrahydro-5H-cyclohepta[c]pyridazine Step A: 2-{2-[1-(4-Chloro-phenyl)-5-trifluoromethyl-1H-pyrazol-4-yl]-2-oxo-ethyl}-cyclohept-2-enone In analogy to example 1 step B] on reaction of {2-[1-(4-chloro-phenyl)-5-trifluoromethyl-1H-pyrazol-4-yl]-2-oxo-ethyl}-phosphonic acid dimethyl ester (0.334 g) and cycloheptane-1,2-dione (0.2 g) there was obtained 2-{2-[1-(4-chloro-phenyl)-5-trifluoromethyl-1H-pyrazol-4-yl]-2-oxo-ethyl}-cyclohept-2-enone (0.034 g) as a yellow solid. MS (EI): 396.0 (M$^+$)

Step C]: 3-[1-(4-Chloro-phenyl)-5-trifluoromethyl-1H-pyrazol-4-yl]-6,7,8,9-tetrahydro-5H-cyclohepta[c]pyridazine This material was obtained in analogy to example 1 steps C] from 2-{2-[1-(4-chloro-phenyl)-5-trifluoromethyl-1H-pyrazol-4-yl]-2-oxo-ethyl}-cyclohept-2-enone (0.03 g) and hydrazine monohydrate (0.019 g), without the NaOMe treatment, to give 3-[1-(4-Chloro-phenyl)-5-trifluoromethyl-1H-pyrazol-4-yl]-6,7,8,9-tetrahydro-5H-cyclohepta[c]pyridazine (0.007 g) as a light-brown oil. MS (ESI): 394.1 (MH$^+$).

Example 30

3-[1-(4-Chloro-phenyl)-cyclopropyl]-6,7,8,9-tetrahydro-5H-cyclohepta[c]pyridazine Step A: 2-{2-[1-(4-Chloro-phenyl)-cyclopropyl]-2-oxo-ethyl}-cyclohept-2-enone In analogy to example 1 step B] on reaction of {2-[1-(4-chloro-phenyl)-cyclopropyl]-2-oxo-ethyl}-phosphonic acid dimethyl ester (0.319 g) and cycloheptane-1,2-dione (0.631 g) there was obtained 2-{2-[1-(4-Chloro-phenyl)-cyclopropyl]-2-oxo-ethyl}-cyclohept-2-enone (0.157 g) as a yellow oil. MS (ESI): 304.2.0 (M$^+$)

Step B]: 3-[1-(4-Chloro-phenyl)-cyclopropyl]-6,7,8,9-tetrahydro-5H-cyclohepta[c]pyridazine This material was obtained in analogy to example 1 steps C] from 2-{2-[1-(4-chloro-phenyl)-cyclopropyl]-2-oxo-ethyl}-cyclohept-2-enone (0.14 g) and hydrazine monohydrate (0.116 g), without the NaOMe treatment, to give 3-[1-(4-chloro-phenyl)-cyclopropyl]-6,7,8,9-tetrahydro-5H-cyclohepta[c]pyridazine (0.097 g) as an off-white solid. MS (EI): 298.2 (M$^+$).

Example 31

3-[1-(4-Chloro-phenyl)-cyclobutyl]-6,7,8,9-tetrahydro-5H-cyclohepta[c]pyridazine Step A: 2-{2-[1-(4-Chloro-phenyl)-cyclobutyl]-2-oxo-ethyl}-cyclohept-2-enone In analogy to example 1 step B] on reaction of {2-[1-(4-chloro-phenyl)-cyclobutyl]-2-oxo-ethyl}-phosphonic acid dimethyl ester (0.317 g) and cycloheptane-1,2-dione (0.631 g) there was obtained 2-{2-[1-(4-chloro-phenyl)-cyclobutyl]-2-oxo-ethyl}-cyclohept-2-enone (0.086 g) as a yellow oil. MS (ESI): 317.2 (MH$^+$)

Step B]: 3-[1-(4-Chloro-phenyl)-cyclobutyl]-6,7,8,9-tetrahydro-5H-cyclohepta[c]pyridazine This material was obtained in analogy to example 1 steps C] from 2-{2-[1-(4-chloro-phenyl)-cyclobutyl]-2-oxo-ethyl}-cyclohept-2-enone (0.075 g) and hydrazine monohydrate (0.059 g), without the NaOMe treatment, to give 3-[1-(4-chloro-phenyl)-cyclobutyl]-6,7,8,9-tetrahydro-5H-cyclohepta[c]pyridazine (0.041 g) as an off-white solid. MS (EI): 312.2 (M$^+$).

Example 32

3-(5-Fluoro-2-trifluoromethyl-phenyl)-6,7,8,9-tetrahydro-5H-cyclohepta[c]pyridazine Step A]: [2-(5-Fluoro-2-trifluoromethyl-phenyl)-2-oxo-ethyl]-phosphonic acid dimethyl ester This material was obtained in analogy to example 1 step A] from 5-fluoro-2-trifluoromethyl-benzoic acid methyl ester (3.659 g) and methyl-phosphonic acid dimethyl ester (4.087 g) to give [2-(5-fluoro-2-trifluoromethyl-phenyl)-2-oxo-ethyl]-phosphonic acid dimethyl ester (5.418 g) as a light yellow oil that was used without further purification in the next step. MS (ESI): 314.9 (MH$^+$).

Step B: 2-[2-(5-Fluoro-2-trifluoromethyl-phenyl)-2-oxo-ethyl]-cyclohept-2-enone In analogy to example 1 step B] on reaction of [2-(5-fluoro-2-trifluoromethyl-phenyl)-2-oxo-ethyl]-phosphonic acid dimethyl ester (0.598 g) and cycloheptane-1,2-dione (0.2 g) there was obtained 2-[2-(5-fluoro-2-trifluoromethyl-phenyl)-2-oxo-ethyl]-cyclohept-2-enone (0.092 g) as a yellow oil. MS (EI): 314.1 (M$^+$)

Step C]: 3-(5-Fluoro-2-trifluoromethyl-phenyl)-6,7,8,9-tetrahydro-5H-cyclohepta[c]pyridazine This material was obtained in analogy to example 1 steps C] from 2-[2-(5-Fluoro-2-trifluoromethyl-phenyl)-2-oxo-ethyl]-cyclohept-2-enone (0.07 g) and hydrazine monohydrate (0.056 g), without the NaOMe treatment, to give 3-(5-fluoro-2-trifluoromethyl-phenyl)-6,7,8,9-tetrahydro-5H-cyclohepta[c]pyridazine (0.058 g) as a light yellow solid. MS (EI): 310.1 (M$^+$).

Example 33

(1S,8R)-5-[1-(4-Fluoro-phenyl)-5-trifluoromethyl-1H-pyrazol-4-yl]-1,11,11-trimethyl-3,4-diazatricyclo[6.2.1.0$^{2,7}$]undeca-2(7),3,5-triene

Step A]: {2-[1-(4-Fluoro-phenyl)-5-trifluoromethyl-1H-pyrazol-4-yl]-2-oxo-ethyl}-phosphonic acid dimethyl ester This material was obtained in analogy to example 1 step A] from 1-(4-fluoro-phenyl)-5-trifluoromethyl-1H-pyrazole-4-carboxylic acid ethyl ester (5.0 g) and methyl-phosphonic acid dimethyl ester (3.923 g) to give {2-[1-(4-fluoro-phenyl)-5-trifluoromethyl-1H-pyrazol-4-yl]-2-oxo-ethyl}-phosphonic acid dimethyl ester (6.635 g) as a light brown oil that was used without further purification in the next step. MS (ESI): 381.1 (MH$^+$).

Step B: (1S,4R)-3-{2-[1-(4-Fluoro-phenyl)-5-trifluoromethyl-1H-pyrazol-4-yl]-2-oxo-eth-(E)-ylidene}-1,7,7-trimethyl-bicyclo[2.2.1]heptan-2-one This material was obtained in analogy to example 1 step B] from {2-[1-(4-fluoro-phenyl)-5-trifluoromethyl-1H-pyrazol-4-yl]-2-oxo-ethyl}-phosphonic acid dimethyl ester (0.4 g) and (1S,4R)-1,7,7-trimethyl-bicyclo[2.2.1]heptane-2,3-dione (0.175 g) to give (1S,4R)-3-{2-[1-(4-fluoro-phenyl)-5-trifluoromethyl-1H-pyrazol-4-yl]-2-oxo-eth-(E)-ylidene}-1,7,7-trimethyl-bicyclo[2.2.1]heptan-2-one (0.082 g) as a yellow oil. MS (ESI): 420.2 (MH$^+$).

Step C]: (1S,8R)-5-[1-(4-Fluoro-phenyl)-5-trifluoromethyl-1H-pyrazol-4-yl]-1,11,11-trimethyl-3,4-diazatricyclo[6.2.1.0$^{2,7}$]undeca-2(7),3,5-triene This material was obtained in analogy to example 1 steps C] from (1S,4R)-3-{2-[1-(4-fluoro-phenyl)-5-trifluoromethyl-1H-pyrazol-4-yl]-2-oxo-eth-(E)-ylidene}-1,7,7-trimethyl-bicyclo[2.2.1]heptan-2-one (0.082 g) and hydrazine monohydrate (0.049 g) to give (1S,8R)-5-[1-(4-Fluoro-phenyl)-5-trifluoromethyl-1H-pyrazol-4-yl]-1,11,11-trimethyl-3,4-diazatricyclo[6.2.1.0$^{2,7}$]undeca-2(7),3,5-triene (0.025 g) as a yellow solid. MS (ESI): 417.0 (MH$^+$).

Example 34

(1S,8R)-5-Cyclopropyl-1,11,11-trimethyl-3,4-diazatricyclo[6.2.1.0$^{2,7}$]undeca-2(7),3,5-triene

Step A]: (2-Cyclopropyl-2-oxo-ethyl)-phosphonic acid dimethyl ester

This material was obtained in analogy to example 1 step A] from cyclopropanecarboxylic acid methyl ester (4.0 g) and methyl-phosphonic acid dimethyl ester (9.914 g) to give (2-cyclopropyl-2-oxo-ethyl)-phosphonic acid dimethyl ester (1.546 g) as a colorless liquid. MS (ESI): 193.0 (MH$^+$).

Step B: (1S,4R)-3-[2-Cyclopropyl-2-oxo-eth-(E)-ylidene]-1,7,7-trimethyl-bicyclo[2.2.1]heptan-2-one This material was obtained in analogy to example 1 step B] from (2-cyclopropyl-2-oxo-ethyl)-phosphonic acid dimethyl ester (0.416 g) and (1S,4R)-1,7,7-trimethyl-bicyclo[2.2.1]heptane-2,3-dione (0.3 g) to give (1S,4R)-3-[2-cyclopropyl-2-oxo-eth-(E)-ylidene]-1,7,7-trimethyl-bicyclo[2.2.1]heptan-2-one (0.315 g) as a yellow oil. MS (EI): 232.1 (M$^+$).

Step C]: (1S,8R)-5-Cyclopropyl-1,1111-trimethyl-3,4-diaza-tricyclo[6.2.1.0$^{2,7}$]undeca-2(7),3,5-triene This material was obtained in analogy to example 1 steps C] from (1S,4R)-3-[2-cyclopropyl-2-oxo-eth-(E)-ylidene]-1,7,7-trimethyl-bicyclo[2.2.1]heptan-2-one (0.3 g) and hydrazine monohydrate (0.323 g) to give (1S,8R)-5-cyclopropyl-1,11,11-trimethyl-3,4-diaza-tricyclo[6.2.1.0$^{2,7}$]undeca-2(7),3,5-triene (0.168 g) as a white solid. MS (EI): 228.2 (M$^+$).

Example 35

3,4-Dicyclopropyl-6-(5-methyl-1-phenyl-1H-pyrazol-4-yl)-pyridazine

Step A: (E or Z)-1,2-Dicyclopropyl-4-(5-methyl-1-phenyl-1H-pyrazol-4-yl)-but-2-ene-1,4-dione This material was obtained in analogy to example 1 step B] from [2-(5-Methyl-1-phenyl-1H-pyrazol-4-yl)-2-oxo-ethyl]-phosphonic acid dimethyl ester (0.459 g) and 1,2-dicyclopropyl-ethane-1,2-dione (0.245 g)—preparation according to J. Kelder, Synth. Commun., 2, 1972, 125—to give (E or Z)-1,2-dicyclopropyl-4-(5-methyl-1-phenyl-1H-pyrazol-4-yl)-but-2-ene-1,4-dione (0.175 g) as a crystalline off-white solid. MS (ESI): 321.1 (M$^+$)—and the other double bond isomer, isolated by chromatography as less polar component (according to TLC analysis): (Z or E)-1,2-dicyclopropyl-4-(5-methyl-1-phenyl-1H-pyrazol-4-yl)-but-2-ene-1,4-dione (0.053 g). MS (ESI): 321.1 (M$^+$).

Step B]: 3,4-Dicyclopropyl-6-(5-methyl-1-phenyl-1H-pyrazol-4-yl)-pyridazine

This material was obtained in analogy to example 1 steps C], without treatment with NaOMe, from (E or Z)-1,2-dicyclopropyl-4-(5-methyl-1-phenyl-1H-pyrazol-4-yl)-but-2-ene-1,4-dione-0.17 g, main isomer of step B] above—and hydrazine monohydrate (0.266 g) to give 3,4-dicyclopropyl- 6-(5-methyl-1-phenyl-1H-pyrazol-4-yl)-pyridazine (0.12 g) as a crystalline off-white solid. MS (ESI): 316.9 (MH+).

Example 36

3,4-Dicyclopropyl-6-(2-trifluoromethyl-phenyl)-pyridazine

Step A: (Z/E)-1,2-Dicyclopropyl-4-(2-trifluoromethyl-phenyl)-but-2-ene-1,4-dione This material was obtained in analogy to example 1 step B] from 2-oxo-2-(2-trifluoromethyl-phenyl)-ethyl]-phosphonic acid dimethyl ester (0.462 g) and 1,2-dicyclopropyl-ethane-1,2-dione (0.18 g) to give (Z/E)-1,2-dicyclopropyl-4-(2-trifluoromethyl-phenyl)-but-2-ene-1,4-dione (0.275 g) as a Z/E: 2.3/1 mixture (according to NMR analysis), crystalline light yellow solid. MS (ESI): 308.2

Step B]: 3,4-Dicyclopropyl-6-(2-trifluoromethyl-phenyl)-pyridazine

This material was obtained in analogy to example 1 steps C from (Z/E)-1,2-dicyclopropyl-4-(2-trifluoromethyl-phenyl)-but-2-ene-1,4-dione (0.28 g, Z/E mixture described above) and hydrazine monohydrate (0.455 g) to give 3,4-dicyclopropyl-6-(2-trifluoromethyl-phenyl)-pyridazine (0.049 g) as an off-white crystalline solid. MS (ESI): 305.1 (MH+).

Example 37

6-[1-(4-Chloro-phenyl)-cyclopropyl]-3,4-dicyclopropyl-pyridazine

Step A: (E/Z)-4-[1-(4-Chloro-phenyl)-cyclopropyl]-1,2-dicyclopropyl-but-2-ene-1,4-dione This material was obtained in analogy to example 1 step B] from {2-[1-(4-Chloro-phenyl)-cyclopropyl]-2-oxo-ethyl}-phosphonic acid dimethyl ester (0.492 g) and 1,2-dicyclopropyl-ethane-1,2-dione (0.18 g) to give (Z/E)-4-[1-(4-chloro-phenyl)-cyclopropyl]-1,2-dicyclopropyl-but-2-ene-1,4-dione (0.306 g) as a Z/E: 3/1 mixture (according to NMR analysis), crystalline light yellow solid. MS (ESI): 314.2

Step B]: 6-[1-(4-Chloro-phenyl)-cyclopropyl]-3,4-dicyclopropyl-pyridazine

This material was obtained in analogy to example 1 steps C, without NaOMe treatment, from (Z/E)-4-[1-(4-chloro-phenyl)-cyclopropyl]-1,2-dicyclopropyl-but-2-ene-1,4-dione (0.3 g, Z/E mixture described above) and hydrazine monohydrate (0.477 g) to give 6-[1-(4-chloro-phenyl)-cyclopropyl]-3,4-dicyclopropyl-pyridazine (0.164 g) as a white crystalline solid. MS (ESI): 311 (MH+).

Example 38

6-[1-(4-Chloro-phenyl)-cyclobutyl]-3,4-dicyclopropyl-pyridazine

Step A: (Z/E)-4-[1-(4-Chloro-phenyl)-cyclobutyl]-1,2-dicyclopropyl-but-2-ene-1,4-dione This material was obtained in analogy to example 1 step B] from {2-[1-(4-chloro-phenyl)-cyclobutyl]-2-oxo-ethyl}-phosphonic acid dimethyl ester (0.494 g) and 1,2-dicyclopropyl-ethane-1,2-dione (0.18 g) to give a mixture (Z/E)-4-[1-(4-chloro-phenyl)-cyclobutyl]-1,2-dicyclopropyl-but-2-ene-1,4-dione (0.265 g)as Z/E: 4/1 mixture (according to NMR analysis), light yellow solid. MS (ESI): 329.4

Step B]: 6-[1-(4-Chloro-phenyl)-cyclobutyl]-3,4-dicyclopropyl-pyridazine

This material was obtained in analogy to example 1 steps C, without NaOMe treatment, from (Z/E)-4-[1-(4-Chloro-phenyl)-cyclobutyl]-1,2-dicyclopropyl-but-2-ene-1,4-dione (0.26 g, Z/E mixture described above) and hydrazine monohydrate (0.396 g) to give 6-[1-(4-Chloro-phenyl)-cyclobutyl]-3,4-dicyclopropyl-pyridazine (0.129 g) as a white crystalline solid. MS (ESI): 325.1 (MH+).

Example 39

(1SR,8RS)-5-(5-Methyl-1-phenyl-1H-pyrazol-4-yl)-3,4-diaza-tricyclo[6.2.1.0$^{2,7}$]undeca-2(7),3,5-triene Step A: (1SR,4RS)-3-[2-(5-Methyl-1-phenyl-1H-pyrazol-4-yl)-2-oxo-eth-(E)-ylidene]-bicyclo[2.2.1]heptan-2-one This material was obtained in analogy to example 1 step B]] from [2-(5-methyl-1-phenyl-1H-pyrazol-4-yl)-2-oxo-ethyl]-phosphonic acid dimethyl ester (0.386 g) and bicyclo[2.2.1]heptane-2,3-dione (0.135 g)—preparation described by Alder et al, Justus Liebigs Ann. Chem., 593, 1955, 1, 17—to give (1SR,4RS)-3-[2-(5-methyl-1-phenyl-1H-pyrazol-4-yl)-2-oxo-eth-(E)-ylidene]-bicyclo[2.2.1]heptan-2-one (0.155 g) as a yellow gum. MS (ESI): 307.2

Step B]: (1SR,8RS)-5-(5-Methyl-1-phenyl-1H-pyrazol-4-yl)-3,4-diaza-tricyclo[6.2.1.0$^{2,7}$]undeca-2(7),3,5-triene This material was obtained in analogy to example 1 steps C, without NaOMe treatment, from (1SR,4RS)-3-[2-(5-Methyl-1-phenyl-1H-pyrazol-4-yl)-2-oxo-eth-(E)-ylidene]-bicyclo[2.2.1]heptan-2-one (0.15 g) and hydrazine monohydrate (0.245 g) to give 1SR,8RS)-5-(5-Methyl-1-phenyl-1H-pyrazol-4-yl)-3,4-diaza-tricyclo[6.2.1.0$^{2,7}$]undeca-2(7),3,5-triene (0.085 g) as a white crystalline solid. MS (ESI): 303.1 (MH+).

Example 40

(1SR,8RS)-5-(2-Trifluoromethyl-phenyl)-3,4-diaza-tricyclo[6.2.1.0$^{2,7}$]undeca-2(7),3,5-triene Step A: (E or Z)-(1SR,4RS)-3-[2-Oxo-2-(2-trifluoromethyl-phenyl)-ethylidene]-bicyclo[2.2.1]heptan-2-one This material was obtained in analogy to example 1 step B]] from 2-oxo-2-(2-trifluoromethyl-phenyl)-ethyl]-phosphonic acid dimethyl ester (0.573 g) and bicyclo[2.2.1]heptane-2,3-dione (0.2 g) to give: (E or Z)-(1SR,4RS)-3-[2-oxo-2-(2-trifluoromethyl-phenyl)-ethylidene]-bicyclo[2.2.1]heptan-2-one (0.39 g) as a yellow gum. MS (EI): 294.1

Step B]: (1SR,8RS)-5-(2-Trifluoromethyl-phenyl)-3,
4-diaza-tricyclo[6.2.1.0$^{2,7}$]undeca-2(7),3,5-triene This material was obtained in analogy to example 1 steps C, without NaOMe treatment, from (E or Z)-(1SR,4RS)-3-[2-Oxo-2-(2-trifluoromethyl-phenyl)-ethylidene]-bicyclo[2.2.1]heptan-2-one (0.39 g) and hydrazine monohydrate (0.663 g) to give (1SR,8RS)-5-(2-Trifluoromethyl-phenyl)-3,4-diaza-tricyclo[6.2.1.0$^{2,7}$]undeca-2(7),3,5-triene (0.23 g) as a light yellow gum. MS (EI): 290.2 (M$^+$).

Submission of the racemate to preparative HPLC, using a chiral column, Chiral Cel OD, with 95% heptane/isopropanol as eluent, gave the two enantiomers separated, in optically pure form.

Example 41

3-(2-Trifluoromethyl-phenyl)-5,6,7,8,9,10-hexahydro-cycloocta[c]pyridazine

Step A: 2-[2-Oxo-2-(2-trifluoromethyl-phenyl)-ethyl]-cyclooct-2-enone

This material was obtained in analogy to example 1 step B]] from 2-oxo-2-(2-trifluoromethyl-phenyl)-ethyl]-phosphonic acid dimethyl ester (0.634 g) and cyclooctane-1,2-dione (0.25 g)—preparation described by H. Meier, Synthesis, 1971, 215—to give: (Z)-2-[2-oxo-2-(2-trifluoromethyl-phenyl)-ethyl]-cyclooct-2-enone (0.23 g) as a light yellow solid. MS (EI): 310.1

Step B]: 3-(2-Trifluoromethyl-phenyl)-5,6,7,8,9,10-hexahydro-cycloocta[c]pyridazine This material was obtained in analogy to example 1 steps C], without NaOMe treatment, from (Z)-2-[2-oxo-2-(2-trifluoromethyl-phenyl)-ethyl]-cyclooct-2-enone (0.231 g) and hydrazine monohydrate (0.187 g) to give 3-(2-Trifluoromethyl-phenyl)-5,6,7,8,9,10-hexahydro-cycloocta[c]pyridazine (0.128 g) as an off-white solid. MS (EI): 306.2 (M$^+$).

Example 42

(1S,8R)-5-(3-Fluoro-2-trifluoromethyl-phenyl)-1,11,11-trimethyl-3,4-diaza-tricyclo[6.2.1.0$^{2,7}$]undeca-2,4,6-triene Step A]: [2-(3-Fluoro-2-trifluoromethyl-phenyl)-2-oxo-ethyl]-phosphonic acid dimethyl ester This material was obtained in analogy to example 1 step A] from 3-fluoro-2-trifluoromethyl-benzoic acid methyl ester (2.4 g) and methyl-phosphonic acid dimethyl ester (2.68 g) to give [2-(3-fluoro-2-trifluoromethyl-phenyl)-2-oxo-ethyl]-phosphonic acid dimethyl ester (2.7 g) as a colorless liquid. MS (ESI): 315.0 (MH$^+$).

Step B]: (1S,4R)-3-[2-(3-Fluoro-2-trifluoromethyl-phenyl)-2-oxo-eth-(E)-ylidene-]1,7,7-trimethyl-bicyclo[2.2.1]heptan-2-one This material was obtained in analogy to example 1 step B] from [2-(3-Fluoro-2-trifluoromethyl-phenyl)-2-oxo-ethyl]-phosphonic acid dimethyl ester (0.454 g) and (1S,4R)-1,7,7-trimethyl-bicyclo[2.2.1]heptane-2,3-dione (0.2 g) to give (1S,4R)-3-[2-(3-fluoro-2-trifluoromethyl-phenyl)-2-oxo-eth-(E)-ylidene]-1,7,7-trimethyl-bicyclo[2.2.1]heptan-2-one (0.115 g) as a yellow solid. MS (EI): 354.2 (M$^+$).

Step C]: (1S,8R)-5-(3-Fluoro-2-trifluoromethyl-phenyl)-1,11,11-trimethyl-3,4-diaza-tricyclo[6.2.1.0$^{2,7}$]undeca-2,4,6-triene This material was obtained in analogy to example 1 step C], without the NaOMe treatment, from (1S,4R)-3-[2-(3-Fluoro-2-trifluoromethyl-phenyl)-2-oxo-eth-(E)-ylidene]-1,7,7-trimethyl-bicyclo[2.2.1]heptan-2-one (0.105 g) and hydrazine monohydrate (0.074 g) to give (1S,8R)-1,11,11-trimethyl-5-(2-trifluoromethyl-phenyl)-3,4-diazatricyclo[6.2.1.0$^{2,7}$]undeca-2(7),3,5-triene (0.008 g) as an off-white light solid. MS (EI): 350.1 (M$^+$).

Example 43

3-(3-Fluoro-2-trifluoromethyl-phenyl)-6,7,8,9-tetrahydro-5H-cyclohepta[c]pyridazine Step A]: 2-[2-(3-Fluoro-2-trifluoromethyl-phenyl)-2-oxo-ethyl]-cyclohept-2-enone This material was obtained in analogy to example 1 step B] from [2-(3-fluoro-2-trifluoromethyl-phenyl)-2-oxo-ethyl]-phosphonic acid dimethyl ester (0.598 g) and cycloheptane-1,2-dione (0.2 g dione (0.2 g) to give 2-[2-(3-fluoro-2-trifluoromethyl-phenyl)-2-oxo-ethyl]-cyclohept-2-enone (0.216 g) as a yellow liquid. MS (EI): 314.1 (M$^+$).

Step B]: 3-(3-Fluoro-2-trifluoromethyl-phenyl)-6,7,8,9-tetrahydro-5H-cyclohepta[c]pyridazine This material was obtained in analogy to example 1 step C], without the NaOMe treatment, from 2-[2-(3-fluoro-2-trifluoromethyl-phenyl)-2-oxo-ethyl]-cyclohept-2-enone (0.2 g) and hydrazine monohydrate (0.159 g) to give 3-(3-Fluoro-2-trifluoromethyl-phenyl)-6,7,8,9-tetrahydro-5H-cyclohepta[c]pyridazine (0.141 g) as a light yellow solid. MS (EI): 310.1 (M$^+$).

Example 44

(1SR,8RS)-5-[1-(4-Fluoro-phenyl)-5-trifluoromethyl-1H-pyrazol-4-yl]-3,4-diaza-tricyclo[6.2.1.0$^{2,7}$]undeca-2,4,6-triene Step A: (1S,4R)-3-[2-[1-(4-Fluoro-phenyl)-5-trifluoromethyl-1H-pyrazol-4-yl]-2-oxo-eth-(E)-ylidene]-bicyclo[2.2.1]heptan-2-one This material was obtained in analogy to example 1 step B]] from [{2-[1-(4-fluoro-phenyl)-5-trifluoromethyl-1H-pyrazol-4-yl]-2-oxo-ethyl}-phosphonic acid dimethyl ester (0.418 g) and bicyclo[2.2.1]heptane-2,3-dione (0.125 g) to give: (1S,4R)-3-[2-[1-(4-fluoro-phenyl)-5-trifluoromethyl-1H-pyrazol-4-yl]-2-oxo-eth-(E)-ylidene]-bicyclo[2.2.1]heptan-2-one (0.26 g) as a yellow solid. MS (EI): 378.1

Step B]: (1SR,8RS)-5-[1-(4-Fluoro-phenyl)-5-trifluoromethyl-1H-pyrazol-4-yl]-3,4-diaza-tricyclo[6.2.1.0$^{2,7}$]undeca-2,4,6-triene This material was obtained in analogy to example 1 steps C], without NaOMe treatment, from (1S,4R)-3-[2-[1-(4-fluoro-phenyl)-5-trifluoromethyl-1H-pyrazol-4-yl]-2-oxoeth-(E)-ylidene]-bicyclo[2.2.1]heptan-2-one (0.26 g) and hydrazine monohydrate (0.344 g) to (1SR,8RS)-5-[1-(4-Fluoro-phenyl)-5-trifluoromethyl-1H-pyrazol-4-yl]-3,4-diaza-tricyclo[6.2.1.0$^{2,7}$]undeca-2,4,6-triene (0.094 g) as a light-yellow crystalline solid. MS (EI): 374.2 (M$^+$).

Example 45

(1SR,8RS)-5-(2,4-Difluoro-phenyl)-3,4-diaza-tricyclo[6.2.1.0$^{2,7}$]undeca-2,4,6-triene Step A: (1SR,4RS)-3-[2-(2,4-Difluoro-phenyl)-2-oxo-eth-(E)-ylidene]-bicyclo[2.2.1]heptan-2-one This material was obtained in analogy to example 1 step B] from [2-(2,4-difluoro-phenyl)-2-oxo-ethyl]-phosphonic acid dimethyl ester (0.219 g) and bicyclo[2.2.1]heptane-2,3-dione (0.124 g) to give (1SR,4RS)-3-[2-(2,4-Difluoro-phenyl)-2-oxo-eth-(E)-ylidene]-bicyclo[2.2.1]heptan-2-one (0.18 g) as a yellow solid. MS (EI): 262.1

Step B]: (1SR,8RS)-5-(2,4-Difluoro-phenyl)-3,4-diaza-tricyclo[6.2.1.0$^{2,7}$]undeca-2,4,6-triene This material was obtained in analogy to example 1 steps C], without NaOMe treatment, from (1SR,4RS)-3-[2-(2,4-Difluoro-phenyl)-2-oxo-eth-(E)-ylidene]-bicyclo[2.2.1]heptan-2-one (0.18 g) and hydrazine monohydrate (0.344 g) to give (1SR,8RS)-5-(2,4-Difluoro-phenyl)-3,4-diaza-tricyclo[6.2.1.0$^{2,7}$]undeca-2,4,6-triene (0.104 g) as a light-yellow crystalline solid. MS (EI): 258.1 (M$^+$).

Example 46

(1SR,8RS)-5-(2-Fluoro-phenyl)-3,4-diaza-tricyclo[6.2.1.0$^{2,7}$]undeca-2,4,6-triene Step A: (1SR,4RS)-3-[2-(2-fluoro-phenyl)-2-oxo-eth-(E)-ylidene]-bicyclo[2.2.1]heptan-2-one This material was obtained in analogy to example 1 step B] from [2-(2-fluoro-phenyl)-2-oxo-ethyl]-phosphonic acid dimethyl ester (0.27 g) and bicyclo[2.2.1]heptane-2,3-dione (0.124 g) to give (1SR,4RS)-3-[2-(2-fluoro-phenyl)-2-oxo-eth-(E)-ylidene]-bicyclo[2.2.1]heptan-2-one (0.20 g) as a yellow gum. MS (EI): 244.1

Step B]: (1SR,8RS)-5-(2-Fluoro-phenyl)-3,4-diaza-tricyclo[6.2.1.0$^{2,7}$]undeca-2,4,6-triene This material was obtained in analogy to example 1 steps C], without NaOMe treatment, from (1SR,4RS)-3-[2-(2-fluoro-phenyl)-2-oxo-eth-(E)-ylidene]-bicyclo[2.2.1]heptan-2-one (0.198 g) and hydrazine monohydrate (0.406 g) to give (1SR,8RS)-5-(2-Fluoro-phenyl)-3,4-diaza-tricyclo[6.2.1.0$^{2,7}$]undeca-2,4,6-triene (0.092 g) as a yellow crystalline solid. MS (EI): 240.2 (M$^+$)

Example 47

(1SR,8RS)-5-(4-Fluoro-2-trifluoromethyl-phenyl)-3,4-diaza-tricyclo[6.2.1.0$^{2,7}$]undeca-2,4,6-triene Step A: [2-(4-Fluoro-2-trifluoromethyl-phenyl)-2-oxo-ethyl]-phosphonic acid dimethyl ester This material was obtained in analogy to example 1 step A] from 4-Fluoro-2-trifluoromethyl-benzoic acid methyl ester (4.468 g) and methyl-phosphonic acid dimethyl ester (4.99 g) to give [2-(4-fluoro-2-trifluoromethyl-phenyl)-2-oxo-ethyl]-phosphonic acid dimethyl ester (5.687 g) as an off-white solid. MS (ESI): 314.9 (MH$^+$).

Step B: (1SR,4RS)-3-[2-(4-Fluoro-2-trifluoromethyl-phenyl)-2-oxo-eth-(E)-ylidene]-bicyclo[2.2.1]heptan-2-one This material was obtained in analogy to example 1 step B]] from [2-(4-fluoro-2-trifluoromethyl-phenyl)-2-oxo-ethyl]-phosphonic acid dimethyl ester (0.346 g) and bicyclo[2.2.1]heptane-2,3-dione (0.124 g) to give (1SR,4RS)-3-[2-(4-Fluoro-2-trifluoromethyl-phenyl)-2-oxo-eth-(E)-ylidene]-bicyclo[2.2.1]heptan-2-one (0.242 g) as a yellow solid. MS (EI): 312.1

Step C]: (1SR,8RS)-5-(4-Fluoro-2-trifluoromethyl-phenyl)-3,4-diaza-tricyclo[6.2.1.0$^{2,7}$]undeca-2,4,6-triene This material was obtained in analogy to example 1 steps C, without NaOMe treatment, from: (1SR,4RS)-3-[2-(4-Fluoro-2-trifluoromethyl-phenyl)-2-oxo-eth-(E)-ylidene]-bicyclo[2.2.1]heptan-2-one (0.238 g) and hydrazine monohydrate (0.382 g) to give (1SR,4RS)-3-[2-(4-Fluoro-2-trifluoromethyl-phenyl)-2-oxo-eth-(E)-ylidene]-bicyclo[2.2.1]heptan-2-one (0.083 g) as a light yellow gum. MS (EI): 308 (M$^+$).

Example 48

3-(3-Trifluoromethyl-1H-pyrazol-4-yl)-5,6,7,8,9,10-hexahydro-cycloocta[c]pyridazine Step A: [2-Oxo-2-(3-trifluoromethyl-1H-pyrazol-4-yl)-ethyl]-phosphonic acid dimethyl ester This material was obtained in analogy to example 1 step A] from 3-trifluoromethyl-1H-pyrazole-4-carboxylic acid ethyl ester (5 g) and methyl-phosphonic acid dimethyl ester (5.585 g) to give [2-oxo-2-(3-trifluoromethyl-1H-pyrazol-4-yl)-ethyl]-phosphonic acid dimethyl ester (5.462 g) as an off-white solid that was used without further purification in the next step. MS (ESI): 286.8 (MH$^+$).

Step B: (Z)-2-[2-Oxo-2-(3-trifluoromethyl-1H-pyrazol-4-yl)-ethyl]-cyclooct-2-enone This material was obtained in analogy to example 1 step B]] from [2-oxo-2-(3-trifluoromethyl-1H-pyrazol-4-yl)-ethyl]-phosphonic acid dimethyl ester (0.612 g) and cyclooctane-1,2-dione (0.25 g) to give (Z)-2-[2-oxo-2-(3-trifluoromethyl-1H-pyrazol-4-yl)-ethyl]-cyclooct-2-enone (0.069 g) as a light-yellow oil. MS (EI): 300(M$^+$).

Step C]: 3-(3-Trifluoromethyl-1H-pyrazol-4-yl)-5,6,7,8,9,10-hexahydro-cycloocta[c]pyridazine This material was obtained in analogy to example 1 steps C], without NaOMe treatment, from (Z)-2-[2-Oxo-2-(3-trifluoromethyl-1H-pyrazol-4-yl)-ethyl]-cyclooct-2-enone (0.06 g) and hydrazine monohydrate (0.05 g) to give 3-(3-trifluoromethyl-1H-pyrazol-4-yl)-5,6,7,8,9,10-hexahydro-cycloocta[c]pyridazine (0.019 g) as an off-white solid. MS (EI): 296.2 (M$^+$).

Example 49

3-(4-Fluoro-2-trifluoromethyl-phenyl)-5,6,7,8,9,10-hexahydro-cycloocta[c]pyridazine

Step A: (Z)-2-[2-(4-Fluoro-2-trifluoromethyl-phenyl)-2-oxo-ethyl]-cyclooct-2-enone This material was obtained in analogy to example 1 step B] from [2-(4-fluoro-2-trifluoromethyl-phenyl)-2-oxo-ethyl]-phosphonic acid dimethyl ester (0.672 g) and cyclooctane-1,2-dione (0.25 g) to give (Z)-2-[2-(4-fluoro-2-trifluoromethyl-phenyl)-2-oxo-ethyl]-cyclooct-2-enone (0.224 g) as a light yellow oil. MS (EI): 328.1(M$^+$).

Step B]: 3-(4-Fluoro-2-trifluoromethyl-phenyl)-5,6,7,8,9,10-hexahydro-cycloocta[c]pyridazine This material was obtained in analogy to example 1 steps C], without NaOMe treatment, from: (Z)-2-[2-(4-fluoro-2-trifluoromethyl-phenyl)-2-oxo-ethyl]-cyclooct-2-enone (0.215 g) and hydrazine monohydrate (0.164 g) to give 3-(4-fluoro-2-trifluoromethyl-phenyl)-5,6,7,8,9,10-hexahydro-cycloocta[c]pyridazine (0.194 g) as an light yellow solid. MS (EI): 324.1 (M$^+$).

Example 50

3-(2-Fluoro-phenyl)-5,6,7,8,9,10-hexahydro-cycloocta[c]pyridazine

Step A: (Z)-2-[2-(2-Fluoro-phenyl)-2-oxo-ethyl]-cyclooct-2-enone

This material was obtained in analogy to example 1 step B] from [2-(2-fluoro-phenyl)-2-oxo-ethyl]-phosphonic acid dimethyl ester (0.527 g) and cyclooctane-1,2-dione (0.25 g) to give (Z)-2-[2-(2-fluoro-phenyl)-2-oxo-ethyl]-cyclooct-2-enone (0.305 g) as a light yellow oil. MS (EI): 260.2 (M$^+$).

Step B]: 3-(2-Fluoro-phenyl)-5,6,7,8,9,10-hexahydro-cycloocta[c]pyridazine

This material was obtained in analogy to example 1 steps C], without NaOMe treatment, from (Z)-2-[2-(2-fluoro-phenyl)-2-oxo-ethyl]-cyclooct-2-enone (0.305 g) and hydrazine monohydrate (0.294 g) to give 3-(2-fluoro-phenyl)-5,6,7,8,9,10-hexahydro-cycloocta[c]pyridazine (0.171 g) as an off-white solid. MS (EI): 256.2 (M$^+$).

Example 51

(1S,8R)-5-(5-Methoxy-2-trifluoromethyl-phenyl)-1,11,11-trimethyl-3,4-diaza-tricyclo[6.2.1.0$^{2,7}$]undeca-2,4,6-triene

Step A]: (1S,4R)-3-[2-(5-Fluoro-2-trifluoromethyl-phenyl)-2-oxo-eth-(E)-ylidene]-1,7,7-trimethyl-bicyclo[2.2.1]heptan-2-one This material was obtained in analogy to example 1 step B] [2-(5-Fluoro-2-trifluoromethyl-phenyl)-2-oxo-ethyl]-phosphonic acid dimethyl ester (0.416 g) and (1S,4R)-1,7,7-trimethyl-bicyclo[2.2.1]heptane-2,3-dione (0.2 g) to give (1S,4R)-3-[2-(5-fluoro-2-trifluoromethyl-phenyl)-2-oxo-eth-(E)-ylidene]-1,7,7-trimethyl-bicyclo[2.2.1]heptan-2-one (0.139 g) as a light yellow oil. MS (EI): 354.1 (M$^+$).

Step B]: (1S,8R)-5-(5-Methoxy-2-trifluoromethyl-phenyl)-1,11,11-trimethyl-3,4-diaza-tricyclo[6.2.1.0$^{2,7}$]undeca-2,4,6-triene This material was obtained in analogy to example 1 step C], whereas at NaOMe treatment fluoro/methoxy exchange occurred, from (1S,4R)-3-[2-(5-fluoro-2-trifluoromethyl-phenyl)-2-oxo-eth-(E)-ylidene]-1,7,7-trimethyl-bicyclo[2.2.1]heptan-2-one (0.12 g) and hydrazine monohydrate (0.082 g) to give (1S,8R)-5-(5-methoxy-2-trifluoromethyl-phenyl)-1,11,11-trimethyl-3,4-diaza-tricyclo[6.2.1.0$^{2,7}$]undeca-2,4,6-triene (0.019 g) as a light yellow solid. MS (EI): 362.2 (M$^+$).

Example 52

3-(5-Methyl-1-phenyl-1H-pyrazol-4-yl)-6,7,8,9-tetrahydro-5H-cyclohepta[c]pyridazine

Step A: 2-[2-(5-Methyl-1-phenyl-1H-pyrazol-4-yl)-2-oxo-ethyl]-cyclohept-2-enone This material was obtained in analogy to example 1 step B] from [2-(5-methyl-1-phenyl-1H-pyrazol-4-yl)-2-oxo-ethyl]-phosphonic acid dimethyl ester (0.357 g) and cycloheptane-1,2-dione (0.133 g) to give 2-[2-(5-Methyl-1-phenyl-1H-pyrazol-4-yl)-2-oxo-ethyl]-cyclohept-2-enone (0.024 g) as a yellow solid. MS (ESI): 309.3 (MH$^+$).

Step B]: 3-(5-Methyl-1-phenyl-1H-pyrazol-4-yl)-6,7,8,9-tetrahydro-5H-cyclohepta[c]pyridazine This material was obtained in analogy to example 1 steps C], without NaOMe treatment, from 2-[2-(5-methyl-1-phenyl-1H-pyrazol-4-yl)-2-oxo-ethyl]-cyclohept-2-enone (0.024 g) and hydrazine monohydrate (0.039 g) to give 3-(5-Methyl-1-phenyl-1H-pyrazol-4-yl)-6,7,8,9-tetrahydro-5H-cyclohepta[c]pyridazine (0.01 g) as a crystalline solid. MS (ESI): 305.1 (MH$^+$).

Example 53

(1S,8R)-5-(4-Fluoro-2-trifluoromethyl-phenyl)-1,11,11-trimethyl-3,4-diaza-tricyclo[6.2.1.0$^{2,7}$]undeca-2,4,6-triene

Step A]: (1S,4R)-3-[2-(4-Fluoro-2-trifluoromethyl-phenyl)-2-oxo-eth-(E)-ylidene]-1,7,7-trimethyl-bicyclo[2.2.1]heptan-2-one This material was obtained in analogy to example 1 step B] from [2-(4-Fluoro-2-trifluoromethyl-phenyl)-2-oxo-ethyl]-phosphonic acid dimethyl ester (0.416 g) and (1S,4R)-1,7,7-trimethyl-bicyclo[2.2.1]heptane-2,3-dione (0.2 g) to give (1S,4R)-3-[2-(4-fluoro-2-trifluoromethyl-phenyl)-2-oxo-eth-(E)-ylidene]-1,7,7-trimethyl-bicyclo[2.2.1]heptan-2-one (0.389 g) as a yellow oil. MS (EI): 354.1 (M$^+$).

Step B]: (1S,8R)-5-(4-Fluoro-2-trifluoromethyl-phenyl)-1,11,11-trimethyl-3,4-diaza-tricyclo[6.2.1.0$^{2,7}$]undeca-2,4,6-triene This material was obtained in analogy to example 1 step C] from (1S,4R)-3-[2-(4-fluoro-2-trifluoromethyl-phenyl)-2-oxo-eth-(E)-ylidene]-1,7,7-trimethyl-bicyclo[2.2.1]heptan-2-one (0.38 g) and hydrazine monohydrate (0.268 g) to give (1S,8R)-5-(4-Fluoro-2-trifluoromethyl-phenyl)-1,11,11-trimethyl-3,4-diaza-tricyclo[6.2.1.0$^{2,7}$]undeca-2,4,6-triene (0.089 g) as an light yellow solid. MS (EI): 350 (M$^+$).

Example 54

3-(2,5-Difluoro-phenyl)-6,7,8,9-tetrahydro-5H-cyclohepta[c]pyridazine

Step A: 2-[2-(2,5-Difluoro-phenyl)-2-oxo-ethyl]-cyclohept-2-enone

In analogy to example 1 step B] on reaction of [2-(2,5-difluoro-phenyl)-2-oxo-ethyl]-phosphonic acid dimethyl ester (0.317 g) and cycloheptane-1,2-dione (0.126 g) there was obtained: 2-[2-(2,5-difluoro-phenyl)-2-oxo-ethyl]-cyclohept-2-enone (0.163 g) as a light brown solid. MS (EI): 264.1 (M$^+$)

Step B]: 3-(2,5-Difluoro-phenyl)-6,7,8,9-tetrahydro-5H-cyclohepta[c]pyridazine

This material was obtained in analogy to example 1 steps C] from 2-[2-(2,5-difluoro-phenyl)-2-oxo-ethyl]-cyclohept-2-enone (0.16 g) and hydrazine monohydrate (0.303 g), without the NaOMe treatment, to give 3-(2,5-difluoro-phenyl)-6,7,8,9-tetrahydro-5H-cyclohepta[c]pyridazine (0.057 g) as a light yellow solid. MS (EI): 260.2 (M$^+$).

Example 55

3-[1-(4-Fluoro-phenyl)-5-trifluoromethyl-1H-pyrazol-4-yl]-6,7,8,9-tetrahydro-5H-cyclohepta[c]pyridazine Step A: 2-{2-[1-(4-Fluoro-phenyl)-5-trifluoromethyl-1H-pyrazol-4-yl]-2-oxo-ethyl}-cyclohept-2-enone In analogy to example 1 step B] on reaction of {2-[1-(4-Fluoro-phenyl)-5-trifluoromethyl-1H-pyrazol-4-yl]-2-oxo-ethyl}-phosphonic acid dimethyl ester (0.456 g) and cycloheptane-1,2-dione (0.126 g) there was obtained 2-{2-[1-(4-fluoro-phenyl)-5-trifluoromethyl-1H-pyrazol-4-yl]-2-oxo-ethyl}-cyclohept-2-enone (0.203 g) as a yellow solid. MS (EI): 380.1 (M$^+$)

Step B]: 3-[1-(4-Fluoro-phenyl)-5-trifluoromethyl-1H-pyrazol-4-yl]-6,7,8,9-tetrahydro-5H-cyclohepta[c]pyridazine This material was obtained in analogy to example 1 steps C] from 2-{2-[1-(4-Fluoro-phenyl)-5-trifluoromethyl-1H-pyrazol-4-yl]-2-oxo-ethyl}-cyclohept-2-enone (0.2 g) and hydrazine monohydrate (0.26 g), without the NaOMe treatment, to give 3-[1-(4-Fluoro-phenyl)-5-trifluoromethyl-1H-pyrazol-4-yl]-6,7,8,9-tetrahydro-5H-cyclohepta[c]pyridazine (0.069 g) as a light brown solid. MS (EI): 376.2 (M$^+$).

Example 56

3-(2,4-Difluoro-phenyl)-6,7,8,9-tetrahydro-5H-cyclohepta[c]pyridazine

Step A: 2-[2-(2,4-Difluoro-phenyl)-2-oxo-ethyl]-cyclohept-2-enone

In analogy to example 1 step B] on reaction of [2-(2,4-difluoro-phenyl)-2-oxo-ethyl]-phosphonic acid dimethyl ester (0.503 g) and cycloheptane-1,2-dione (0.2 g) there was obtained 2-[2-(2,4-difluoro-phenyl)-2-oxo-ethyl]-cyclohept-2-enone (0.12 g) as a yellow oil. MS (EI): 264.1 (M$^+$)

Step B]: 3-(2,4-Difluoro-phenyl)-6,7,8,9-tetrahydro-5H-cyclohepta[c]pyridazine

This material was obtained in analogy to example 1 steps C] from 2-[2-(2,4-Difluoro-phenyl)-2-oxo-ethyl]-cyclohept-2-enone (0.1 g) and hydrazine monohydrate (0.104 g), without the NaOMe treatment, to give 3-(2,4-Difluoro-phenyl)-6,7,8,9-tetrahydro-5H-cyclohepta[c]pyridazine (0.073 g) as a light yellow solid. MS (EI): 260.2 (M$^+$).

Example 57

3-(2-Fluoro-phenyl)-6,7,8,9-tetrahydro-5H-cyclohepta[c]pyridazine

Step A: 2-[2-(2-Fluoro-phenyl)-2-oxo-ethyl]-cyclohept-2-enone

In analogy to example 1 step B] on reaction of [2-(2-fluoro-phenyl)-2-oxo-ethyl]-phosphonic acid dimethyl ester (0.468 g) and cycloheptane-1,2-dione (0.2 g) there was obtained 2-[2-(2-fluoro-phenyl)-2-oxo-ethyl]-cyclohept-2-enone (0.075 g) as a yellow oil. MS (EI): 246.2 (M$^+$)

Step B]: 3-(2-Fluoro-phenyl)-6,7,8,9-tetrahydro-5H-cyclohepta[c]pyridazine

This material was obtained in analogy to example 1 steps C], without NaOMe treatment, from 2-[2-(2-fluoro-phenyl)-2-oxo-ethyl]-cyclohept-2-enone (0.085 g) and hydrazine monohydrate (0.086 g) to give 3-(2-fluoro-phenyl)-6,7,8,9-tetrahydro-5H-cyclohepta[c]pyridazine (0.048 g) as an off-white solid. MS (EI): 242.1 (M$^+$).

Example 58

(1S,8R)-1,11,11-Trimethyl-5-(3-trifluoromethyl-1H-pyrazol-4-yl)-3,4-diaza-tricyclo[6.2.1.0$^{2,7}$]undeca-2,4,6-triene Step A: (1S,4R)-1,7,7-Trimethyl-3-[2-oxo-2-(3-trifluoromethyl-1H-pyrazol-4-yl)-eth-E-ylidene]-bicyclo[2.2.1]heptan-2-one This material was obtained in analogy to example 1 step B] from [2-oxo-2-(3-trifluoromethyl-1H-pyrazol-4-yl)-ethyl]-phosphonic acid dimethyl ester and (1S,4R)-1,7,7-trimethyl-bicyclo[2.2.1]heptane-2,3-dione to give (1S,4R)-1,7,7-Trimethyl-3-[2-oxo-2-(3-trifluoromethyl-1H-pyrazol-4-yl)-eth-E-ylidene]-bicyclo[2.2.1]heptan-2-one that was used without further purification. MS (EI): 326.3 (M$^+$).

Step B]: (1S,8R)-1,11,11-Trimethyl-5-(3-trifluoromethyl-1H-pyrazol-4-yl)-3,4-diaza-tricyclo[6.2.1.0$^{2,7}$]undeca-2,4,6-triene This material was obtained in analogy to example 1 steps C] from (1S,4R)-1,7,7-trimethyl-3-[2-oxo-2-(3-trifluoromethyl-1H-pyrazol-4-yl)-eth-E-ylidene]-bicyclo[2.2.1]heptan-2-one and hydrazine monohydrate to give (1S,8R)-1,11,11-trimethyl-5-(3-trifluoromethyl-1H-pyrazol-4-yl)-3,4-diaza-tricyclo[6.2.1.0$^{2,7}$]undeca-2,4,6-triene as an off-white solid. MS (EI): 322.2 (M$^+$).

Example 59

3-[1-(4-Chloro-phenyl)-cyclopropyl]-5,6,7,8,9,10-hexahydro-cycloocta[c]pyridazine

Step A: (Z)-2-{2-[1-(4-Chloro-phenyl)-cyclopropyl]-2-oxo-ethyl}-cyclooct-2-enone This material was obtained in analogy to example 1 step B] from {2-[1-(4-Chloro-phenyl)-cyclopropyl]-2-oxo-ethyl}-phosphonic acid dimethyl ester (0.432 g) and cyclooctane-1,2-dione (0.2 g) to give (Z)-2-{2-[1-(4-chloro-phenyl)-cyclopropyl]-2-oxo-ethyl}-cyclooct-2-enone (0.146 g) as a yellow oil. MS (EI): 316.2(M$^+$).

Step B]: 3-[1-(4-chloro-phenyl)-cyclopropyl]-5,6,7,8,9,10-hexahydro-cycloocta[c]pyridazine This material was obtained in analogy to example 1 steps C], without NaOMe treatment, from (Z)-2-{2-[1-(4-chloro-phenyl)-cyclopropyl]-2-oxo-ethyl}-cyclooct-2-enone (0.12 g) and hydrazine monohydrate (0.095 g) to give 3-[1-(4-chloro-phenyl)-cyclopropyl]-5,6,7,8,9,10-hexahydro-cycloocta[c]pyridazine (0.067 g) as an off-white solid. MS (EI): 312.3 (M$^+$).

Example 60

(1S,8R)-5-(5-Butoxy-1-methyl-1H-pyrazol-4-yl)-1,11,11-trimethyl-3,4-diaza-tricyclo[6.2.1.0$^{2,7}$]undeca-2,4,6-triene

Step A: [2-(5-Chloro-1-methyl-1H-pyrazol-4-yl)-2-oxo-ethyl]-phosphonic acid dimethyl ester This material was obtained in analogy to example 1 step A] from 5-chloro-1-methyl-1H-pyrazole-4-carboxylic acid ethyl ester (5 g) and methyl-phosphonic acid dimethyl ester (6.578 g) to give [2-(5-chloro-1-methyl-1H-pyrazol-4-yl)-2-oxo-ethyl]-phosphonic acid dimethyl ester (2.18 g) as an off white solid. MS (ESI): 266.9 (MH$^+$).

Step B: (1S,4R)-3-[2-(5-Chloro-1-methyl-1H-pyrazol-4-yl)-2-oxo-eth-(E)-ylidene]-1,7,7-trimethyl-bicyclo[2.2.1]heptan-2-one This material was obtained in analogy to example 1 step B] from [2-(5-chloro-1-methyl-1H-pyrazol-4-yl)-2-oxo-ethyl]-phosphonic acid dimethyl ester (0.577 g) and (1S,4R)-1,7,7-trimethyl-bicyclo[2.2.1]heptane-2,3-dione (0.3 g) to give (1S,4R)-3-[2-(5-chloro-1-methyl-1H-pyrazol-4-yl)-2-oxo-eth-(E)-ylidene]-1,7,7-trimethyl-bicyclo[2.2.1]heptan-2-one (0.534 g) as a yellow solid. MS (EI): 306.1 (M$^+$).

Step C]: (1S,8R)-5-(5-Butoxy-1-methyl-1H-pyrazol-4-yl)-1,11,11-trimethyl-3,4-diaza-tricyclo[6.2.1.0$^{2,7}$]undeca-2,4,6-triene This material was obtained in analogy to example 1 steps C] from (1S,4R)-1,7,7-(1S,4R)-3-[2-(5-chloro-1-methyl-1H-pyrazol-4-yl)-2-oxo-eth-(E)-ylidene]-1,7,7-trimethyl-bicyclo[2.2.1]heptan-2-one (0.52 g) and hydrazine monohydrate (0.424 g), whereas an exchange of chloro v.s. butanol occurred in the NaOMe/butanol treatment step for complete ring closure, to give (1S,8R)-5-(5-Butoxy-1-methyl-1H-pyrazol-4-yl)-1,11,11-trimethyl-3,4-diaza-tricyclo[6.2.1.0$^{2,7}$]undeca-2,4,6-triene (0.068 g) as an light brown oil. MS (EI): 342.2 (M$^+$).

Example 61

3-(1-Phenyl-5-propyl-1H-pyrazol-4-yl)-6,7,8,9-tetrahydro-5H-cyclohepta[c]pyridazine

Step A]: 2-[2-Oxo-2-(1-phenyl-5-propyl-1H-pyrazol-4-yl)-ethyl]-cyclohept-2-enone This material was obtained in analogy to example 1 step B] from [2-oxo-2-(1-phenyl-5-propyl-1H-pyrazol-4-yl)-ethyl]-phosphonic acid dimethyl ester (0.37 g) and cycloheptane-1,2-dione (0.126 g) to give 2-[2-oxo-2-(1-phenyl-5-propyl-1H-pyrazol-4-yl)-ethyl]-cyclohept-2-enone (0.15 g) as a light yellow solid. MS (EI): 336.2 (M$^+$).

Step B]: 3-(1-Phenyl-5-propyl-1H-pyrazol-4-yl)-6,7,8,9-tetrahydro-5H-cyclohepta[c]pyridazine This material was obtained in analogy to example 1 step C], without the NaOMe treatment, from 2-[2-oxo-2-(1-phenyl-5-propyl-1H-pyrazol-4-yl)-ethyl]-cyclohept-2-enone (0.15 g) and hydrazine monohydrate (0.223 g) to give 3-(1-Phenyl-5-propyl-1H-pyrazol-4-yl)-6,7,8,9-tetrahydro-5H-cyclohepta[c]pyridazine (0.059 g) as an off-white crystalline solid. MS (EI): 332.3 (M$^+$).

Example 62

3-[1-(4-Chloro-phenyl)-cyclobutyl]-5,6,7,8,9,10-hexahydro-cycloocta[c]pyridazine

Step A: (Z)-2-{2-[1-(4-Chloro-phenyl)-cyclobutyl]-2-oxo-ethyl}-cyclooct-2-enone

This material was obtained in analogy to example 1 step B] from {2-[1-(4-chloro-phenyl)-cyclobutyl]-2-oxo-ethyl}-phosphonic acid dimethyl ester (0.475 g) and cyclooctane-1,2-dione (0.2 g) to give (Z)-2-{2-[1-(4-chloro-phenyl)-cyclobutyl]-2-oxo-ethyl}-cyclooct-2-enone (0.106 g) as a yellow oil. MS (ESI): 331.4 (MH$^+$).

Step B]: 3-[1-(4-Chloro-phenyl)-cyclobutyl]-5,6,7,8,9,10-hexahydro-cycloocta[c]pyridazine This material was obtained in analogy to example 1 steps C, without NaOMe treatment, from (Z)-2-{2-[1-(4-chloro-phenyl)-cyclobutyl]-2-oxo-ethyl}-cyclooct-2-enone (0.1 g) and hydrazine monohydrate (0.076 g) to give 3-[1-(4-chloro-phenyl)-cyclobutyl]-5,6,7,8,9,10-hexahydro-cycloocta[c]pyridazine (0.04 g) as a light yellow solid. MS (ESI): 327.1 (MH$^+$).

Example 63

3,4-Dicyclopropyl-6-(1-phenyl-5-propyl-1H-pyrazol-4-yl)-pyridazine

Step A: (E or Z)-1,2-Dicyclopropyl-4-(1-phenyl-5-propyl-1H-pyrazol-4-yl)-but-2-ene-1,4-dione This material was obtained in analogy to example 1 step B] from [2-oxo-2-(1-phenyl-5-propyl-1H-pyrazol-4-yl)-ethyl]-phosphonic acid dimethyl ester (0.525 g) and 1,2-dicyclopropyl-ethane-1,2-dione (0.18 g) to give (E or Z)-1,2-dicyclopropyl-4-(1-phenyl-5-propyl-1H-pyrazol-4-yl)-but-2-ene-1,4-dione (0.19 g) as a crystalline light yellow gum. MS (ESI): 349.9 (MH$^+$).

Step B]: 3,4-Dicyclopropyl-6-(1-phenyl-5-propyl-1H-pyrazol-4-yl)-pyridazine

This material was obtained in analogy to example 1 steps C], but without treatment with NaOMe, from (E or Z)-1,2-dicyclopropyl-4-(1-phenyl-5-propyl-1H-pyrazol-4-yl)-but-2-ene-1,4-dione (0.19 g) and hydrazine monohydrate (0.273 g) to give 3,4-dicyclopropyl-6-(1-phenyl-5-propyl-1H-pyrazol-4-yl)-pyridazine (0.084 g) as a crystalline off-white solid. MS (ESI): 345.1 (MH$^+$).

Example 64

3-(4-Fluoro-2-trifluoromethyl-phenyl)-6,7,8,9-tetrahydro-5H-cyclohepta[c]pyridazine Step A]: 2-[2-(4-Fluoro-2-trifluoromethyl-phenyl)-2-oxo-ethyl]-cyclohept-2-enone This material was obtained in analogy to example 1 step B] from [2-(4-fluoro-2-trifluoromethyl-phenyl)-2-oxo-ethyl]-phosphonic acid dimethyl ester (0.747 g) and cycloheptane-1,2-dione (0.8 g) to give (2-[2-(4-fluoro-2-trifluoromethyl-phenyl)-2-oxo-ethyl]-cyclohept-2-enone (0.408 g) as a light brown oil. MS (EI): 314.1 (M$^+$).

Step B]: 3-(4-Fluoro-2-trifluoromethyl-phenyl)-6,7,8,9-tetrahydro-5H-cyclohepta[c]pyridazine This material was obtained in analogy to example 1 step C], without the NaOMe treatment, from 2-[2-(4-fluoro-2-trifluoromethyl-phenyl)-2-oxo-ethyl]-cyclohept-2-enone (0.4 g) and hydrazine monohydrate (0.319 g) to give 3-(4-fluoro-2-trifluoromethyl-phenyl)-6,7,8,9-tetrahydro-5H-cyclohepta[c]pyridazine (0.22 g) as an light yellow solid. MS (EI): 310.1 (M$^+$).

Example 65

3-(1-Methyl-5-trifluoromethyl-1H-pyrazol-4-yl)-6,7,8,9-tetrahydro-5H-cyclohepta[c]pyridazine Step A]: [2-(1-Methyl-5-trifluoromethyl-1H-pyrazol-4-yl)-2-oxo-ethyl]-phosphonic acid dimethyl ester This material was obtained in analogy to example step A] from 1-methyl-5-trifluoromethyl-1H-pyrazole-4-carboxylic acid methyl ester (3.3. g) and methyl-phosphonic acid dimethyl ester (3.934 g) to give [2-(1-methyl-5-trifluoromethyl-1H-pyrazol-4-yl)-2-oxo-ethyl]-phosphonic acid dimethyl ester (4.48 g) as a white solid. MS (ESI): 301.0 (MH$^+$).

Step B]: 2-[2-(1-Methyl-5-trifluoromethyl-1H-pyrazol-4-yl)-2-oxo-ethyl]-cyclohept-2-enone This material was obtained in analogy to example 1 step B] from [2-(1-methyl-5-trifluoromethyl-1H-pyrazol-4-yl)-2-oxo-ethyl]-phosphonic acid dimethyl ester (0.714 g) and cycloheptane-1,2-dione (0.25 g) to give 2-[2-(1-methyl-5-trifluoromethyl-1H-pyrazol-4-yl)-2-oxo-ethyl]-cyclohept-2-enone (0.263 g) as a light yellow foam. MS (EI): 300.1 (M$^+$).

Step C]: 3-(1-Methyl-5-trifluoromethyl-1H-pyrazol-4-yl)-6,7,8,9-tetrahydro-5H-cyclohepta[c]pyridazine This material was obtained in analogy to example 1 step C], without the NaOMe treatment, from 2-[2-(1-methyl-5-trifluoromethyl-1H-pyrazol-4-yl)-2-oxo-ethyl]-cyclohept-2-enone (0.25 g) and hydrazine monohydrate (0.208 g) to give 3-(1-methyl-5-trifluoromethyl-1H-pyrazol-4-yl)-6,7,8,9-tetrahydro-5H-cyclohepta[c]pyridazine (0.06 g) as a light red solid. MS (EI): 296.2 (M$^+$).

Further compounds that were prepared according to example 1, steps A] to C]:

Example 66

3-[1-(4-Fluoro-phenyl)-5-trifluoromethyl-1H-pyrazol-4-yl]-5,6,7,8,9,10-hexahydro-cycloocta[c]pyridazine off-white solid. MS (EI): 390.1 (M$^+$). Prepared from cyclooctane-1,2-dione, {2-[1-(4-Fluoro-phenyl)-5-trifluoromethyl-1H-pyrazol-4-yl]-2-oxo-ethyl}-phosphonic acid dimethyl ester, hydrazine monohydrate.

Example 67

(1SR,8RS)-5-(3-Fluoro-2-trifluoromethyl-phenyl)-3,4-diaza-tricyclo[6.2.1.0$^{2,7}$]undeca-2,4,6-triene light-yellow gum. MS (EI): 308.1 (M$^+$). Prepared from bicyclo[2.2.1]heptane-2,3-dione, [2-(3-Fluoro-2-trifluoromethyl-phenyl)-2-oxo-ethyl]-phosphonic acid dimethyl ester, hydrazine monohydrate.

Example 68

(1SR,8RS)-5-Cyclopropyl-3,4-diaza-tricyclo[6.2.1.0$^{2,7}$]undeca-2,4,6-triene

MS (EI): 186.2 (M$^+$), off-white crystalline solid. Prepared from bicyclo[2.2.1]heptane-2,3-dione, (2-cyclopropyl-2-oxo-ethyl)-phosphonic acid dimethyl ester, hydrazine monohydrate.

Example 69

(1SR,8RS)-5-(5-Fluoro-2-trifluoromethyl-phenyl)-3,4-diaza-tricyclo[6.2.1.0$^{2,7}$]undeca-2,4,6-triene yellow gum. MS (EI): 308.0 (M$^+$). Prepared from bicyclo[2.2.1]heptane-2,3-dione, [2-(5-Fluoro-2-trifluoromethyl-phenyl)-2-oxo-ethyl]-phosphonic acid dimethyl ester, hydrazine monohydrate.

Example 70

(1SR,8RS)-5-(1-Methyl-3-trifluoromethyl-1H-pyrazol-4-yl)-3,4-diaza-tricyclo[6.2.1.0$^{2,7}$]undeca-2,4,6-triene off-white crystalline solid. MS (EI): 294.2 (M$^+$). Prepared from bicyclo[2.2.1]heptane-2,3-dione, [2-(1-Methyl-3-trifluoromethyl-1H-pyrazol-4-yl)-2-oxo-ethyl]-phosphonic acid dimethyl ester, hydrazine monohydrate.

Example 71

(1S,8R)-5-(2-Chloro-4-fluoro-phenyl)-1,11,11-trimethyl-3,4-diaza-tricyclo[6.2.1.0$^{2,7}$]undeca-2,4,6-triene yellow solid. MS (EI): 316.0 (M$^+$). Prepared from (1S,4R)-1,7,7-trimethyl-bicyclo [2.2.1]heptane-2,3-dione, [2-(2-Chloro-4-fluoro-phenyl)-2-oxo-ethyl]-phosphonic acid dimethyl ester, hydrazine monohydrate.

Example 72

3-(3-Fluoro-2-trifluoromethyl-phenyl)-5,6,7,8,9,10-hexahydro-cycloocta[c]pyridazine MS (EI): 324.2 (M$^+$), light-yellow solid. Prepared from cyclooctane-1,2-dione, [2-(3-Fluoro-2-trifluoromethyl-phenyl)-2-oxo-ethyl]-phosphonic acid dimethyl ester, hydrazine monohydrate.

Example 73

3-(5-Fluoro-2-trifluoromethyl-phenyl)-5,6,7,8,9,10-hexahydro-cycloocta[c]pyridazine yellow oil. MS (EI): 324.2 (M$^+$). Prepared from cyclooctane-1,2-dione, [2-(5-Fluoro-2-trifluoromethyl-phenyl)-2-oxo-ethyl]-phosphonic acid dimethyl ester, hydrazine monohydrate.

Example 74

(1S,8R)-5-(2-Chloro-4-fluoro-5-methoxy-phenyl)-1,11,11-trimethyl-3,4-diaza-tricyclo[6.2.1.0$^{2,7}$]undeca-2,4,6-triene yellow solid. MS (EI): 347.1 (M$^+$). Prepared from (1S,4R)-1,7,7-trimethyl-bicyclo[2.2.1]heptane-2,3-dione, [2-(2-Chloro-4-fluoro-5-methoxy-phenyl)-2-oxo-ethyl]-phosphonic acid dimethyl ester, hydrazine monohydrate.

Example 75

(1S,8R)-5-(2-Chloro-4,5-difluoro-phenyl)-1,11,11-trimethyl-3,4-diaza-tricyclo[6.2.1.0$^{2,7}$]undeca-2,4,6-triene yellow oil. MS (EI): 334.1 (M$^+$). Prepared from (1S,4R)-1,7,7-trimethyl-bicyclo[2.2.1]heptane-2,3-dione, [2-(2-Chloro-4,5-difluoro-phenyl)-2-oxo-ethyl]-phosphonic acid dimethyl ester, hydrazine monohydrate.

Example 76

3-Cyclopropyl-5,6,7,8,9,10-hexahydro-cycloocta[c]pyridazine yellow oil. MS (ESI): 292.9 (MH$^+$). Prepared from cyclooctane-1,2-dione, (2-cyclopropyl-2-oxo-ethyl)-phosphonic acid dimethyl ester, hydrazine monohydrate.

Example 77

3-(5-Chloro-2-trifluoromethyl-phenyl)-5,6,7,8,9,10-hexahydro-cycloocta[c]pyridazine yellow oil. MS (ESI): 340.1 (MH$^+$). Prepared from cyclooctane-1,2-dione, [2-(5-Chloro-2-trifluoromethyl-phenyl)-2-oxo-ethyl]-phosphonic acid dimethyl ester, hydrazine monohydrate.

Example 78

(1SR,8RS)-5-(2-Chloro-4-fluoro-phenyl)-3,4-diaza-tricyclo[6.2.1.0$^{2,7}$]undeca-2(7),3,5-triene yellow gum. MS (EI): 274.1 (MH$^+$). Prepared from bicyclo[2.2.1]heptane-2,3-dione, [2-(2-Chloro-4-fluoro-phenyl)-2-oxo-ethyl]-phosphonic acid dimethyl ester, hydrazine monohydrate.

Example 79

(1SR,8RS)-5-(5-Chloro-2-trifluoromethyl-phenyl)-3,4-diaza-tricyclo[6.2.1.0$^{2,7}$]undeca-2(7),3,5-triene yellow gum. MS (EI): 324.1 (M$^+$). Prepared from bicyclo[2.2.1]heptane-2,3-dione, [2-(5-Chloro-2-trifluoromethyl-phenyl)-2-oxo-ethyl]-phosphonic acid dimethyl ester, hydrazine mono hydrate.

Example 80

(1SR,8RS)-5-(2-Chloro-4,5-difluoro-phenyl)-3,4-diaza-tricyclo[6.2.1.0$^{2,7}$]undeca-2(7),3,5-triene yellow solid. MS (EI): 292.1 (M$^+$). Prepared from bicyclo[2.2.1]heptane-2,3-dione, [2-(2-Chloro-4,5-difluoro-phenyl)-2-oxo-ethyl]-phosphonic acid dimethyl ester, hydrazine monohydrate.

Example 81

3-(1-Phenyl-5-trifluoromethyl-1H-pyrazol-4-yl)-5,6,7,8,9,10-hexahydro-cycloocta[c]pyridazine light yellow solid. MS (EI): 372.3 (M$^+$). Prepared from cyclooctane-1,2-dione, [2-oxo-2-(1-phenyl-5-trifluoromethyl-1H-pyrazol-4-yl)-ethyl]-phosphonic acid dimethyl ester, hydrazine monohydrate.

Example 82

(1S,8R)-1,11,11-Trimethyl-5-(4-methyl-2-phenyl-thiazol-5-yl)-3,4-diaza-tricyclo[6.2.1.0$^{2,7}$]undeca-2,4,6-triene orange solid. MS (EI): 361.0 (M$^+$). Prepared from (1S,4R)-1,7,7-trimethyl-bicyclo[2.2.1]heptane-2,3-dione, [2-(4-Methyl-2-phenyl-thiazol-5-yl)-2-oxo-ethyl]-phosphonic acid dimethyl ester, hydrazine monohydrate.

Example 83

3-(4-Methyl-2-phenyl-thiazol-5-yl)-5,6,7,8,9,10-hexahydro-cycloocta[c]pyridazine light brown solid. MS (ESI): 335.1 (M$^+$). Prepared from cyclooctane-1,2-dione, [2-(4-Methyl-2-phenyl-thiazol-5-yl)-2-oxo-ethyl]-phosphonic acid dimethyl ester, hydrazine monohydrate.

Example 84

(1SR,8RS)-5-(2-Methoxy-phenyl)-3,4-diaza-tricyclo[6.2.1.0$^{2,7}$]undeca-2,4,6-triene light yellow gum. MS (ESI): 253.3 (MH$^+$). Prepared from bicyclo[2.2.1]heptane-2,3-dione, [2-(2-Methoxy-phenyl)-2-oxo-ethyl]-phosphonic acid dimethyl ester, hydrazine monohydrate.

Example 85

(1SR,8RS)-5-o-Tolyl-3,4-diaza-tricyclo[6.2.1.0$^{2,7}$]undeca-2,4,6-triene light yellow gum. MS (EI): 236.3 (M$^+$). Prepared from bicyclo[2.2.1]heptane-2,3-dione, (2-Oxo-2-o-tolyl-ethyl)-phosphonic acid dimethyl ester, hydrazine monohydrate.

Example 86

(1S,8R)-5-(2-Methoxy-phenyl)-1,11,11-trimethyl-3,4-diaza-tricyclo[6.2.1.0$^{2,7}$]undeca-2,4,6-triene yellow solid. MS (EI): 294.3 (M$^+$). Prepared from (1S,4R)-1,7,7-trimethyl-bicyclo[2.2.1]heptane-2,3-dione, [2-(2-Methoxy-phenyl)-2-oxo-ethyl]-phosphonic acid dimethyl ester, hydrazine monohydrate

Example 87

(1S,8R)-1,11,11-Trimethyl-5-o-tolyl-3,4-diaza-tricyclo[6.2.1.0$^{2,7}$]undeca-2,4,6-triene yellow gum. MS (ESI): 278.2 (MH$^+$). Prepared from (1S,4R)-1,7,7-trimethyl-bicyclo[2.2.1]heptane-2,3-dione, (2-Oxo-2-o-tolyl-ethyl)-phosphonic acid dimethyl ester, hydrazine monohydrate.

Example 88

3-(2-Methoxy-phenyl)-5,6,7,8,9,10-hexahydro-cycloocta[c]pyridazine yellow oil. MS (EI): 268.2 (M$^+$). Prepared from cyclooctane-1,2-dione, [2-(2-Methoxy-phenyl)-2-oxo-ethyl]-phosphonic acid dimethyl ester, hydrazine monohydrate.

Example 89

3-(2-Methoxy-phenyl)-6,7,8,9-tetrahydro-5H-cyclohepta[c]pyridazine light yellow gum. MS (ESI): 255.2 (MH$^+$). Prepared from cycloheptane-1,2-dione, [2-(2-Methoxy-phenyl)-2-oxo-ethyl]-phosphonic acid dimethyl ester, hydrazine monohydrate.

Example 90

3-o-Tolyl-6,7,8,9-tetrahydro-5H-cyclohepta[c]pyridazine light yellow solid. MS (EI): 238.2 (M$^+$). Prepared from cycloheptane-1,2-dione, (2-Oxo-2-o-tolyl-ethyl)-phosphonic acid dimethyl ester, hydrazine monohydrate.

Example 91

3-(4-Chloro-2-methyl-phenyl)-5,6,7,8,9,10-hexahydro-cycloocta[c]pyridazine light yellow solid. MS (EI): 286.1 (M$^+$). Prepared from cyclooctane-1,2-dione, [2-(4-Chloro-2-methyl-phenyl)-2-oxo-ethyl]-phosphonic acid dimethyl ester, hydrazine monohydrate.

Example 92

3-(4-Chloro-2-methyl-phenyl)-6,7,8,9-tetrahydro-5H-cyclohepta[c]pyridazine light brown solid. MS (EI): 272.2 (M$^+$). Prepared from cycloheptane-1,2-dione, [2-(4-Chloro-2-methyl-phenyl)-2-oxo-ethyl]-phosphonic acid dimethyl ester, hydrazine monohydrate.

Example 93

(1S,8R)-5-(4-Chloro-2-methyl-phenyl)-3,4-diaza-tricyclo[6.2.1.0$^{2,7}$]undeca-2(7),3,5-triene MS (EI): 270.2 (M$^+$), yellow waxy solid. Prepared from bicyclo[2.2.1]heptane-2,3-dione, [2-(4-Chloro-2-methyl-phenyl)-2-oxo-ethyl]-phosphonic acid dimethyl ester, hydrazine monohydrate.

Example 94

(1S,8R)-1,11,11-Trimethyl-5-(1-methyl-1H-pyrrol-2-yl)-3,4-diaza-tricyclo[6.2.1.0$^{2,7}$]undeca-2,4,6-triene light brown amorphous solid. MS (EI): 267.2 (M$^+$). Prepared from (1S,4R)-1,7,7-trimethyl-bicyclo[2.2.1]heptane-2,3-dione, [2-(1-Methyl-1H-pyrrol-2-yl)-2-oxo-ethyl]-phosphonic acid dimethyl ester, hydrazine monohydrate.

Example 95

3-(1-Methyl-1H-pyrrol-2-yl)-5,6,7,8,9,10-hexahydro-cycloocta[c]pyridazine off-white solid. MS (ESI): 241.2 (M$^+$). Prepared from cyclooctane-1,2-dione, [2-(1-Methyl-1H-pyrrol-2-yl)-2-oxo-ethyl]-phosphonic acid dimethyl ester, hydrazine monohydrate.

Example 96

3-(1-Methyl-1H-pyrrol-2-yl)-6,7,8,9-tetrahydro-5H-cyclohepta[c]pyridazine light brown solid. MS (EI): 227.2 (M$^+$). Prepared from cycloheptane-1,2-dione, [2-(1-Methyl-1H-pyrrol-2-yl)-2-oxo-ethyl]-phosphonic acid dimethyl ester, hydrazine monohydrate.

Example 97

(1SR,8RS)-5-(1-Methyl-1H-pyrrol-2-yl)-3,4-diaza-tricyclo[6.2.1.0$^{2,7}$]undeca-2,4,6-triene off-white solid. MS (EI): 225.29 (M$^+$). Prepared from bicyclo[2.2.1]heptane-2,3-dione, [2-(1-Methyl-1H-pyrrol-2-yl)-2-oxo-ethyl]-phosphonic acid dimethyl ester, hydrazine monohydrate.

Example 98

(1S,8R)-5-(4-Chloro-2-methyl-phenyl)-1,11,11-trimethyl-3,4-diaza-tricyclo[6.2.1.0$^{2,7}$]undeca-2(7),3,5-triene yellow solid. MS (EI): 312.2 (M$^+$). Prepared from (1S,4R)-1,7,7-trimethyl-bicyclo [2.2.1]heptane-2,3-dione, [2-(4-Chloro-2-methyl-phenyl)-2-oxo-ethyl]-phosphonic acid dimethyl ester, hydrazine monohydrate.

Example 99

3-(1-Methyl-cyclopropyl)-5,6,7,8,9,10-hexahydro-cycloocta[c]pyridazine light yellow oil. MS (EI): 216.3 (M$^+$). Prepared from cyclooctane-1,2-dione, [2-(1-Methyl-cyclopropyl)-2-oxo-ethyl]-phosphonic acid dimethyl ester, hydrazine monohydrate.

Example 100

(1SR,8RS)-5-(4-Fluoro-2-methyl-phenyl)-3,4-diaza-tricyclo[6.2.1.0$^{2,7}$]undeca-2(7),3,5-triene yellow oil. MS (EI): 254.2 (M$^+$). Prepared from bicyclo [2.2.1]heptane-2,3-dione, [2-(4-Fluoro-2-methyl-phenyl)-2-oxo-ethyl]-phosphonic acid dimethyl ester, hydrazine monohydrate.

Example 101

6,6-Dimethyl-3-(5-methyl-1-phenyl-1H-pyrazol-4-yl)-6,7-dihydro-5H-cyclopenta[c]pyridazine light yellow crystalline solid. MS (ESI): 305.2 (MH$^+$). Prepared from 4,4-dimethyl-cyclopentane-1,2-dione (synthesis described in: J. Chem. Soc., 121, 1922, p523), [2-(5-Methyl-1-phenyl-1H-pyrazol-4-yl)-2-oxo-ethyl]-phosphonic acid dimethyl ester, hydrazine monohydrate.

Example 102

(1S,8R)-5-(5-Fluoro-2-methoxy-phenyl)-1,11,11-trimethyl-3,4-diaza-tricyclo[6.2.1.0$^{2,7}$]undeca-2,4,6-triene light yellow solid. MS (ESI): 312.9 (MH$^+$). Prepared from (1S,4R)-1,7,7-trimethyl-bicyclo[2.2.1]heptane-2,3-dione, [2-(5-Fluoro-2-methoxy-phenyl)-2-oxo-ethyl]-phosphonic acid dimethyl ester, hydrazine monohydrate.

Example 103

(1SR,8RS)-5-(5-Fluoro-2-methoxy-phenyl)-3,4-diaza-tricyclo[6.2.1.0$^{2,7}$]undeca-2,4,6-triene yellow solid. MS (ESI): 271.1 (MH$^+$). Prepared from bicyclo[2.2.1]heptane-2,3-dione, [2-(5-Fluoro-2-methoxy-phenyl)-2-oxo-ethyl]-phosphonic acid dimethyl ester, hydrazine monohydrate.

Example 104

6,6-Dimethyl-3-(2-trifluoromethyl-phenyl)-6,7-dihydro-5H-cyclopenta[c]pyridazine yellow oil. MS (EI): 292.2 (M$^+$). Prepared from 4,4-dimethyl-cyclopentane-1,2-dione, 2-oxo-2-(2-trifluoromethyl-phenyl)-ethyl]-phosphonic acid dimethyl ester, hydrazine monohydrate.

Example 105

(1S,8R)-5-(4-Fluoro-2-methyl-phenyl)-1,11,11-trimethyl-3,4-diaza-tricyclo[6.2.1.0$^{2,7}$]undeca-2(7),3,5-triene yellow solid. MS (ESI): 297.3 (MH$^+$). Prepared from (1S,4R)-1,7,7-trimethyl-bicyclo [2.2.1]heptane-2,3-dione, [2-(4-Fluoro-2-methyl-phenyl)-2-oxo-ethyl]-phosphonic acid dimethyl ester, hydrazine monohydrate.

Example 106

3-(2-Chloro-phenyl)-6,6-dimethyl-6,7-dihydro-5H-cyclopenta[c]pyridazine yellow viscous oil. MS (EI): 258.2 (M$^+$). Prepared from 4,4-dimethyl-cyclopentane-1,2-dione, [2-(2-Chloro-phenyl)-2-oxo-ethyl]-phosphonic acid dimethyl ester, hydrazine monohydrate.

Example 107

3-(2,4-Difluoro-phenyl)-6,6-dimethyl-6,7-dihydro-5H-cyclopenta[c]pyridazine yellow solid. MS (EI): 260.1 (M$^+$). Prepared from 4,4-dimethyl-cyclopentane-1,2-dione, [[2-(2,4-difluoro-phenyl)-2-oxo-ethyl]-phosphonic acid dimethyl ester, hydrazine monohydrate.

Example 108

(1SR,8RS)-5-(1-tert-Butyl-5-trifluoromethyl-1H-pyrazol-4-yl)-3,4-diaza-tricyclo[6.2.1.0$^{2,7}$]undeca-2,4,6-triene light yellow crystalline solid. MS (ESI): 336.9 (MH$^+$). Prepared from bicyclo[2.2.1]heptane-2,3-dione, [2-(1-tert-Butyl-5-trifluoromethyl-1H-pyrazol-4-yl)-2-oxo-ethyl]-phosphonic acid dimethyl ester, hydrazine monohydrate.

Example 109

(1S,8R)-5-(1-tert-Butyl-5-trifluoromethyl-1H-pyrazol-4-yl)-1,11,11-trimethyl-3,4-diaza-tricyclo[6.2.1.0$^{2,7}$]undeca-2,4,6-triene yellow solid. MS (ESI): 379.2 (MH$^+$). Prepared from 1,7,7-trimethyl-bicyclo[2.2.1]heptane-2,3-dione, [2-(1-tert-Butyl-5-trifluoromethyl-1H-pyrazol-4-yl)-2-oxo-ethyl]-phosphonic acid dimethyl ester, hydrazine monohydrate.

Example 110

(1SR,8RS)-5-(2-Trifluoromethoxy-phenyl)-3,4-diaza-tricyclo[6.2.1.0$^{2,7}$]undeca-2,4,6-triene yellow gum. MS (EI): 306.2 (M$^+$). Prepared from bicyclo[2.2.1]heptane-2,3-dione, [2-Oxo-2-(2-trifluoromethoxy-phenyl)-ethyl]-phosphonic acid dimethyl ester, hydrazine monohydrate.

Example 111

3 (1S,8R)-1,11,11-Trimethyl-5-(1-methyl-cyclopropyl)-3,4-diaza-tricyclo[6.2.1.0$^{2,7}$]undeca-2,4,6-triene light yellow oil. MS (ESI): 243.2 (MH$^+$). Prepared from (1S,4R)-1,7,7-trimethyl-bicyclo [2.2.1]heptane-2,3-dione, [2-(1-Methyl-cyclopropyl)-2-oxo-ethyl]-phosphonic acid dimethyl ester, hydrazine monohydrate.

Example 112

(1S,8R)-1,11,11-Trimethyl-5-(2-trifluoromethoxy-phenyl)-3,4-diaza-tricyclo[6.2.1.0$^{2,7}$]undeca-2,4,6-triene light yellow solid. MS (EI): 348.0 (M$^+$). Prepared from (1S,4R)-1,7,7-trimethyl-bicyclo[2.2.1]heptane-2,3-dione, [2-Oxo-2-(2-trifluoromethoxy-phenyl)-ethyl]-phosphonic acid dimethyl ester, hydrazine monohydrate.

Example 113

(1S,8R)-5-(1-tert-Butyl-5-methyl-1H-pyrazol-4-yl)-1,11,11-trimethyl-3,4-diaza-tricyclo[6.2.1.0$^{2,7}$]undeca-2,4,6-triene yellow crystalline solid. MS (ESI): 325.2 (MH$^+$). Prepared from (1S,4R)-1,7,7-trimethyl-bicyclo [2.2.1]heptane-2,3-dione, [2-(1-tert-Butyl-5-methyl-1H-pyrazol-4-yl)-2-oxo-ethyl]-phosphonic acid dimethyl ester, hydrazine monohydrate.

Example 114

(1SR,8RS)-5-(1-tert-Butyl-5-methyl-1H-pyrazol-4-yl)-3,4-diaza-tricyclo[6.2.1.0$^{2,7}$]undeca-2,4,6-triene light yellow crystalline solid. MS (ESI): 283.2 (MH$^+$). Prepared from bicyclo[2.2.1]heptane-2,3-dione, [2-(1-tert-Butyl-5-methyl-1H-pyrazol-4-yl)-2-oxo-ethyl]-phosphonic acid dimethyl ester, hydrazine monohydrate.

Example 115

6,6-Dimethyl-3-(2-trifluoromethoxy-phenyl)-6,7-dihydro-5H-cyclopenta[c]pyridazine light yellow oil. MS (ESI): 309.0 (MH$^+$). Prepared from 4,4-dimethyl-cyclopentane-1,2-dione, [2-Oxo-2-(2-trifluoromethoxy-phenyl)-ethyl]-phosphonic acid dimethyl ester, hydrazine monohydrate.

Example 116

3-(1-tert-Butyl-5-trifluoromethyl-1H-pyrazol-4-yl)-6,6-dimethyl-6,7-dihydro-5H-cyclopenta[c]pyridazine light yellow crystalline solid. MS (ESI): 339.0 (MH$^+$). Prepared from 4,4-dimethyl-cyclopentane-1,2-dione, [2-(1-tert-Butyl-5-trifluoromethyl-1H-pyrazol-4-yl)-2-oxo-ethyl]-phosphonic acid dimethyl ester, hydrazine monohydrate.

Example 117

(1SR,8RS)-5-(1-tert-Butyl-5-cyclopropyl-1H-pyrazol-4-yl)-3,4-diaza-tricyclo[6.2.1.0$^{2,7}$]undeca-2,4,6-triene off-white solid. MS (ESI): 309.1 (MH$^+$). Prepared from bicyclo[2.2.1]heptane-2,3-dione, [2-(1-tert-Butyl-5-cyclopropyl-1H-pyrazol-4-yl)-2-oxo-ethyl]-phosphonic acid dimethyl ester, hydrazine monohydrate.

Example 118

(1S,8R)-5-(1-tert-Butyl-5-cyclopropyl-1H-pyrazol-4-yl)-1,11,11-trimethyl-3,4-diaza-tricyclo[6.2.1.0$^{2,7}$]undeca-2,4,6-triene yellow solid. MS (ESI): 351.2 (MH$^+$). Prepared from (1S,4R)-1,7,7-trimethyl-bicyclo[2.2.1]heptane-2,3-dione, [2-(1-tert-Butyl-5-cyclopropyl-1H-pyrazol-4-yl)-2-oxo-ethyl]-phosphonic acid dimethyl ester, hydrazine monohydrate.

Example 119

3-(5-Chloro-2-trifluoromethyl-phenyl)-6,6-dimethyl-6,7-dihydro-5H-cyclopenta[c]pyridazine yellow solid. MS (EI): 326.2 (M$^+$). Prepared from 4,4-dimethyl-cyclopentane-1,2-dione, [2-(5-Chloro-2-trifluoromethyl-phenyl)-2-oxo-ethyl]-phosphonic acid dimethyl ester, hydrazine monohydrate.

Example 120

(1S,8R)-5-(5-Cyclopropyl-1-methyl-1H-pyrazol-4-yl)-1,11,11-trimethyl-3,4-diaza-tricyclo[6.2.1.0$^{2,7}$]undeca-2,4,6-triene yellow foam. MS (ESI): 309.1 (MH$^+$). Prepared from (1S,4R)-1,7,7-trimethyl-bicyclo[2.2.1]heptane-2,3-dione, [2-(5-Cyclopropyl-1-methyl-1H-pyrazol-4-yl)-2-oxo-ethyl]-phosphonic acid dimethyl ester, hydrazine monohydrate.

Example 121

(1SR,8RS)-5-(5-Cyclopropyl-1-methyl-1H-pyrazol-4-yl)-3,4-diaza-tricyclo[6.2.1.0$^{2,7}$]undeca-2,4,6-triene yellow foam. MS (ESI): 267.1 (MH$^+$). Prepared from bicyclo[2.2.1]heptane-2,3-dione, [2-(5-Cyclopropyl-1-methyl-1H-pyrazol-4-yl)-2-oxo-ethyl]-phosphonic acid dimethyl ester, hydrazine monohydrate.

Example 122

3-(5-Cyclopropyl-1-methyl-1H-pyrazol-4-yl)-6,6-dimethyl-6,7-dihydro-5H-cyclopenta[c]pyridazine yellow gum. MS (ESI): 269.2 (MH$^+$). Prepared from 4,4-dimethyl-cyclopentane-1,2-dione, [2-(5-Cyclopropyl-1-methyl-1H-pyrazol-4-yl)-2-oxo-ethyl]-phosphonic acid dimethyl ester, hydrazine monohydrate.

Example 123

(1S,8R)-5-Cyclobutyl-1,11,11-trimethyl-3,4-diaza-tricyclo[6.2.1.0$^{2,7}$]undeca-2,4,6-triene light yellow solid. MS (EI): 242.2 (M$^+$). Prepared from (1S,4R)-1,7,7-trimethyl-bicyclo[2.2.1]heptane-2,3-dione, (2-Cyclobutyl-2-oxo-ethyl)-phosphonic acid dimethyl ester, hydrazine monohydrate.

Example 124

(1SR,8RS)-5-Cyclobutyl-3,4-diaza-tricyclo[6.2.1.0$^{2,7}$]undeca-2,4,6-triene light yellow solid. MS (ESI): 200.2 (M$^+$). Prepared from bicyclo[2.2.1]heptane-2,3-dione, (2-Cyclobutyl-2-oxo-ethyl)-phosphonic acid dimethyl ester, hydrazine monohydrate.

Example 125

3-(1-tert-Butyl-5-methyl-1H-pyrazol-4-yl)-6,6-dimethyl-6,7-dihydro-5H-cyclopenta[c]pyridazine yellow crystalline solid. MS (ESI): 285.1 (MH$^+$). Prepared from 4,4-dimethyl-cyclopentane-1,2-dione, [2-(1-tert-Butyl-5-methyl-1H-pyrazol-4-yl)-2-oxo-ethyl]-phosphonic acid dimethyl ester, hydrazine monohydrate.

Example 126

(1S,8R)-5-(1,3-Dimethyl-1H-pyrazol-4-yl)-1,11,11-trimethyl-3,4-diaza-tricyclo[6.2.1.0$^{2,7}$]undeca-2,4,6-triene yellow solid. MS (EI): 282.3 (M$^+$). Prepared from (1S,4R)-1,7,7-trimethyl-bicyclo[2.2.1]heptane-2,3-dione, [2-(1,3-Dimethyl-1H-pyrazol-4-yl)-2-oxo-ethyl]-phosphonic acid dimethyl ester, hydrazine monohydrate.

Example 127

(1S,8R)-1,11,11-Trimethyl-5-(1-methyl-5-trifluoromethyl-1H-pyrazol-4-yl)-3,4-diaza-tricyclo[6.2.1.0$^{2,7}$]undeca-2,4,6-triene yellow oil. MS (ESI): 337.0 (MH$^+$). Prepared from (1S,4R)-1,7,7-trimethyl-bicyclo[2.2.1]heptane-2,3-dione, [2-(1-Methyl-5-trifluoromethyl-1H-pyrazol-4-yl)-2-oxo-ethyl]-phosphonic acid dimethyl ester, hydrazine monohydrate.

Example 128

(1S,8R)-5-(1-Benzyl-5-trifluoromethyl-1H-pyrazol-4-yl)-1,11,11-trimethyl-3,4-diaza-tricyclo[6.2.1.0$^{2,7}$]undeca-2,4,6-triene yellow oil. MS (EI): 413.2 (M$^+$). Prepared from (1S,4R)-1,7,7-trimethyl-bicyclo[2.2.1]heptane-2,3-dione, [2-(1-Benzyl-5-trifluoromethyl-1H-pyrazol-4-yl)-2-oxo-ethyl]-phosphonic acid dimethyl ester, hydrazine monohydrate.

Example 129

(1S,8R)-5-(1-Benzyl-5-methyl-1H-pyrazol-4-yl)-1,11,11-trimethyl-3,4-diaza-tricyclo[6.2.1.0$^{2,7}$]undeca-2,4,6-triene light brown amorphous solid. MS (ESI): 359.1 (MH$^+$). Prepared from (1S,4R)-1,7,7-trimethyl-bicyclo[2.2.1]heptane-2,3-dione, [2-(1-Benzyl-5-methyl-1H-pyrazol-4-yl)-2-oxo-ethyl]-phosphonic acid dimethyl ester, hydrazine monohydrate.

Example 130

(1S,8R)-5-(1-Benzyl-3-methyl-1H-pyrazol-4-yl)-1,11,11-trimethyl-3,4-diaza-tricyclo[6.2.1.0$^{2,7}$]undeca-2,4,6-triene yellow solid. MS (ESI): 359.1 (MH$^+$). Prepared from (1S,4R)-1,7,7-trimethyl-bicyclo[2.2.1]heptane-2,3-dione, [2-(1-Benzyl-3-methyl-1H-pyrazol-4-yl)-2-oxo-ethyl]-phosphonic acid dimethyl ester, hydrazine monohydrate.

Example 131

(1SR,8RS)-5-Cyclopropyl-6-methyl-3,4-diaza-tricyclo[6.2.1.0$^{2,7}$]undeca-2,4,6-triene off-white crystalline solid. MS (EI): 200.2 (M$^+$). Prepared from bicyclo[2.2.1]heptane-2,3-dione, (2-Cyclopropyl-1-methyl-2-oxo-ethyl)-phosphonic acid diethyl ester, hydrazine monohydrate.

Example 132

(1S,8R)-5-Cyclopropyl-1,6,11,11-tetramethyl-3,4-diaza-tricyclo[6.2.1.0$^{2,7}$]undeca-2,4,6-triene light yellow solid. MS (EI): 242.2 (M$^+$). Prepared from (1S,4R)-1,7,7-trimethyl-bicyclo [2.2.1]heptane-2,3-dione, (2-Cyclopropyl-1-methyl-2-oxo-ethyl)-phosphonic acid diethyl ester, hydrazine monohydrate.

Example 133

(1S,8R)-5-(1-tert-Butyl-5-phenyl-1H-pyrazol-4-yl)-1,11,11-trimethyl-3,4-diaza-tricyclo[6.2.1.0$^{2,7}$]undeca-2,4,6-triene light yellow solid. MS (EI): 386.3 (M$^+$). Prepared from (1S,4R)-1,7,7-trimethyl-bicyclo [2.2.1]heptane-2,3-dione, [2-(1-tert-Butyl-5-phenyl-1H-pyrazol-4-yl)-2-oxo-ethyl]-phosphonic acid dimethyl ester, hydrazine monohydrate.

Example 134

(1S,8R)-5-(4-Chloro-benzyl)-1,11,11-trimethyl-3,4-diaza-tricyclo[6.2.1.0$^{2,7}$]undeca-2,4,6-triene light yellow oil. MS (EI): 313.2 (M$^+$). Prepared from (1S,4R)-1,7,7-trimethyl-bicyclo[2.2.1]heptane-2,3-dione, [3-(4-Chloro-phenyl)-2-oxo-propyl]-phosphonic acid dimethyl ester, hydrazine monohydrate.

Example 135

(1S,8R)-1,11,11-Trimethyl-5-(1-trifluoromethyl-cyclopropyl)-3,4-diaza-tricyclo[6.2.1.0$^{2,7}$]undeca-2,4,6-triene yellow solid. MS (ESI): 297.1 (MH$^+$). Prepared from (1S,4R)-1,7,7-trimethyl-bicyclo[2.2.1]heptane-2,3-dione, [[2-Oxo-2-(1-trifluoromethyl-cyclopropyl)-ethyl]-phosphonic acid dimethyl ester, hydrazine monohydrate.

Example 136

3-(4-Fluoro-2-trifluoromethyl-phenyl)-6,6-dimethyl-6,7-dihydro-5H-cyclopenta[c]pyridazine light yellow oil. MS (ESI): 311.0 (MH$^+$). Prepared from 4,4-dimethyl-cyclopentane-1,2-dione, [2-(4-Fluoro-2-trifluoromethyl-phenyl)-2-oxo-ethyl]-phosphonic acid dimethyl ester, hydrazine monohydrate.

Example 137

(1R,8S)-5-Cyclopropyl-1,11,11-trimethyl-3,4-diaza-tricyclo[6.2.1.0$^{2,7}$]undeca-2(7),3,5-triene colorless oil. MS (EI): 228.3 (M$^+$). Prepared from (1R,4S)-1,7,7-trimethyl-bicyclo[2.2.1]heptane-2,3-dione, (2-Cyclopropyl-2-oxo-ethyl)-phosphonic acid dimethyl ester, hydrazine monohydrate.

Example 138

3-(3-Fluoro-2-trifluoromethyl-phenyl)-6,6-dimethyl-6,7-dihydro-5H-cyclopenta[c]pyridazine light yellow solid. MS (EI): 310.2 (M$^+$). Prepared from 4,4-dimethyl-cyclopentane-1,2-dione, [2-(3-Fluoro-2-trifluoromethyl-phenyl)-2-oxo-ethyl]-phosphonic acid dimethyl ester, hydrazine monohydrate.

Example 139

(1SR,8RS)-5-(2,5-Dichloro-phenyl)-3,4-diaza-tricyclo[6.2.1.0$^{2,7}$]undeca-2(7),3,5-triene yellow crystalline solid. MS (ESI): 291.0 (MH$^+$). Prepared from bicyclo[2.2.1]heptane-2,3-dione, [2-(2,5-Dichloro-phenyl)-2-oxo-ethyl]-phosphonic acid dimethyl ester, hydrazine monohydrate.

Example 140

(1SR,8RS)-5-(2,3-Dimethyl-phenyl)-3,4-diaza-tricyclo[6.2.1.0$^{2,7}$]undeca-2(7),3,5-triene light yellow crystalline solid. MS (ESI): 251.0 (MH$^+$). Prepared from bicyclo[2.2.1]heptane-2,3-dione, [2-(2,5-Dimethyl-phenyl)-2-oxo-ethyl]-phosphonic acid dimethyl ester, hydrazine monohydrate.

Example 141

3-(2,5-Dichloro-phenyl)-6,6-dimethyl-6,7-dihydro-5H-cyclopenta[c]pyridazine light yellow crystalline solid. MS (EI): 294.2 (MH$^+$). Prepared from 4,4-dimethyl-cyclopentane-1,2-dione, [2-(2,5-Dichloro-phenyl)-2-oxo-ethyl]-phosphonic acid dimethyl ester, hydrazine monohydrate.

Example 142

3-(2,3-Dimethyl-phenyl)-6,6-dimethyl-6,7-dihydro-5H-cyclopenta[c]pyridazine light yellow crystalline solid. MS (EI): 252.3 (M$^+$). Prepared from 4,4-dimethyl-cyclopentane-1,2-dione, [2-(2,5-Dimethyl-phenyl)-2-oxo-ethyl]-phosphonic acid dimethyl ester, hydrazine monohydrate.

Example 143

(1SR,8RS)-5-(2,4-Dichloro-phenyl)-3,4-diaza-tricyclo[6.2.1.0$^{2,7}$]undeca-2(7),3,5-triene light yellow crystalline solid. MS (ESI): 291.0 (MH$^+$). Prepared from bicyclo[2.2.1]heptane-2,3-dione, [2-(2,4-Dichloro-phenyl)-2-oxo-ethyl]-phosphonic acid dimethyl ester, hydrazine monohydrate.

Example 144

(1SR,8RS)-5-(2,3-Dichloro-phenyl)-3,4-diaza-tricyclo[6.2.1.0$^{2,7}$]undeca-2(7),3,5-triene yellow viscous oil. MS (ESI): 291.0 (MH$^+$). Prepared from bicyclo[2.2.1]heptane-2,3-dione, [2-(2,3-Dichloro-phenyl)-2-oxo-ethyl]-phosphonic acid dimethyl ester, hydrazine monohydrate.

Example 145

(1SR,8RS)-5-(2,4-Dimethyl-phenyl)-3,4-diaza-tricyclo[6.2.1.0$^{2,7}$]undeca-2(7),3,5-triene off-white solid. MS (ESI): 251.0 (MH$^+$). Prepared from bicyclo[2.2.1]heptane-2,3-dione, [2-(2,4-Dimethyl-phenyl)-2-oxo-ethyl]-phosphonic acid dimethyl ester, hydrazine monohydrate.

Example 146

(1R,8S)-5-Cyclopropyl-8,11,11-trimethyl-3,4-diaza-tricyclo[6.2.1.0$^{2,7}$]undeca-2(7),3,5-triene yellow oil. MS (ESI): 229.0 (MH$^+$). This compound was obtained as minor component at the preparation of example 34, as corresponding regioisomer of example 34, isolated and purified by silica gel chromatography.

Example 147

(1S,8R)-5-Cyclopropyl-8,11,11-trimethyl-3,4-diaza-tricyclo[6.2.1.0$^{2,7}$]undeca-2(7),3,5-triene yellow oil. MS (ESI): 229.1 (MH$^+$). This compound was obtained as minor component at the preparation of example 137, as corresponding regioisomer of example 137, isolated and purified by silica gel chromatography.

Example 148

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 149

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

It is to be understood that the invention is not limited to the particular embodiments of the invention described above, as variations of the particular embodiments may be made and still fall within the scope of the appended claims.

The invention claimed is:

1. A compound of the formula:

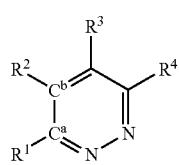

(I)

wherein

R$^1$ and R$^2$ together with the carbon atoms C$^a$ and C$^b$ to which they are attached form

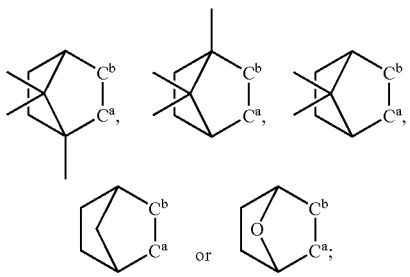

R$^3$ is hydrogen, alkyl, cycloalkyl or trifluoromethyl;

R$^4$ is benzyl, cycloalkyl, arylcycloalkyl, adamantyl, aryl or heterocyclyl, wherein benzyl, cycloalkyl, arylcycloalkyl, aryl and heterocyclyl are optionally substituted with one to three substituents independently selected from alkyl, cycloalkyl, alkoxy, hydroxy, halogen, trifluormethyl, trifluoromethoxy, benzyl, phenyl and phenyl substituted with one to three substituents independently selected from alkyl, alkoxy, hydroxy, cycloalkyl, halogen and trifluoromethyl;

or pharmaceutically acceptable salts and esters thereof.

2. The compound according to claim 1, wherein R$^4$ is cycloalkyl, arylcycloalkyl, adamantyl, aryl or heterocyclyl, wherein arylcycloalkyl, aryl and heterocyclyl are optionally substituted with one to three substituents independently selected from alkyl, alkoxy, hydroxy, halogen, trifluormethyl, phenyl and phenyl substituted with one to three substituents independently selected from alkyl, alkoxy, hydroxy, cycloalkyl, halogen and trifluoromethyl.

3. The compound according to claim 1, wherein R$^3$ is hydrogen.

4. The compound according to claim 1, wherein R$^3$ is methyl.

5. The compound according to claim 1, wherein R$^4$ is benzyl, cycloalkyl, phenylcycloalkyl, adamantyl, phenyl, indolyl, pyrazolyl, pyrrolyl or thiazolyl, wherein benzyl, cycloalkyl, phenylcycloalkyl, phenyl, indolyl, pyrazolyl, pyrrolyl and thiazolyl are optionally substituted with one to three substituents independently selected from alkyl, cycloalkyl, alkoxy, hydroxy, halogen, trifluormethyl, trifluoromethoxy, benzyl, phenyl and phenyl substituted with one to three substituents independently selected from alkyl, halogen and trifluoromethyl.

6. The compound according to claim 1, wherein R$^4$ is benzyl, cyclopropyl, methyl-cyclopropyl, cyclobutyl, phenylcyclopropyl, phenylcyclobutyl, adamantyl, phenyl, indolyl, pyrazolyl, pyrrolyl or thiazolyl, wherein benzyl, cyclopropyl, phenylcyclopropyl, phenylcyclobutyl, phenyl, indolyl, pyrazolyl, pyrrolyl and thiazolyl are optionally substituted with one to three substituents independently selected from alkyl, cycloalkyl, alkoxy, halogen, trifluormethyl, trifluoromethoxy, benzyl, phenyl and phenyl substituted with one to three substituents independently selected from alkyl, halogen and trifluoromethyl.

7. The compound according to claim 1, wherein R$^1$ and R$^2$ together with the carbon atoms C$^a$ and C$^b$ to which they are attached form

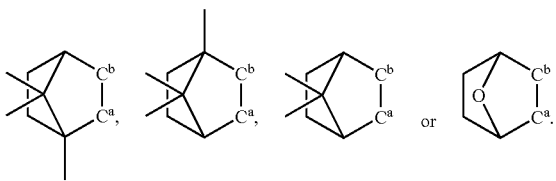

8. The compound according to claim 1, wherein $R^1$ and $R^2$ together with the carbon atoms $C^a$ and $C^b$ to which they are attached form

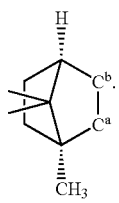

9. The compound according to claim 1, wherein $R^1$ and $R^2$ together with the carbon atoms $C^a$ and $C^b$ to which they are attached form

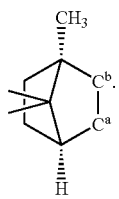

10. The compound according to claim 1 selected from:
(1S,8R)-1,11,11-Trimethyl-5-(5-methyl-1-phenyl-1H-pyrazol-4-yl)-3,4-diaza-tricyclo[6.2.1.0$^{2,7}$]undeca-2(7),3,5-triene;
(1S,8R)-1,11,11-Trimethyl-5-(2-trifluoromethyl-phenyl)-3,4-diazatricyclo[6.2.1.0$^{2,7}$]undeca-2(7),3,5-triene;
(1S,8R)-1,11,11-Trimethyl-5-(1-phenyl-5-trifluoromethyl-1H-pyrazol-4-yl)-3,4-diaza-tricyclo[6.2.1.0$^{2,7}$]undeca-2(7),3,5-triene;
(1S,8R)-5-Adamantan-1-yl-1,11,11-trimethyl-3,4-diaza-tricyclo[6.2.1.0$^{2,7}$]undeca-2,4,6-triene;
(1S,8R)-5-[2-(3-Chloro-phenyl)-thiazol-4-yl]-1,11,11-trimethyl-3,4-diaza-tricyclo[6.2.1.0$^{2,7}$]undeca-2,4,6-triene;
(1R,8S)-5-(2-Chloro-phenyl)-1,11,11-trimethyl-3,4-diaza-tricyclo[6.2.1.0$^{2,7}$]undeca-2,4,6-triene;
(1S,8R)-1,11,11-Trimethyl-5-phenyl-3,4-diaza-tricyclo[6.2.1.0$^{2,7}$]undeca-2,4,6-triene;
(1R,8S)-1,11,11-Trimethyl-5-phenyl-3,4-diaza-tricyclo[6.2.1.0$^{2,7}$]undeca-2,4,6-triene;
(1R,8S)-1,11,11-Trimethyl-5-(2-trifluoromethyl-phenyl)-3,4-diazatricyclo[6.2.1.0$^{2,7}$]undeca-2,4,6-triene;
(1R,8S)-1,11,11-Trimethyl-5-(4-trifluoromethyl-phenyl)-3,4-diazatricyclo[6.2.1.0$^{2,7}$]undeca-2,4,6-triene;
(1S,8R)-5-(4-Fluoro-phenyl)-1,11,11-trimethyl-3,4-diaza-tricyclo[6.2.1.0$^{2,7}$]undeca-2,4,6-triene;
(1S,8R)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene;
(1S,8R)-5-(2-Chloro-phenyl)-1,11,11-trimethyl-3,4-diaza-tricyclo[6.2.1.0$^{2,7}$]undeca-2,4,6-triene;
(1R,8S)-1,11,11-Trimethyl-5-(1-phenyl-5-trifluoromethyl-1H-pyrazol-4-yl)-3,4-diaza-tricyclo[6.2.1.0$^{2,7}$]undeca-2,4,6-triene;
(1R,8S)-5-[1-(4-Chloro-phenyl)-5-trifluoromethyl-1H-pyrazol-4-yl]-1,11,11-trimethyl-3,4-diaza-tricyclo[6.2.1.0$^{2,7}$]undeca-2,4,6-triene;
(1R,8S)-1,11,11-Trimethyl-5-(5-methyl-1-phenyl-1H-pyrazol-4-yl)-3,4-diaza-tricyclo[6.2.1.0$^{2,7}$]undeca-2,4,6-triene;
(1S,8R)-5-(2,4-Difluoro-phenyl)-1,11,11-trimethyl-3,4-diaza-tricyclo[6.2.1.0$^{2,7}$]undeca-2,4,6-triene;
(1S,8R)-5-(2-Fluoro-phenyl)-1,11,11-trimethyl-3,4-diaza-tricyclo[6.2.1.0$^{2,7}$]undeca-2,4,6-triene;
(1S,8R)-5-(2,5-Difluoro-phenyl)-1,11,11-trimethyl-3,4-diaza-tricyclo[6.2.1.0$^{2,7}$]undeca-2,4,6-triene;
(1S,8R)-1,11,11-Trimethyl-5-(1-phenyl-5-propyl-1H-pyrazol-4-yl)-3,4-diazatricyclo[6.2.1.0$^{2,7}$]undeca-2(7),3,5-triene;
(1S,8R)-1,11,11-Trimethyl-5-(1-methyl-1H-indol-3-yl)-3,4-diaza-tricyclo[6.2.1.0$^{2,7}$]undeca-2(7),3,5-triene;
(1S,8R)-5-[1-(4-Chloro-phenyl)-cyclopropyl]-1,11,11-trimethyl-3,4-diaza-tricyclo[6.2.1.0$^{2,7}$]undeca-2,4,6-triene;
(1S,8R)-5-[1-(4-Chloro-phenyl)-cyclobutyl]-1,11,11-trimethyl-3,4-diaza-tricyclo[6.2.1.0$^{2,7}$]undeca-2,4,6-triene;
(1S,8R)-5-[1-(4-Fluoro-phenyl)-5-trifluoromethyl-1H-pyrazol-4-yl]-1,11,11-trimethyl-3,4-diazatricyclo[6.2.1.0$^{2,7}$]undeca-2(7),3,5-triene;
(1S,8R)-5-Cyclopropyl-1,11,11-trimethyl-3,4-diaza-tricyclo[6.2.1.0$^{2,7}$]undeca-2(7),3,5-triene;
(1SR,8RS)-5-(5-Methyl-1-phenyl-1H-pyrazol-4-yl)-3,4-diaza-tricyclo[6.2.1.0$^{2,7}$]undeca-2(7),3,5-triene;
(1SR,8RS)-5-(2-Trifluoromethyl-phenyl)-3,4-diaza-tricyclo[6.2.1.0$^{2,7}$]undeca-2(7),3,5-triene;
(1S,8R)-5-(3-Fluoro-2-trifluoromethyl-phenyl)-1,11,11-trimethyl-3,4-diaza-tricyclo[6.2.1.0$^{2,7}$]undeca-2,4,6-triene;
(1SR,8RS)-5-[1-(4-Fluoro-phenyl)-5-trifluoromethyl-1H-pyrazol-4-yl]-3,4-diaza-tricyclo[6.2.1.0$^{2,7}$]undeca-2,4,6-triene;
(1SR,8RS)-5-(2,4-Difluoro-phenyl)-3,4-diaza-tricyclo[6.2.1.0$^{2,7}$]undeca-2,4,6-triene;
(1SR,8RS)-5-(2-Fluoro-phenyl)-3,4-diaza-tricyclo[6.2.1.0$^{2,7}$]undeca-2,4,6-triene;
(1SR,8RS)-5-(4-Fluoro-2-trifluoromethyl-phenyl)-3,4-diaza-tricyclo[6.2.1.0$^{2,7}$]undeca-2,4,6-triene;
(1S,8R)-5-(5-Methoxy-2-trifluoromethyl-phenyl)-1,11,11-trimethyl-3,4-diaza-tricyclo[6.2.1.0$^{2,7}$]undeca-2,4,6-triene;
(1S,8R)-5-(4-Fluoro-2-trifluoromethyl-phenyl)-1,11,11-trimethyl-3,4-diaza-tricyclo[6.2.1.0$^{2,7}$]undeca-2,4,6-triene;
(1S,8R)-1,11,11-Trimethyl-5-(3-trifluoromethyl-1H-pyrazol-4-yl)-3,4-diaza-tricyclo[6.2.1.0$^{2,7}$]undeca-2,4,6-triene; and
(1S,8R)-5-(5-Butoxy-1-methyl-1H-pyrazol-4-yl)-1,11,11-trimethyl-3,4-diaza-tricyclo[6.2.1.0$^{2,7}$]undeca-2,4,6-triene.

11. The compound according to claim 1 selected from:
(1SR,8RS)-5-(3-Fluoro-2-trifluoromethyl-phenyl)-3,4-diaza-tricyclo[6.2.1.0$^{2,7}$]undeca-2,4,6-triene;
(1SR,8RS)-5-Cyclopropyl-3,4-diaza-tricyclo[6.2.1.0$^{2,7}$]undeca-2,4,6-triene;

(1SR,8RS)-5-(5-Fluoro-2-trifluoromethyl-phenyl)-3,4-diaza-tricyclo[6.2.1.0$^{2,7}$]undeca-2,4,6-triene;

(1SR,8RS)-5-(1-Methyl-3-trifluoromethyl-1H-pyrazol-4-yl)-3,4-diaza-tricyclo[6.2.1.0$^{2,7}$]undeca-2,4,6-triene;

(1S,8R)-5-(2-Chloro-4-fluoro-phenyl)-1,11,11-trimethyl-3,4-diaza-tricyclo[6.2.1.0$^{2,7}$]undeca-2,4,6-triene;

(1S,8R)-5-(2-Chloro-4-fluoro-5-methoxy-phenyl)-1,11,11-trimethyl-3,4-diaza-tricyclo[6.2.1.0$^{2,7}$]undeca-2,4,6-triene;

(1S,8R)-5-(2-Chloro-4,5-difluoro-phenyl)-1,11,11-trimethyl-3,4-diaza-tricyclo[6.2.1.0$^{2,7}$]undeca-2,4,6-triene;

(1SR,8RS)-5-(2-Chloro-4-fluoro-phenyl)-3,4-diaza-tricyclo[6.2.1.0$^{2,7}$]undeca-2(7),3,5-triene;

(1SR,8RS)-5-(5-Chloro-2-trifluoromethyl-phenyl)-3,4-diaza-tricyclo[6.2.1.0$^{2,7}$]undeca-2(7),3,5-triene;

(1SR,8RS)-5-(2-Chloro-4,5-difluoro-phenyl)-3,4-diaza-tricyclo[6.2.1.0$^{2,7}$]undeca-2(7),3,5-triene;

(1S,8R)-1,11,11-Trimethyl-5-(4-methyl-2-phenyl-thiazol-5-yl)-3,4-diaza-tricyclo[6.2.1.0$^{2,7}$]undeca-2,4,6-triene;

(1SR,8RS)-5-(2-Methoxy-phenyl)-3,4-diaza-tricyclo[6.2.1.0$^{2,7}$]undeca-2,4,6-triene;

(1SR,8RS)-5-o-Tolyl-3,4-diaza-tricyclo[6.2.1.0$^{2,7}$]undeca-2,4,6-triene;

(1S,8R)-5-(2-Methoxy-phenyl)-1,11,11-trimethyl-3,4-diaza-tricyclo[6.2.1.0$^{2,7}$]undeca-2,4,6-triene;

(1S,8R)-1,11,11-Trimethyl-5-o-tolyl-3,4-diaza-tricyclo[6.2.1.0$^{2,7}$]undeca-2,4,6-triene;

(1S,8R)-5-(4-Chloro-2-methyl-phenyl)-3,4-diaza-tricyclo[6.2.1.0$^{2,7}$]undeca-2(7),3,5-triene;

(1S,8R)-1,11,11-Trimethyl-5-(1-methyl-1H-pyrrol-2-yl)-3,4-diaza-tricyclo[6.2.1.0$^{2,7}$]undeca-2,4,6-triene;

(1SR,8RS)-5-(1-Methyl-1H-pyrrol-2-yl)-3,4-diaza-tricyclo[6.2.1.0$^{2,7}$]undeca-2,4,6-triene;

(1S,8R)-5-(4-Chloro-2-methyl-phenyl)-1,11,11-trimethyl-3,4-diaza-tricyclo[6.2.1.0$^{2,7}$]undeca-2(7),3,5-triene;

(1SR,8RS)-5-(4-Fluoro-2-methyl-phenyl)-3,4-diaza-tricyclo[6.2.1.0$^{2,7}$]undeca-2(7),3,5-triene;

(1S,8R)-5-(5-Fluoro-2-methoxy-phenyl)-1,11,11-trimethyl-3,4-diaza-tricyclo[6.2.1.0$^{2,7}$]undeca-2,4,6-triene;

(1SR,8RS)-5-(5-Fluoro-2-methoxy-phenyl)-3,4-diaza-tricyclo[6.2.1.0$^{2,7}$]undeca-2,4,6-triene;

(1S,8R)-5-(4-Fluoro-2-methyl-phenyl)-1,11,11-trimethyl-3,4-diaza-tricyclo[6.2.1.0$^{2,7}$]undeca-2(7),3,5-triene;

(1SR,8RS)-5-(1-tert-Butyl-5-trifluoromethyl-1H-pyrazol-4-yl)-3,4-diaza-tricyclo[6.2.1.0$^{2,7}$]undeca-2,4,6-triene;

(1S,8R)-5-(1-tert-Butyl-5-trifluoromethyl-1H-pyrazol-4-yl)-1,11,11-trimethyl-3,4-diaza-tricyclo[6.2.1.0$^{2,7}$]undeca-2,4,6-triene;

(1SR,8RS)-5-(2-Trifluoromethoxy-phenyl)-3,4-diaza-tricyclo[6.2.1.0$^{2,7}$]undeca-2,4,6-triene;

(1S,8R)-1,11,11-Trimethyl-5-(1-methyl-cyclopropyl)-3,4-diaza-tricyclo[6.2.1.0$^{2,7}$]undeca-2,4,6-triene;

(1S,8R)-1,11,11-Trimethyl-5-(2-trifluoromethoxy-phenyl)-3,4-diaza-tricyclo[6.2.1.0$^{2,7}$]undeca-2,4,6-triene;

(1S,8R)-5-(1-tert-Butyl-5-methyl-1H-pyrazol-4-yl)-1,11,11-trimethyl-3,4-diaza-tricyclo[6.2.1.0$^{2,7}$]undeca-2,4,6-triene;

(1SR,8RS)-5-(1-tert-Butyl-5-methyl-1H-pyrazol-4-yl)-3,4-diaza-tricyclo[6.2.1.0$^{2,7}$]undeca-2,4,6-triene;

(1SR,8RS)-5-(1-tert-Butyl-5-cyclopropyl-1H-pyrazol-4-yl)-3,4-diaza-tricyclo[6.2.1.0$^{2,7}$]undeca-2,4,6-triene;

(1S,8R)-5-(1-tert-Butyl-5-cyclopropyl-1H-pyrazol-4-yl)-1,11,11-trimethyl-3,4-diaza-tricyclo[6.2.1.0$^{2,7}$]undeca-2,4,6-triene;

(1S,8R)-5-(5-Cyclopropyl-1-methyl-1H-pyrazol-4-yl)-1,11,11-trimethyl-3,4-diaza-tricyclo[6.2.1.0$^{2,7}$]undeca-2,4,6-triene;

(1SR,8RS)-5-(5-Cyclopropyl-1-methyl-1H-pyrazol-4-yl)-3,4-diaza-tricyclo[6.2.1.0$^{2,7}$]undeca-2,4,6-triene;

(1S,8R)-5-Cyclobutyl-1,11,11-trimethyl-3,4-diaza-tricyclo[6.2.1.0$^{2,7}$]undeca-2,4,6-triene;

(1SR,8RS)-5-Cyclobutyl-3,4-diaza-tricyclo[6.2.1.0$^{2,7}$]undeca-2,4,6-triene;

(1S,8R)-5-(1,3-Dimethyl-1H-pyrazol-4-yl)-1,11,11-trimethyl-3,4-diaza-tricyclo[6.2.1.0$^{2,7}$]undeca-2,4,6-triene;

(1S,8R)-1,11,11-Trimethyl-5-(1-methyl-5-trifluoromethyl-1H-pyrazol-4-yl)-3,4-diaza-tricyclo[6.2.1.0$^{2,7}$]undeca-2,4,6-triene;

(1S,8R)-5-(1-Benzyl-5-trifluoromethyl-1H-pyrazol-4-yl)-1,11,11-trimethyl-3,4-diaza-tricyclo[6.2.1.0$^{2,7}$]undeca-2,4,6-triene;

(1S,8R)-5-(1-Benzyl-5-methyl-1H-pyrazol-4-yl)-1,11,11-trimethyl-3,4-diaza-tricyclo[6.2.1.0$^{2,7}$]undeca-2,4,6-triene;

(1S,8R)-5-(1-Benzyl-3-methyl-1H-pyrazol-4-yl)-1,11,11-trimethyl-3,4-diaza-tricyclo[6.2.1.0$^{2,7}$]undeca-2,4,6-triene;

(1SR,8RS)-5-Cyclopropyl-6-methyl-3,4-diaza-tricyclo[6.2.1.0$^{2,7}$]undeca-2,4,6-triene;

(1S,8R)-5-Cyclopropyl-1,6,11,11-tetramethyl-3,4-diaza-tricyclo[6.2.1.0$^{2,7}$]undeca-2,4,6-triene;

(1S,8R)-5-(1-tert-Butyl-5-phenyl-1H-pyrazol-4-yl)-1,11,11-trimethyl-3,4-diaza-tricyclo[6.2.1.0$^{2,7}$]undeca-2,4,6-triene;

(1S,8R)-5-(4-Chloro-benzyl)-1,11,11-trimethyl-3,4-diaza-tricyclo[6.2.1.0$^{2,7}$]undeca-2,4,6-triene;

(1S,8R)-1,11,11-Trimethyl-5-(1-trifluoromethyl-cyclopropyl)-3,4-diaza-tricyclo[6.2.1.0$^{2,7}$]undeca-2,4,6-triene;

(1R,8 S)-5-Cyclopropyl-1,11,11-trimethyl-3,4-diaza-tricyclo[6.2.1.0$^{2,7}$]undeca-2(7),3,5-triene;

(1SR,8RS)-5-(2,5-Dichloro-phenyl)-3,4-diaza-tricyclo[6.2.1.0$^{2,7}$]undeca-2(7),3,5-triene;

(1SR,8RS)-5-(2,3-Dimethyl-phenyl)-3,4-diaza-tricyclo[6.2.1.0$^{2,7}$]undeca-2(7),3,5-triene;

(1SR,8RS)-5-(2,4-Dichloro-phenyl)-3,4-diaza-tricyclo[6.2.1.0$^{2,7}$]undeca-2(7),3,5-triene;

(1SR,8RS)-5-(2,3-Dichloro-phenyl)-3,4-diaza-tricyclo[6.2.1.0$^{2,7}$]undeca-2(7),3,5-triene;

(1SR,8RS)-5-(2,4-Dimethyl-phenyl)-3,4-diaza-tricyclo[6.2.1.0$^{2,7}$]undeca-2(7),3,5-triene;

(1R,8S)-5-Cyclopropyl-8,11,11-trimethyl-3,4-diaza-tricyclo[6.2.1.0$^{2,7}$]undeca-2(7),3,5-triene and (1S,8R)-5-Cyclopropyl-8,11,11-trimethyl-3,4-diaza-tricyclo[6.2.1.0$^{2,7}$]undeca-2(7),3,5-triene.

12. The compound according to claim 1 selected from:

(1S,8R)-1,11,11-Trimethyl-5-(5-methyl-1-phenyl-1H-pyrazol-4-yl)-3,4-diaza-tricyclo[6.2.1.0$^{2,7}$]undeca-2(7),3,5-triene;

(1S,8R)-1,11,11-Trimethyl-5-(2-trifluoromethyl-phenyl)-3,4-diazatricyclo[6.2.1.0$^{2,7}$]undeca-2(7),3,5-triene;

(1S,8R)-1,11,11-Trimethyl-5-(1-phenyl-5-trifluoromethyl-1H-pyrazol-4-yl)-3,4-diaza-tricyclo[6.2.1.0$^{2,7}$]undeca-2(7),3,5-triene;

(1S,8R)-1,11,11-Trimethyl-5-phenyl-3,4-diaza-tricyclo[6.2.1.0$^{2,7}$]undeca-2,4,6-triene;

(1S,8R)-5-[1-(4-Chloro-phenyl)-5-trifluoromethyl-1H-pyrazol-4-yl]-1,11,11-trimethyl-3,4-diaza-tricyclo[6.2.1.0²,⁷]undeca-2,4,6-triene;

(1S,8R)-5-(2-Chloro-phenyl)-1,11,11-trimethyl-3,4-diaza-tricyclo[6.2.1.0²,⁷]undeca-2,4,6-triene;

(1S,8R)-5-(2-Fluoro-phenyl)-1,11,11-trimethyl-3,4-diaza-tricyclo[6.2.1.0²,⁷]undeca-2,4,6-triene;

(1S,8R)-1,11,11-Trimethyl-5-(1-phenyl-5-propyl-1H-pyrazol-4-yl)-3,4-diazatricyclo[6.2.1.0²,⁷]undeca-2(7),3,5-triene;

(1S,8R)-5-[1-(4-Chloro-phenyl)-cyclopropyl]-1,11,11-trimethyl-3,4-diaza-tricyclo[6.2.1.0²,⁷]undeca-2,4,6-triene;

(1S,8R)-5-[1-(4-Chloro-phenyl)-cyclobutyl]-1,11,11-trimethyl-3,4-diaza-tricyclo[6.2.1.0²,⁷]undeca-2,4,6-triene;

(1S,8R)-5-Cyclopropyl-1,11,11-trimethyl-3,4-diaza-tricyclo[6.2.1.0²,⁷]undeca-2(7),3,5-triene;

(1SR,8RS)-5-(2-Trifluoromethyl-phenyl)-3,4-diaza-tricyclo[6.2.1.0²,⁷]undeca-2(7),3,5-triene;

(1SR,8RS)-5-[1-(4-Fluoro-phenyl)-5-trifluoromethyl-1H-pyrazol-4-yl]-3,4-diaza-tricyclo[6.2.1.0²,⁷]undeca-2,4,6-triene;

(1SR,8RS)-5-(4-Fluoro-2-trifluoromethyl-phenyl)-3,4-diaza-tricyclo[6.2.1.0²,⁷]undeca-2,4,6-triene; and (1S,8R)-5-(4-Fluoro-2-trifluoromethyl-phenyl)-1,11,11-trimethyl-3,4-diaza-tricyclo[6.2.1.0²,⁷]undeca-2,4,6-triene.

13. The compound according to claim 1 selected from:

(1S,8R)-5-Cyclopropyl-1,11,11-trimethyl-3,4-diaza-tricyclo[6.2.1.0²,⁷]undeca-2(7),3,5-triene;

(1SR,8RS)-5-(2-Trifluoromethyl-phenyl)-3,4-diaza-tricyclo[6.2.1.0²,⁷]undeca-2(7),3,5-triene;

(1SR,8RS)-5-(5-Chloro-2-trifluoromethyl-phenyl)-3,4-diaza-tricyclo[6.2.1.0²,⁷]undeca-2(7),3,5-triene;

(1S,8R)-1,11,11-Trimethyl-5-(1-methyl-cyclopropyl)-3,4-diaza-tricyclo[6.2.1.0²,⁷]undeca-2,4,6-triene;

(1S,8R)-5-Cyclopropyl-1,6,11,11-tetramethyl-3,4-diaza-tricyclo[6.2.1.0²,⁷]undeca-2,4,6-triene;

(1S,8R)-1,11,11-Trimethyl-5-(1-trifluoromethyl-cyclopropyl)-3,4-diaza-tricyclo[6.2.1.0²,⁷]undeca-2,4,6-triene; and (1R,8S)-5-Cyclopropyl-1,11,11-trimethyl-3,4-diaza-tricyclo[6.2.1.0²,⁷]undeca-2(7),3,5-triene.

14. A process for the preparation of a compound according to claim 1, comprising the step of reacting a compound according to formula

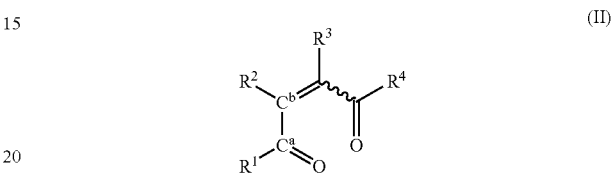

(II)

with hydrazine; wherein $R^1$ to $R^4$ are defined as in claim 1.

15. A pharmaceutical composition, comprising a therapeutically effective amount of a compound according to claim 1 and a therapeutically inert carrier.

16. A method for the treatment of type II diabetes, comprising the step of administering a therapeutically effective amount of a compound according to claim 1 to a patient in need thereof.

17. The compound according to claim 1, wherein said compound is (1S,8R)-5-Cyclopropyl-1,11,11-trimethyl-3,4-diaza-tricyclo[6.2.1.0²,⁷]undeca-2(7),3,5-triene.

* * * * *